United States Patent
Boutros et al.

(10) Patent No.: US 10,065,939 B2
(45) Date of Patent: *Sep. 4, 2018

(54) CHROMENE DERIVATIVES AND THEIR ANALOGS AS WNT PATHWAY ANTAGONISTS

(71) Applicants: Deutsches Krebsforschungszentrum, Heidelberg (DE); Ruprecht-Karls-Universität Heidelberg, Heidelberg (DE)

(72) Inventors: Michael Boutros, Heidelberg (DE); Rajendra-Prasad Maskey, Heidelberg (DE); Corinna Koch, Einhausen (DE); Florian Fuchs, Weil am Rhein (DE); Sandra Steinbrink, Eppstein (DE); Daniel Gilbert, Heidelberg (DE)

(73) Assignees: Deutsches Krebsforschungszentrum, Heidelberg (DE); Ruprecht-Karls-Universität Heidelberg, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,733

(22) Filed: May 19, 2016

(65) Prior Publication Data

US 2016/0355496 A1 Dec. 8, 2016

Related U.S. Application Data

(63) Continuation of application No. 13/885,127, filed as application No. PCT/EP2011/069927 on Nov. 11, 2011, now Pat. No. 9,371,333.

(30) Foreign Application Priority Data

Nov. 12, 2010 (EP) .................................. 10191072

(51) Int. Cl.
| | |
|---|---|
| *C07D 311/92* | (2006.01) |
| *C07D 311/96* | (2006.01) |
| *C07D 413/04* | (2006.01) |
| *C07D 491/04* | (2006.01) |
| *C07D 493/04* | (2006.01) |
| *C07D 311/04* | (2006.01) |
| *C07D 491/052* | (2006.01) |

(52) U.S. Cl.
CPC .......... *C07D 311/92* (2013.01); *C07D 311/04* (2013.01); *C07D 311/96* (2013.01); *C07D 413/04* (2013.01); *C07D 491/04* (2013.01); *C07D 491/052* (2013.01); *C07D 493/04* (2013.01)

(58) Field of Classification Search
CPC ............. C07D 311/04; C07D 491/052; C07D 493/04; C07D 311/96; C07D 413/04; C07D 491/04; C07D 311/92
See application file for complete search history.

(56) References Cited

U.S. PATENT DOCUMENTS

| | | |
|---|---|---|
| 5,041,138 A | 8/1991 | Vacanti et al. |
| 6,906,203 B1 | 6/2005 | Drewe et al. |
| 2003/0064384 A1 | 4/2003 | Hung et al. |
| 2007/0219257 A1 | 9/2007 | Beachy et al. |
| 2009/0247566 A1 | 10/2009 | Kornienko et al. |

FOREIGN PATENT DOCUMENTS

| | | |
|---|---|---|
| EP | 0537949 A1 | 4/1993 |
| EP | 0599514 A2 | 6/1994 |
| EP | 0618206 A1 | 10/1994 |

(Continued)

OTHER PUBLICATIONS

Barker et al., "Mining the Wnt pathway for cancer therapeutics," Nat Rev Drug Discov. 5(12):997-1014 (2006).
Barker et al., "Mining the Wnt pathway for cancer therapeutics," Nat Rev Drug Discov. 6(3):249 (2007).
Batra et al., "Methylenedioxy-benzopyran analogs of podophyllotoxin, a new synthetic class of antimitotic agents that inhibit tubulin polymerization," Biochem Pharmacol. 37(13):2595-2602 (1988).
Buchwald et al., "Long-term, continuous intravenous heparin administration by an implantable infusion pump in ambulatory patients with recurrent venous thrombosis," Surgery. 88(4):507-516 (1980).
Davidson et al., "Casein kinase 1 γ couples Wnt receptor activation to cytoplasmic signal transduction," Nature. 438(7069):867-872 (2005).

(Continued)

*Primary Examiner* — Angela C Brown-Pettigrew
(74) *Attorney, Agent, or Firm* — Clark & Elbing LLP

(57) ABSTRACT

Compounds of formula (IIc); wherein $X^3$ and $X^4$ independently from each other are N or $CR^8$ wherein $R^8$ may be same or different; $Y^1$, $Y^2$, $Y^3$ and $Y^4$ independently from each other are N or $CR^9$ wherein $R^9$ may be same or different and wherein up to 3 of the group $Y^1$, $Y^2$, $Y^3$ and $Y^4$ may be N; their solvates, hydrates, and pharmaceutically acceptable salts, their use for modulating the Wnt signalling pathway activity and their use as a medicament, preferably for the treatment of cancer.

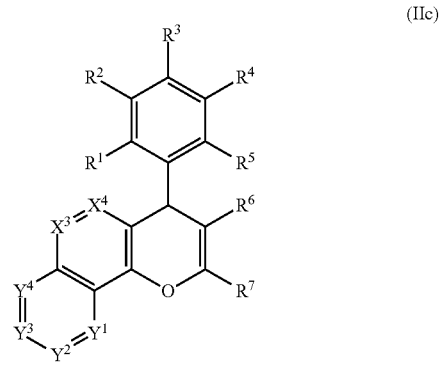

8 Claims, No Drawings

(56) References Cited

FOREIGN PATENT DOCUMENTS

| | | |
|---|---|---|
| EP | 0619314 A1 | 10/1994 |
| WO | WO-01/34591 A2 | 5/2001 |
| WO | WO-02/092083 A1 | 11/2002 |
| WO | WO-02/092594 A1 | 11/2002 |
| WO | WO-03/062392 A2 | 7/2003 |
| WO | WO-03/096982 A2 | 11/2003 |
| WO | WO-03/097806 A2 | 11/2003 |
| WO | WO-2005/033288 A2 | 4/2005 |
| WO | WO-2008/005572 A2 | 1/2008 |
| WO | WO-2009/086303 A2 | 7/2009 |
| WO | WO-2010/056662 A1 | 5/2010 |

OTHER PUBLICATIONS

During et al., "Controlled release of dopamine from a polymeric brain implant: in vivo characterization," Ann Neurol. 25(4):351-356 (1989).
Fadden et al., "Application of chemoproteomics to drug discovery: Identification of a clinical candidate targeting hsp90," Chem Biol. 17(7):686-694 (2010).
Freed et al., "Neocartilage formation in vitro and in vivo using cells cultured on synthetic biodegradable polymers," J Biomed Mater Res. 27(1):11-23 (1993).
Goodrich et al., "Altered neural cell fates and medulloblastoma in mouse patched mutants," Science. 277(5329):1109-1113 (1997).
Goodson, Dental Applications. *Medical Applications of Controlled Release. Volume II: Applications and Evaluation.* Robert S. Langer and Donald L. Wise, 115-138 (1985).
Grande et al., "The repair of experimentally produced defects in rabbit articular cartilage by autologous chondrocyte transplantation," J Orthop Res. 7(2):208-218 (1989).
Howard et al., "Acute subdural hematomas: An age-dependent clinical entity," J Neurosurg. 71(6):858-863 (1989).
Huang et al., "Tankyrase inhibition stabilizes axin and antagonizes Wnt signalling," Nature. 461(7264):614-620 (2009).
International Search Report for International Patent Application No. PCT/EP2011/069927, dated Jun. 8, 2012 (4 pages).
International Search Report for International Patent Application No. PCT/EP2011/069940, dated Nov. 13, 2012 (6 pages).
Johnson et al., "Human homolog of patched, a candidate gene for the basal cell nevus syndrome," Science. 272(5268):1668-1671 (1996).
Jung et al., "Quantitative structure-activity relationship (QSAR) of tacrine derivatives against acetylcholinesterase (AChE) activity using variable selections," Bioorg Med Chem Lett. 17(4):1082-1090 (2007).
Kemnitzer et al., "Discovery of 4-aryl-4H-chromenes as a new series of apoptosis inducers using a cell- and caspase-based high-throughput screening assay. 3. Structure-activity relationships of fused rings at the 7,8-positions," J Med Chem. 50(12):2858-2864 (2007).
Krauss, Malfunction of Signaling Pathways and Tumorigenesis. Biochemistry of Signal Transduction and Regulation. Wiley-VCH, 578-580 (2008).
Langer et al., "Chemical and physical structure of polymers as carriers for controlled release of bioactive agents: A review," Rev Macromol Chem Phys. 23(1):61-126 (1983).
Langer, "New methods of drug delivery," Science. 249(4976):1527-33 (1990).
Leon et al., "Synthesis, acetylcholinesterase inhibition and neuroprotective activity of new tacrine analogues," Bioorg Med Chem. 13(4):1167-1175 (2005).
Levy et al., "Inhibition of calcification of bioprosthetic heart valves by local controlled-release diphosphonate," Science. 228(4696):190-192 (1985).
Li et al., "Calpain as an effector of the Gq signaling pathway for inhibition of Wnt/beta-catenin-regulated cell proliferation," Proc Natl Acad Sci U S A. 99(20):13254-13259 (2002).
Lu et al., "Spiperone enhances intracellular calcium level and inhibits the Wnt signaling pathway," BMC Pharmacol. 9:1-8 (2009).
Marco-Contelles et al., "Synthesis and biological evaluation of new 4H-pyrano[2,3-b]quinoline derivatives that block acetylcholinesterase and cell calcium signals, and cause neuroprotection against calcium overload and free radicals," Eur J Med Chem. 41(12):1464-1469 (2006).
Morin, "Beta-catenin signaling and cancer," Bioessays. 21(12):1021-30 (1999).
Nusse, "Wnt signaling in disease and in development," Cell Res. 15(1):28-32 (2005).
Oro et al., "Basal cell carcinomas in mice overexpressing sonic hedgehog," Science. 276(5313):817-821 (1997).
Pecina-Slaus, "Wnt signal transduction pathway and apoptosis: a review," Cancer Cell Int. 10:22 (2010) (5 pages).
RN 111861-25-7. Retrieved on May 15, 2012 (1 page).
RN 111861-41-7. Retrieved on May 15, 2012 (2 pages).
RN 302802-16-0 and 331856-38-3. Retrieved on May 15, 2012 (2 pages).
RN 312266-55-0 and 326865-74-1. Retrieved on May 15, 2012 (2 pages).
RN 312266-56-1 and 332030-67-8. Retrieved on May 15, 2012 (2 pages).
RN 326919-67-9 and 591738-56-6. Retrieved on May 15, 2012 (2 pages).
RN 331859-87-1. Retrieved on May 15, 2012 (2 pages).
RN 339062-56-5, 592514-17-5, 1139899-65-2, 1139899-68-5, 119825-05-7, 119825-06-8, 130944-10-4, 130944-11-5, 149550-35-6, 149550-36-7, 149550-43-6, 149550-68-5, 331869-77-3, 33062-56-5, 592514-17-5, 663210-32-0, 709617-52-7, 860787-48-0, 1139899-65-2, 1139899-66-3, and 1139899-68-5. Retrieved on Apr. 26, 2012 (8 pages).
RN 339062-70-3, 414897-39-5, and 663207-31-6. Retrieved on May 15, 2012 (2 pages).
RN 364151-82-6. Retrieved on May 15, 2012 (2 pages).
RN 389636-76-4, 389636-77-5, 389636-85-5, 389636-86-6, 389636-87-7, 389636-88-8, 389636-96-8, 389636-97-9, 389636-98-0, 389636-93-5, 389636-94-6, 389636-90-2, 389636-91-3, 389636-92-4, and 389636-95-7. Retrieved on Apr. 27, 2012 (9 pages).
RN 413618-84-5 and 663159-84-0. Retrieved on May 15, 2012 (2 pages).
RN 415942-83-5. Retrieved on Apr. 26, 2012 (1 page).
RN 471261-42-4. Retrieved on May 15, 2012 (2 pages).
RN 592514-12-0, 592514-13-1, 592514-19-7, 592514-20-0, 592514-22-2, 592516-11-5, 592516-12-6, 592516-14-8, and 592516-15-9. Retrieved on Apr. 26, 2012 (9 pages).
RN 654633-82-6. Retrieved on Apr. 26, 2012 (1 page).
RN 663159-07-7. Retrieved on May 15, 2012 (2 pages).
RN 663159-73-7. Retrieved on May 15, 2012 (2 pages).
RN 663208-47-7. Retrieved on May 15, 2012 (2 pages).
RN 665016-27-3 and 665024-96-4. Retrieved on Apr. 26, 2012 (2 pages).
RN 878994-90-2. Retrieved on Apr. 26, 2012 (1 page).
RN 885289-36-1. Retrieved on Apr. 26, 2012 (1 page).
RN 893778-78-4. Retrieved on Apr. 26, 2012 (1 page).
RN 89539-15-6 and 895359-28-1. Retrieved Apr. 26, 2012 (2 pages).
RN 903447-56-3, 903467-00-5, and 903467-07-2. Retrieved on Apr. 26, 2012 (3 pages).
Saudek et al., "A preliminary trial of the programmable implantable medication system for insulin delivery," N Engl J Med. 321(9):574-579 (1989).
Scholer-Dahirel et al., "Maintenance of adenomatous polyposis coli (APC)-mutant colorectal cancer is dependent on Wnt/beta-catenin signaling," Proc Natl Acad Sci U S A. 108(41):17135-17140 (2011).
Sefton, "Implantable pumps," Crit Rev Biomed Eng. 14(3):201-240 (1987).
Senthivinayagam et al., "Caspase-mediated cleavage of β-catenin precedes drug-induced apoptosis in resistant cancer cells," J Biol Chem. 284(20):13577-13588 (2009).
STN CAPLUS File, AN 2008:11449301, 2008 (8 pages).

(56) References Cited

OTHER PUBLICATIONS

STN Registry File, Received with the Japanese Office Action issued in connection with Japanese Patent Application JP2013542240 (12 pages).

Stone et al., "Future directions: Collagen-based prostheses for meniscal regeneration," Clin Orthop Relat Res. 252:129-135 (1990).

Stone et al., "The tumour-suppressor gene patched encodes a candidate receptor for Sonic hedgehog," Nature. 384(6605):129-133 (1996).

Takigawa et al., "Chondrocytes dedifferentiated by serial monolayer culture form cartilage nodules in nude mice," Bone Miner. 2(6):446-462 (1987).

Vacanti et al., "Synthetic polymers seeded with chondrocytes provide a template for new cartilage formation," Plast Reconstr Surg. 88(5):753-759 (1991).

van de Wetering et al., "Armadillo coactivates transcription driven by the product of the *Drosophila* segment polarity gene dTCF," Cell. 88(6):789-799 (1997).

von Schroeder et al., "The use of polylactic acid matrix and periosteal grafts for the reconstruction of rabbit knee articular defects," J Biomed Mater Res. 25(3):329-339 (1991).

Wakitani et al., "Repair of rabbit articular surfaces with allograft chondrocytes embedded in collagen gel," J Bone Joint Surg Br. 71(1):74-80 (1989).

Xie et al., "Mutations of the PATCHED gene in several types of sporadic extracutaneous tumors," Cancer Res. 57(12):2369-2372 (1997).

Xie et al., "Physical mapping of the 5 Mb D9S196-D9S180 interval harboring the basal cell nevus syndrome gene and localization of six genes in this region," Genes Chromosomes Cancer. 18(4):305-309 (1997).

Yamamoto, "Regulation of Wnt signaling pathway and its relationship with tumorigenesis," Seikagaku. 80(12):1079-93 (2008).

CHROMENE DERIVATIVES AND THEIR ANALOGS AS WNT PATHWAY ANTAGONISTS

The present invention relates to compounds having the general formula (IIc) with the definitions of X3, $X^4$, $Y^1$ to $Y^4$, $R^1$ to $R^5$, $R^6$ and $R^7$ given below and/or solvates, hydrates and pharmaceutically acceptable salts thereof. Furthermore, the invention relates to the use of said compounds for modulating of the Wnt signalling pathway activity and their use as a medicament, preferably for the treatment of cancer.

The Wnt signalling pathway plays an important role in the regulation of cell proliferation and differentiation. Aberrant activation of the Wnt signalling pathway is known to promote uncontrolled cell growth and survival and can therefore be a major driving force in a broad spectrum of human cancers and diseases. For example, the inhibition of aberrant Wnt signalling pathway activity in cancer cell lines effectively blocks their growth (N. Barker and H. Clevers "Mining the Wnt pathway for cancer therapeutics", Nature Reviews, vol. 5, 2007, pages 997-1014; R. Nusse, "Wnt signalling in disease and in development", Cell Research, Vol. 15, 2005, pages 23-32). Other disorders and diseases are considered to be influenced by an aberrant Wnt signalling pathway, too (see e.g. literature cited above).

The Wnt signalling pathway involves a large number of proteins regulating the production of Wnt signalling molecules, their interaction with receptors on target cells and the physiological response of target cells resulting from the exposure of cells to the extra-cellular Wnt ligands.

Secreted signalling proteins of the Wnt family bind to specific Frizzled (Frz) receptor complexes on the surface of target cells and activate distinct intracellular pathways that are broadly classified as canonical or non-canonical Wnt signalling pathways.

In brief, the canonical pathway regulates the amount of the protein beta-catenin in a cell and its ability to enter the nucleus of the cell, where it interacts with members of the Tcf/Lef protein family. Beta-catenin and Tcf form active transcription factor complexes in the nucleus and activate the Wnt target genes. The presence of the beta-catenin in the nucleus is a hallmark in the Wnt signalling pathway indicating its activation. An overview of the Wnt signalling pathway can be found in N. Barker and H. Clevers "Mining the Wnt pathway for cancer therapeutics", Nature Reviews, vol. 5, 2007, pages 997-1014.

The presence of Tcf-beta-catenin complexes in the nuclei of cells leads to activation of the genetic program considered to promote cancer formation by stimulating cell growth, blocking apoptosis and altering cell movement. For instance, the artificial disruption of Tcf-beta-catenin complex formation in colon cancer cells effectively blocks target gene activation and inhibits the growth in vitro. Drugs designed to inhibit the Wnt signalling pathway and consequently the formation of the Tcf-beta-catenin complex in the nucleus of a cell are therefore expected to hold great potential for the treatment of a range of cancers and other diseases associated with the Wnt signalling pathway.

Therefore, there is a strong need for novel compounds which modulate the Wnt signalling pathway thereby opening new routes for the treatment of disorders and/or diseases associated with an aberrant activation of Wnt signalling.

An object of the present invention is to provide such compounds. This object is achieved by a compound having the general formula (I)

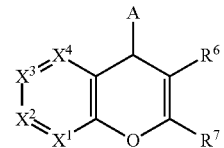

(I)

wherein
$X^1$, $X^2$, $X^3$ and $X^4$ independently from each other are N or $CR^8$ wherein $R^8$ may be same or different, and wherein up to 3 of the group $X^1$, $X^2$, $X^3$ and $X^4$ may be N;
A is selected from the group consisting of 5- to 6-membered aromatic or heteroaromatic cycles containing 1 to 3 heteroatoms selected from the group consisting of N, O and S wherein A is optionally substituted by 1 to 5 substituents R which may be same or different;
R is selected from OH; halogen; CN; $C_1$-$C_6$ alkyl; $C_3$-$C_7$ cycloalkyl; $C_3$-$C_7$ heterocyclyl; $C_2$-$C_6$ alkenyl; $C_2$-$C_6$ alkinyl; $C_3$-$C_7$ aryl; $C_3$-$C_7$ heteroaryl; $C_4$-$C_{15}$ aralkyl; $C_4$-$C_{15}$ heteroarylalkyl; $C(O)R^{1a}$; $C(O)OR^{1a}$; $C(O)N(R^{1a}R^{1b})$; $C(O)NR^{1a}(R^{1b}R^{1c})$; $C(NR^{1a}R^{1b})NOR^{1c}$; $C(NR^{1a}R^{1b})NOC(O)R^{1c}$; $S(O)_2N(R^{1a})C(O)N(R^{1b}R^{1c})$; $N(R^{1a})S(O)_2OR^{1b}$; $C(R^{1a})N(R^{1b})$; $C(R^{1a})NOR^{1b}$; $C(R^{1a})NN(R^{1b}R^{1c})$; $C(O)N(R^{1a})OR^{1b}$; $C(NR^{1a})N(R^{1b}R^{1c})$; $C(NR^{1a})N(R^{1b})OR^{1c}$; $C$ $(NR^{1a})N(R^{1b})N$ $(R^{1c}R^{1d})$; $N(R^{1a}R^{1b})$; $N(R^{1a})S(O)_2N(R^{1b}R^{1c})$; $N(R^{1a})C(O)R^{1b}$; $N(R^{1a})S(O)_2R^{1b}$; $N(R^{1a})S(O)R^{1b}$; $N(R^{1a})C(O)N(R^{1b}R^{1c})$; $N(R^{1a})C(O)OR^{1b}$; $SR^{1a}$; $S(O)_2OR^{1a}$; $S(O)_2N(R^{1a}R^{1b})$; $S(O)N(R^{1a}R^{1b})$; $S(O)_2R^{1a}$; $S(O)R^{1a}$; $OR^{1a}$; $OC(O)R^{1a}$; and $OC(O)N(R^{1a}R^{1b})$; and wherein alkyl; alkenyl, alkinyl, cycloalkyl; heterocyclyl; aryl; heteroaryl; aralkyl; and heteroarylalkyl are optionally substituted by one or more groups $R^{10}$ which are same or different; and
optionally two adjacent substituents R form together a 5- to 7-membered aromatic, heteroaromatic, alicyclic or heterocyclic ring optionally substituted by one or more groups $R^{10}$ which may be same or different;
$R^{1a}$; $R^{1b}$; $R^{1c}$; and $R^{1d}$ are independently from each other selected from H; $C_1$-$C_6$ alkyl; $C_3$-$C_7$ cycloalkyl; $C_3$-$C_7$ heterocyclyl; $C_2$-$C_6$ alkenyl; $C_2$-$C_6$ alkinyl; $C_3$-$C_7$ aryl; $C_3$-$C_7$ heteroaryl; $C_4$-$C_{15}$ aralkyl; and $C_4$-$C_{15}$ heteroarylalkyl; wherein alkyl; cycloalkyl; heterocyclyl; alkenyl; alkinyl; aryl; heteroaryl; aralkyl; and heteroarylalkyl are optionally substituted with one or more $R^{10}$ which are same or different ;
$R^{10}$ is selected from halogen, CN, OH, $C_1$-$C_6$ alkyl; $OR^{10a}$; $C(O)R^{10a}$; $C(O)OR^{10a}$; $C(O)N(R^{10a}R^{10b})$; $N(R^{10a}R^{10b})$; $OC(O)R^{10a}$; $N(R^{10a})C(O)R^{10b}$; $S(O)_2N(R^{10a}R^{10b})$; $S(O)N(R^{10a}R^{10b})$; $S(O)_2N(R^{10a})C(O)N(R^{10b}R^{10c})$; $S(O)_2R^{10a}$; $S(O)R^{10a}$; $S(O)_2OR^{10a}$; $N(R^{10a})S(O)_2N(R^{10b}R^{10c})$; $SR^{10a}$; $N(R^{10a})S(O)_2R^{10b}$; $N(R^{10a})S(O)R^{10b}$; $N(R^{10a})C(O)N(R^{10b}R^{10c})$; $N(R^{10a})C(O)OR^{10b}$; and $OC(O)N(R^{10a}R^{10b})$; wherein $C_1$-$C_6$ alkyl is optionally substituted with one or more halogen which are same or different;
$R^{10a}$; $R^{10b}$ and $R^{10c}$ are independently from each other selected from H; and $C_1$-$C_6$ alkyl; wherein $C_1$-$C_6$ alkyl is optionally substituted with one or more halogen which are same or different;
$R^6$ is selected from H; OH; CN; halogen; $C_1$-$C_6$ alkyl; $C_3$-$C_7$ cycloalkyl; $C_3$-$C_7$ heterocyclyl; $C_2$-$C_6$ alkenyl; $C_2$-$C_6$ alkinyl; $C_3$-$C_7$ aryl; $C_3$-$C_7$ heteroaryl; $C_4$-$C_{15}$ aralkyl; $C_4$-$C_{15}$ heteroarylalkyl; $C(O)R^{6a}$; $C(O)OR^{6a}$; $C(O)N(R^{6a}R^{6b})$; $C(O)N(R^{6a})OR^{6b}$; $C(O)N(R^{6a})N(R^{6b}R^{6c})$;

C(NR$^{6a}$)N(R$^{6b}$R$^{6c}$); C(NR$^{6a}$)N(R$^{6b}$)OR$^{6c}$; C(NR$^{6a}$)N(R$^{6b}$)N(R$^{6c}$R$^{6d}$); CR$^{6a}$NOR$^{6b}$; SR$^{6a}$; S(O)R$^{6a}$; S(O)$_2$R$^{6a}$; S(O)$_2$OR$^{6a}$; S(O)$_2$N(R$^{6a}$R$^{6b}$); S(O)N(R$^{6a}$R$^{6b}$); N(R$^{6a}$)S(O)$_2$N(R$^{6b}$R$^{6c}$); N(R$^{6a}$)S(O)$_2$R$^{6b}$; N(R$^{6a}$)S(O)R$^{6a}$; N(R$^{6a}$)S(O)$_2$OR$^{6b}$; N(R$^{6a}$R$^{6b}$); N(R$^{6a}$)C(O)R$^{6b}$; N(R$^{6a}$)C(O)N(R$^{6b}$R$^{6c}$); and N(R$^{6a}$)C(O)OR$^{6b}$; wherein alkyl; cycloalkyl; heterocyclyl; alkenyl; alkinyl; aryl; heteroaryl; aralkyl; and heteroarylalkyl are optionally substituted by one or more R$^{11}$, which are same or different;

R$^{6a}$; R$^{6b}$; R$^{6c}$; and R$^{6d}$ are independently from each other selected from H; C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl; C$_3$-C$_7$ aryl; C$_3$-C$_7$ heteroaryl; C$_4$-C$_{15}$ aralkyl; and C$_4$-C$_{15}$ heteroarylalkyl which are optionally substituted with one or more R$^{11}$, which are the same or different;

R$^{11}$ is selected from halogen, CN, OH, C$_1$-C$_6$ alkyl; OR$^{11a}$; C(O)R$^{11a}$; C(O)OR$^{11a}$; C(O)N(R$^{11a}$R$^{11b}$); N(R$^{11a}$R$^{11b}$); OC(O)R$^{11a}$; N(R$^{11a}$)C(O)R$^{11b}$; SR$^{11a}$; S(O)R$^{11a}$; S(O)$_2$R$^{11a}$; S(O)$_2$OR$^{11a}$; S(O)$_2$N(R$^{11a}$R$^{11b}$); S(O)N(R$^{11a}$R$^{11b}$); S(O)$_2$N(R$^{11a}$)C(O)N(R$^{11b}$R$^{11c}$); N(R$^{11a}$)S(O)$_2$N(R$^{11b}$R$^{11c}$); N(R$^{11a}$)S(O)$_2$R$^{11b}$; N(R$^{11a}$)S(O)R$^{11b}$; N(R$^{11a}$)C(O)N(R$^{11b}$R$^{11c}$); N(R$^{11a}$)C(O)OR$^{11b}$; and OC(O)N(R$^{11a}$R$^{11b}$); wherein C$_1$-C$_6$ alkyl is optionally substituted with one or more R$^{18}$ which are same or different;

R$^{18}$ is selected from halogen, CN, OH; OR$^{11a}$; C(O)R$^{11a}$; C(O)OR$^{11a}$; C(O)N(R$^{11a}$R$^{11b}$); N(R$^{11a}$R$^{11b}$); OC(O)R$^{11a}$; N(R$^{11a}$)C(O)R$^{11b}$; SR$^{11a}$; S(O)R$^{11a}$; S(O)$_2$R$^{11a}$; S(O)$_2$OR$^{11a}$; S(O)$_2$N(R$^{11a}$R$^{11b}$); S(O)N(R$^{11a}$R$^{11b}$); S(O)$_2$N(R$^{11a}$)C(O)N(R$^{11b}$R$^{11c}$); N(R$^{11a}$)S(O)$_2$N(R$^{11b}$R$^{11c}$); N(R$^{11a}$)S(O)$_2$R$^{11b}$; N(R$^{11a}$)S(O)R$^{11b}$; N(R$^{11a}$)C(O)N(R$^{11b}$R$^{11c}$); N(R$^{11a}$)C(O)OR$^{11b}$; and OC(O)N(R$^{11a}$R$^{11b}$);

R$^{11a}$; R$^{11b}$ and R$^{11c}$ are independently from each other selected from H; and C$_1$-C$_6$ alkyl; wherein C$_1$-C$_6$ alkyl is optionally substituted with one or more halogen which are the same or different;

R$^7$ is selected from H; OH; CN; halogen; C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl; C$_3$-C$_7$ aryl; C$_3$-C$_7$ heteroaryl; C$_4$-C$_{15}$ aralkyl; C$_4$-C$_{15}$ heteroarylalkyl; C(O)R$^{7a}$; C(O)OR$^{7a}$; C(NR$^{7a}$)N(R$^{7b}$)N(R$^{7c}$R$^{7d}$); C(R$^{7a}$)N(R$^{7b}$); C(R$^{7a}$)NN(R$^{7b}$R$^{7c}$); C(R$^{7a}$)NOR$^{7b}$; OR$^{7a}$; OC(O)R$^{7a}$; OC(O)N(R$^{7a}$R$^{7b}$); N(R$^{7a}$R$^{7b}$); N(R$^{7a}$)C(O)R$^{7b}$; N(R$^{7a}$)C(O)N(R$^{7b}$R$^{7c}$); N(R$^{7a}$)C(O)OR$^{7b}$; N(R$^{7a}$)S(O)$_2$OR$^{7b}$; N(R$^{7a}$)S(O)R$^{7b}$; N(R$^{7a}$)S(O)$_2$R$^{7b}$; N(R$^{7a}$)S(O)$_2$N(R$^{7b}$R$^{7c}$); SR$^{7a}$; S(O)R$^{7a}$; S(O)$_2$R$^{7a}$; S(O)$_2$OR$^{7a}$; S(O)N(R$^{7a}$R$^{7b}$); S(O)$_2$N(R$^{7a}$R$^{7b}$); S(O)$_2$N(R$^{7a}$)C(O)N(R$^{7b}$R$^{7c}$); C(NR$^{7a}$R$^{7b}$)NOR$^{7c}$; and C(NR$^{7a}$R$^{7b}$)NOC(O)R$^{7c}$; wherein alkyl; cycloalkyl; alkenyl; alkinyl; aryl; aralkyl; and heteroarylalkyl are optionally substituted by one or more R$^{12}$, which are same or different;

R$^{7a}$; R$^{7b}$; R$^{7c}$, and R$^{7d}$ are independently from each other selected from H; C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl; C$_3$-C$_7$ aryl; C$_3$-C$_7$ heteroaryl; C$_4$-C$_{15}$ aralkyl; and C$_4$-C$_{15}$ heteroarylalkyl wherein alkyl; cycloalkyl; heterocyclyl; alkenyl; alkinyl; aryl; heteroaryl; aralkyl; heteroarylalkyl are optionally substituted with one or more R$^{12}$, which are same or different;

R$^{12}$ is selected from halogen, CN, OH, C$_1$-C$_6$ alkyl; OR$^{12a}$; C(O)R$^{12a}$; C(O)OR$^{12a}$; C(O)N(R$^{12a}$R$^{12b}$); N(R$^{12a}$R$^{12b}$); OC(O)R$^{12a}$; N(R$^{12a}$)C(O)R$^{12b}$; S(O)$_2$N(R$^{12a}$R$^{12b}$); S(O)N(R$^{12a}$R$^{12b}$); S(O)$_2$R$^{12a}$; S(O)R$^{12a}$; S(O)$_2$OR$^{12a}$; N(R$^{12a}$)S(O)$_2$N(R$^{12b}$R$^{12c}$); SR$^{12a}$; N(R$^{12a}$)S(O)$_2$R$^{12b}$; N(R$^{12a}$)S(O)R$^{12b}$; N(R$^{12a}$)C(O)N(R$^{12b}$R$^{12c}$); N(R$^{12a}$)C(O)OR$^{12b}$; OC(O)N(R$^{12a}$R$^{12b}$); and S(O)$_2$N(R$^{11a}$)C(O)N(R$^{11b}$R$^{11c}$); wherein C$_1$-C$_6$ alkyl is optionally substituted with one or more halogen which are same or different;

R$^{12a}$; R$^{12b}$ and R$^{12c}$ are independently from each other selected from H; and C$_1$-C$_6$ alkyl; wherein C$_1$-C$_6$ alkyl is optionally substituted with one or more halogen which are same or different;

R$^8$ is selected from H; OH; CN, halogen, C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl; C$_3$-C$_7$ aryl; C$_3$-C$_7$ heteroaryl; C$_4$-C$_{15}$ aralkyl; C$_4$-C$_{15}$ heteroarylalkyl; C(O)R$^{8a}$; C(O)OR$^{8a}$; C(O)N(R$^{8a}$R$^{8b}$); C(O)N(R$^{8a}$)OR$^{8b}$; C(O)N(R$^{8a}$)N(R$^{8b}$R$^{8c}$); C(NR$^{8a}$)N(R$^{8b}$R$^{8c}$); C(NR$^{8a}$)N(R$^{8b}$)OR$^{8c}$; C(NR$^{8a}$)N(R$^{8b}$)N(R$^{8c}$R$^{8d}$); C(R$^{8a}$)N(R$^{8b}$); C(R$^{8a}$)NN(R$^{8b}$R$^{8c}$); C(R$^{8a}$)NOR$^{8b}$; OR$^{8a}$; OC(O)R$^{8a}$; OC(O)N(R$^{8a}$R$^{8b}$); SR$^{8a}$; S(O)R$^{8a}$; S(O)$_2$R$^{8a}$; S(O)$_2$OR$^{8a}$; S(O)$_2$N(R$^{8a}$R$^{8b}$); S(O)N(R$^{8a}$R$^{8b}$); S(O)$_2$N(R$^{8a}$)C(O)N(R$^{8b}$R$^{8c}$); N(R$^{8a}$)S(O)$_2$N(R$^{8b}$R$^{8c}$); N(R$^{8a}$)S(O)$_2$R$^{8b}$; N(R$^{8a}$)S(O)R$^{8b}$; N(R$^{8a}$)S(O)$_2$OR$^{8b}$; N(R$^{8a}$R$^{8b}$); N(R$^{8a}$)C(O)R$^{8b}$; N(R$^{8\,a}$)C(O)N(R$^{8b}$R$^{8c}$); N(R$^{8a}$)C(O)OR$^{8b}$; C(NR$^{8a}$R$^{8b}$)NOR$^{8c}$; C(NR$^{8a}$R$^{8b}$)NOC(O)R$^{8c}$; C(O)NR$^{8a}$N(R$^{8b}$R$^{8c}$); and N(R$^{8a}$)C(S)N(R$^{8b}$R$^{8c}$); wherein alkyl; cycloalkyl; heterocyclyl; alkenyl; alkinyl; aryl; heteroaryl; aralkyl; and heteroarylalkyl are optionally substituted by one or more R$^{16}$, which are same or different; and optionally two adjacent R$^8$ form together a substituted or unsubstituted 5- or 6-membered saturated or unsaturated hydrocarbon ring containing up to 3 N-atoms in the ring or a substituted or unsubstituted 5- to 7-membered cyclic monoether or diether;

R$^{8a}$; R$^{8b}$; R$^{8c}$; and R$^{8d}$ are independently from each other selected form H; C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl C$_3$-C$_7$ aryl; C$_3$-C$_7$ heteroaryl; C$_4$-C$_{15}$ aralkyl; and C$_4$-C$_{15}$ heteroarylalkyl which are optionally substituted with one or more R$^{16}$, which are same or different;

R$^{16}$ is selected from halogen, CN, OH, C$_1$-C$_6$ alkyl; OR$^{16a}$; C(O)R$^{16a}$; C(O)OR$^{16a}$; C(O)N(R$^{16a}$R$^{16b}$); N(R$^{16a}$R$^{16b}$); OC(O)R$^{16a}$; N(R$^{16a}$)C(O)R$^{16b}$; S(O)$_2$N(R$^{16a}$R$^{16b}$); S(O)N(R$^{16a}$R$^{16b}$); S(O)$_2$R$^{16a}$; S(O)R$^{16a}$; S(O)$_2$OR$^{16a}$; N(R$^{16a}$)S(O)$_2$N(R$^{16b}$R$^{16c}$); SR$^{16a}$; N(R$^{16a}$)S(O)$_2$R$^{16b}$; N(R$^{16a}$)S(O)R$^{16b}$; N(R$^{16a}$)C(O)N(R$^{16b}$R$^{16c}$); N(R$^{16a}$)C(O)OR$^{16b}$; OC(O)N(R$^{16a}$R$^{16b}$); and S(O)$_2$N(R$^{16a}$)C(O)N(R$^{16b}$R$^{16c}$); wherein C$_1$-C$_6$ alkyl is optionally substituted with one or more halogen which are same or different;

R$^{16a}$; R$^{16b}$ and R$^{16c}$ are independently from each other selected from H; and C$_1$-C$_6$ alkyl; wherein C$_1$-C$_6$ alkyl is optionally substituted with one or more halogen which are the same or different;

and/or solvates; hydrates; and pharmaceutically acceptable salts thereof.

"Alkyl" means a linear or branched saturated aliphatic hydrocarbon group, e.g. methyl, ethyl, n-propyl, i-propyl, n-butyl, i-butyl, n-pentyl, i-pentyl, n-hexyl, i-hexyl and 3-methyl-pentyl and the like.

"Alkenyl" means a linear or branched unsaturated aliphatic hydrocarbon group with at least one double bond, e.g. ethenyl, propenyl (allyl), 1-butenyl, 2-butenyl, 1-pentenyl, 2-pentenyl, 1-hexenyl, 2-hexenyl and 3-hexenyl and the like.

"Alkinyl" means a linear or branched unsaturated aliphatic hydrocarbon group with at least one triple bond, e.g. ethinyl, propinyl, 1-butinyl, 2-butinyl and the like.

"Cycloalkyl" means a saturated 3 to 8-membered hydrocarbon ring e.g. cyclopropyl, cyclobutyl, cyclopentyl, cyclohexyl and cycloheptyl.

"Alicyclic" means a saturated or unsaturated but non-aromatic 3- to 8- membered hydrocarbon ring like cyclopropane, cyclobutane, cyclopentane, cyclopentene, cyclopentadiene, cyclohexane, cyclohexene and cycloheptane.

"Heterocyclyl" and "heterocyclic" mean a saturated or unsaturated 3- to 8-membered hydrocarbon ring containing 1 to 4 heteroatoms and/or heteroatom containing groups selected from the group N, O, S and C(O) in the ring. The one or more heteroatoms and hetero atoms containing groups present in the ring replace a —$CH_2$— group or a —CH= in the ring. Preferred $C_3$-$C_8$ heterocyclyl groups containing 1 to 4 heteroatoms and heteroatom containing groups selected from the group N, O, S and C(O) are derived from the following heterocyclic compounds: tetrahydrofurane, pyrrolidine, tetrahydrothiophene, oxazolidine, piperidine, tetrahydropyrane, piperazine, dioxane, morpholine, cyclopentanone and trioxane.

"Aryl" and "aromatic" mean an aromatic 3- to 7-numbered hydrocarbon ring e.g. phenyl and the like.

"Heteroaryl" and "heteroaromatic" mean an aromatic 3- to 7-numbered hydrocarbon ring containing 1 to 4 heteroatoms selected from the group N, O, and S in the ring. The one or more heteroatoms present in the ring replace a —CH= group in the ring. Preferred $C_3$-$C_7$ heteroaryl groups containing 1 to 4 heteroatoms selected from the group N, O and S are derived from the following heteroaromatic compounds: Pyrrole, pyrazole, imidazole, triazole, tetrazole, furane, thiophene, oxazole, isoxazole, oxadiazole, thiazole, isothiazole, thiadiazole, pyridine, pyridazine, pyrimidine, pyrazine and triazine.

"Aralkyl" means a $C_3$-$C_7$ aryl group substituted with at least one $C_1$-$C_8$ alkyl group, wherein aryl and alkyl are defined as above. Examples for aralkyl are tolyl, benzyl and xylyl. The aralkyl group may be bound via the $C_1$-$C_8$ alkyl group or via the $C_3$-$C_7$ aryl group.

"Heteroarylalkyl" means a $C_3$-$C_7$ heteroaryl group substituted with at least one $C_1$-$C_8$ alkyl group, wherein heteroaryl and alkyl are defined as above. The heteroarylalkyl group may be bound via the $C_1$-$C_8$ alkyl group or via the $C_3$-$C_7$ heteroaryl group.

"Halogen" comprises F, Cl, Br and I.

Substituent A is preferably selected from the group consisting of substituted or unsubstituted monocyclic or polycyclic moieties derived from benzene, pyridine, imidazole, furane, benzofurane, indole, pyrazole, triazole, tetrazole, oxadiazole, thiadiazole, thiazole, indazole, benzooxazole, pyrimidine, pyrrolopyridine and oxazole.

In a preferred embodiment of the present invention A is phenyl which is optionally substituted by 1 to 5 substituents R which may be same or different. Compounds of this embodiment have formula

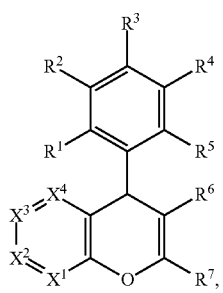

(II)

wherein $R^1$; $R^2$; $R^3$; $R^4$ and $R^5$ independently from each other are selected from the group consisting of H and the substituents as defined for R above. Within this embodiment it is even more preferred if at least 3 of the group of $R^1$; $R^2$; $R^3$; $R^4$ and $R^5$ are not H, particularly preferred $R^2$; $R^3$ and $R^4$ are not H and most preferred $R^1$ and $R^5$ are H and $R^2$; $R^3$ and $R^4$ are not H.

A preferred embodiment of the invention relates to compounds of formula (I), wherein two adjacent $R^8$ form together an optionally substituted 5- or 6-membered saturated or unsaturated hydrocarbon ring containing up to 3 N-atoms in the ring. Especially preferred, the two adjacent R8 form together an optionally substituted 5- or 6-membered aromatic ring containing up to 3 N-atoms in the ring. Within this embodiment it is particularly preferred, if the two adjacent R8 form an optionally substituted 6-membered aromatic ring containing up to 3 N-atoms. According to this embodiment the two adjacent $R^8$ may be selected from $R^8$ bound to $X^3$ and $X^4$ (formula (Ia)); $R^8$ bound to $X^2$ and $X^3$ (formula (Ib)) or $R^8$ bound to $X^1$ and $X^2$ (formula (Ic)):

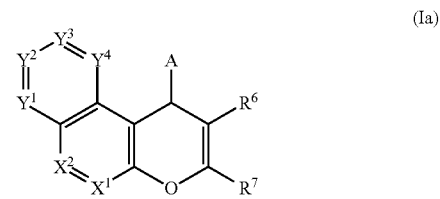

(Ia)

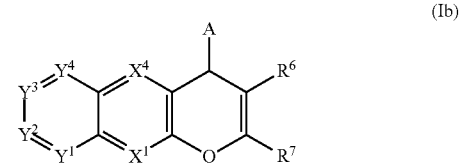

(Ib)

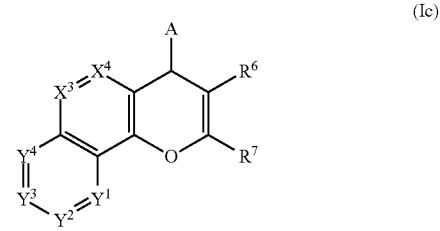

(Ic)

wherein $Y^1$, $Y^2$, $Y^3$ and $Y^4$ independently from each other are N or $CR^9$ wherein $R^9$ may be same or different, and wherein up to 3 of the group $Y^1$, $Y^2$, $Y^3$ and $Y^4$ may be N;

$R^9$ is selected from H; OH; halogen; CN; $C_1$-$C_6$ alkyl; $C_3$-$C_7$ cycloalkyl; $C_3$-$C_7$ heterocyclyl; $C_2$-$C_6$ alkenyl; $C_2$-$C_6$ alkinyl; $C_3$-$C_7$ aryl; $C_3$-$C_7$ heteroaryl; $C_4$-$C_{15}$ aralkyl; $C_4$-$C_{15}$ heteroarylalkyl; $OR^{9a}$; $C(O)R^{9a}$; $C(O)OR^{9a}$; $C(O)N(R^{9a}R^{9b})$; $C(O)N(R^{9a})OR^{9b}$; $C(O)N(R^{9a})N(R^{9b}R^{9c})$; $C(R^{9a})NN(R^{9b}R^{9c})$; $C(R^{9a})NOR^{9b}$; $S(O)_2N(R^{9a}R^{9b})$; $S(O)N(R^{9a}R^{9b})$; $S(O)_2R^{9a}$; $S(O)R^{9a}$; $S(O)_2OR^{9a}$; $S(O)_2N(R^{9a})C(O)N(R^{9b}R^{9c})$; $N(R^{9a})S(O)_2N(R^{9b}R^{9c})$; $SR^{9a}$; $OC(O)R^{9a}$; $N(R^{9a})C(O)R^{9b}$; $N(R^{9a})S(O)_2R^{9b}$; $N(R^{9a})S(O)R^{9b}$; $N(R^{9a})C(O)N(R^{9b}R^{9c})$; $N(R^{9a})C(S)N(R^{9b}R^{9c})$; $N(R^{9a})C(O)OR^{9b}$; $OC(O)N(R^{9a}R^{9b})$; $C(NR^{9a})N(R^{9b})OR^{9c}$; $C(NR^{9a})N(R^{9b}R^{9c})$; $C(NR^{9a})N(R^{9b})N(R^{9c}R^{9d})$; $N(R^{9a})S(O)_2OR^{9b}$; $N(R^{9a}R^{9b})$; $C(R^{9a})NR^{9b}$; $C(NR^{9a}R^{9b})NOR^{9c}$; $C(NR^{9a}R^{9b})NOC(O)R^{9c}$; and $C(O)NR^{9a}N(R^{9b}R^{9c})$; wherein alkyl; cycloalkyl; heterocyclyl; alkenyl; alkinyl; aryl; heteroaryl; aralkyl; and heteroarylalkyl are optionally substituted by one or more $R^{13}$, which are same or different;

$R^{9a}$; $R^{9b}$; and $R^{9c}$ are independently from each other selected from H; $C_1$-$C_6$ alkyl; $C_3$-$C_7$ cycloalkyl; $C_3$-$C_7$ heterocyclyl; $C_2$-$C_6$ alkenyl; $C_2$-$C_6$ alkinyl $C_3$-$C_7$ aryl; $C_3$-$C_7$ heteroaryl; $C_4$-$C_{15}$ aralkyl; and $C_4$-$C_{15}$ heteroarylalkyl which are optionally substituted with one or more $R^{13}$, which are same or different;

$R^{13}$ is selected from halogen, CN, OH, $C_1$-$C_6$ alkyl; $OR^{13a}$; $C(O)R^{13a}$; $C(O)OR^{13a}$; $C(O)N(R^{13a}R^{13b})$; $N(R^{13a}R^{13b})$; $OC(O)R^{13a}$; $N(R^{13a})C(O)R^{13b}$; $S(O)_2N(R^{13a}R^{13b})$; $S(O)N(R^{13a}R^{13b})$; $S(O)_2R^{13a}$; $S(O)_2OR^{13a}$; $S(O)R^{13a}$; $N(R^{13a})S(O)_2N(R^{13b}R^{13c})$; $SR^{13a}$; $N(R^{13a})S(O)_2R^{13b}$; $N(R^{13a})S(O)R^{13b}$; $N(R^{13a})C(O)N(R^{13b}R^{13c})$; $N(R^{13a})C(O)OR^{13b}$; and $OC(O)N(R^{13a}R^{13b})$; wherein $C_1$-$C_6$ alkyl is optionally substituted with one or more halogen which are same or different;

$R^{13a}$; $R^{13b}$ and $R^{13c}$ are independently from each other selected from H; and $C_1$-$C_6$ alkyl; wherein $C_1$-$C_6$ alkyl is optionally substituted with one or more halogen which are same or different;

and/or solvates; hydrates; and pharmaceutically acceptable salts thereof.

Special preference is given to compounds of formula (I) wherein the two adjacent $R^8$ bound to $X^1$ and $X^2$ form the 5- or 6-membered saturated or unsaturated hydrocarbon ring or cyclic ether.

In a further preferred embodiment of compounds of formulae (Ia) to (Ic) of the present invention A is phenyl which is optionally substituted by 1 to 5 substituents R which are same or different. Compounds of this embodiment have formula

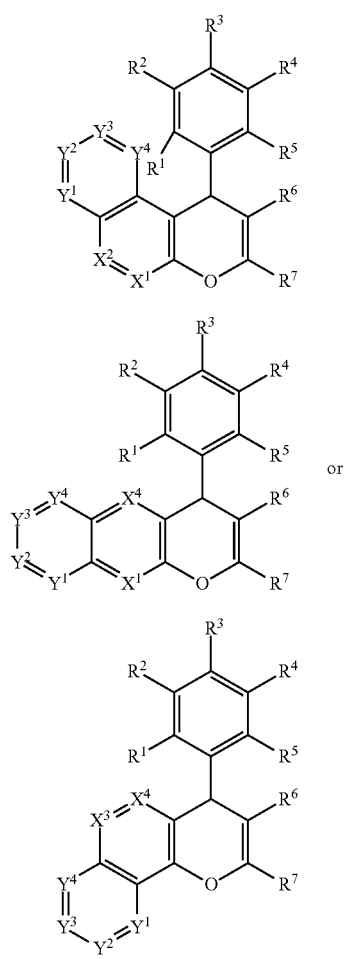

wherein the substituents are defined as above.

Special preference is given to compounds of formula (IIc) wherein the two adjacent $R^8$ bound to $X^1$ and $X^2$ form the aromatic ring.

Compounds of formulae (IIa) to (IIc) are preferred wherein at least 3 of the group of $R^1$; $R^2$; $R^3$; $R^4$ and $R^5$ are not H. More preferred $R^2$; $R^3$ and $R^4$ are not H and most preferred $R^1$ and $R^5$ are H and $R^2$; $R^3$ and $R^4$ are not H. Especially preferred are compounds of formula (II) wherein the two ring forming substituents $R^8$ are bound to $X^1$ and $X^2$ and at least 3 of the group of $R^1$; $R^2$; $R^3$; $R^4$ and $R^5$ are not H. Within this embodiment it is more preferred if $R^2$; $R^3$ and $R^4$ are not H and most preferred $R^1$ and $R^5$ are H and $R^2$; $R^3$ and $R^4$ are not H.

Especially preferred the present invention concerns compounds of formula (IIc)

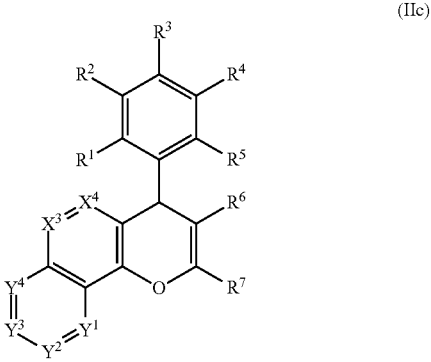

(IIc)

wherein $X^3$ and $X^4$ independently from each other are N or $CR^8$ wherein $R^8$ may be same or different;

$Y^1$, $Y^2$, $Y^3$ and $Y^4$ independently from each other are N or $CR^9$ wherein $R^9$ may be same or different and wherein up to 3 of the group $Y^1$, $Y^2$, $Y^3$ and $Y^4$ may be N;

$R^1$; $R^2$; $R^3$; $R^4$ and $R^5$ are selected from H, OH; halogen; CN; $C_1$-$C_6$ alkyl; $C_2$-$C_6$ alkenyl; $C_2$-$C_6$ alkinyl; $C_3$-$C_7$ aryl; $C_3$-$C_7$ heteroaryl; $C_4$-$C_{15}$ aralkyl; $C_4$-$C_{15}$ heteroarylalkyl; $C(O)R^{1a}$; $C(O)OR^{1a}$; $C(O)N(R^{1a}R^{1b})$; $N(R^{1a})S(O)_2OR^{1b}$; $N(R^{1a}R^{1b})$; $N(R^{1a})S(O)_2N(R^{1b}R^{1c})$; $N(R^{1a})C(O)R^{1b}$; $N(R^{1a})S(O)_2R^{1b}$; $N(R^{1a})S(O)R^{1b}$; $N(R^{1a})C(O)N(R^{1b}R^{1c})$; $N(R^{1a})C(O)OR^{1b}$; $SR^{1a}$; $S(O)_2OR^{1a}$; $S(O)_2N(R^{1a}R^{1b})$; $S(O)N(R^{1a}R^{1b})$; $S(O)_2R^{1a}$; $S(O)R^{1a}$; $OR^{1a}$; $OC(O)R^{1a}$; and $OC(O)N(R^{1a}R^{1b})$; and wherein alkyl; alkenyl, alkinyl, aryl; heteroaryl; aralkyl; and heteroarylalkyl are/is optionally substituted by one or more groups $R^{10}$ which are same or different; optionally two adjacent substituents $R^1$; $R^2$; $R^3$; $R^4$ and $R^5$ form together a 5- to 7-membered heterocyclic ring optionally substituted by one or more groups $R^{10}$ which may be same or different; and wherein at least 3 of the group of $R^1$; $R^2$; $R^3$; $R^4$; and $R^5$ are not H;

$R^{1a}$; $R^{1b}$; and $R^{1c}$ are independently from each other selected from H; $C_1$-$C_6$ alkyl; $C_3$-$C_7$ cycloalkyl; $C_3$-$C_7$ heterocyclyl; $C_2$-$C_6$ alkenyl; $C_2$-$C_6$ alkinyl; $C_3$-$C_7$ aryl; $C_3$-$C_7$ heteroaryl; $C_4$-$C_{15}$ aralkyl; and $C_4$-$C_{15}$ heteroarylalkyl; wherein alkyl; cycloalkyl; heterocyclyl; alkenyl; alkinyl; aryl; heteroaryl; aralkyl; and heteroarylalkyl are/is optionally substituted with one or more $R^{10}$ which are same or different;

$R^{10}$ is selected from halogen; CN; OH, $C_1$-$C_6$ alkyl; $OR^{10a}$; $C(O)R^{10a}$; $C(O)OR^{10a}$; $C(O)N(R^{10a}R^{10b})$; $N(R^{10a}R^{10b})$;

OC(O)R$^{10a}$; N(R$^{10a}$)C(O)R$^{10b}$; S(O)$_2$N(R$^{10a}$R$^{10b}$); S(O)N(R$^{10a}$R$^{10b}$); S(O)$_2$R$^{10a}$; S(O)R$^{10a}$; S(O)$_2$OR$^{10a}$; N(R$^{10a}$)S(O)$_2$N(R$^{10b}$R$^{10c}$); SR$^{10a}$; N(R$^{10a}$)S(O)$_2$R$^{10b}$; N(R$^{10a}$)S(O)R$^{10b}$; N(R$^{10a}$)C(O)N(R$^{10b}$R$^{10c}$); and OC(O)N(R$^{10a}$R$^{10b}$); wherein C$_1$-C$_6$ alkyl is optionally substituted with one or more halogen which are same or different;

R$^{10a}$; R$^{10b}$ and R$^{10c}$ are independently from each other selected from H; and C$_1$-C$_6$ alkyl; wherein C$_1$-C$_6$ alkyl is optionally substituted with one or more halogen which are same or different;

R$^6$ is selected from CN; C(O)R$^{6a}$; C(O)OR$^{6a}$; C(O)N(R$^{6a}$R$^{6b}$); C(NR$^{6a}$)N(R$^{6b}$R$^{6c}$); CR$^{6a}$NOR$^{6b}$; SR$^{6a}$; S(O)R$^{6a}$; S(O)$_2$R$^{6a}$; S(O)$_2$OR$^{6a}$; S(O)$_2$N(R$^{6a}$R$^{6b}$); and S(O)N(R$^{6a}$R$^{6b}$);

R$^{6a}$; R$^{6b}$; and R$^{6c}$ are independently from each other selected from H; C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl; C$_3$-C$_7$ aryl; C$_3$-C$_7$ heteroaryl; C$_4$-C$_{15}$ aralkyl; and C$_4$-C$_{15}$ heteroarylalkyl which are optionally substituted with one or more R$^{11}$, which are the same or different;

R$^{11}$ is selected from halogen; CN; OH; C$_1$-C$_6$ alkyl; OR$^{11a}$; C(O)R$^{11a}$; C(O)OR$^{11a}$; C(O)N(R$^{11a}$R$^{11b}$); N(R$^{11a}$R$^{11b}$); OC(O)R$^{11a}$; N(R$^{11a}$)C(O)R$^{11b}$; SR$^{11a}$; S(O)R$^{11a}$; S(O)$_2$R$^{11a}$; S(O)$_2$OR$^{11a}$; S(O)$_2$N(R$^{11a}$R$^{11b}$); S(O)N(R$^{11a}$R$^{11b}$); N(R$^{11a}$)S(O)$_2$N(R$^{11b}$R$^{11c}$); N(R$^{11a}$)S(O)$_2$R$^{11b}$; N(R$^{11a}$)S(O)R$^{11b}$; N(R$^{11a}$)C(O)N(R$^{11b}$R$^{11c}$); and OC(O)N(R$^{11a}$R$^{11b}$); wherein C$_1$-C$_6$ alkyl is optionally substituted with one or more R$^{18}$ which are same or different;

R$^{18}$ is selected from halogen, CN, OH; OR$^{11a}$; C(O)R$^{11a}$; C(O)OR$^{11a}$; C(O)N(R$^{11a}$R$^{11b}$); N(R$^{11a}$R$^{11b}$); OC(O)R$^{11a}$; N(R$^{11a}$)C(O)R$^{11b}$; SR$^{11a}$; S(O)R$^{11a}$; S(O)$_2$R$^{11a}$; S(O)$_2$OR$^{11a}$; S(O)$_2$N(R$^{11a}$R$^{11b}$); S(O)N(R$^{11a}$R$^{11b}$); N(R$^{11a}$)S(O)$_2$N(R$^{11b}$R$^{11c}$); N(R$^{11a}$)S(O)$_2$R$^{11b}$; N(R$^{11a}$)S(O)R$^{11b}$; N(R$^{11a}$)C(O)N(R$^{11b}$R$^{11c}$); and OC(O)N(R$^{11a}$R$^{11b}$);

R$^{11a}$; R$^{11b}$; and R$^{11c}$ are independently from each other selected from H; and C$_1$-C$_6$ alkyl; wherein C$_1$-C$_6$ alkyl is optionally substituted with one or more halogen which are the same or different;

R$^7$ is selected from H; OH; OR$^{7a}$; OC(O)R$^{7a}$; OC(O)N(R$^{7a}$R$^{7b}$); N(R$^{7a}$R$^{7b}$); N(R$^{7a}$)C(O)R$^{7b}$; N(R$^{7a}$)C(O)N(R$^{7b}$R$^{7c}$); N(R$^{7a}$)C(O)OR$^{7b}$; N(R$^{7a}$)S(O)$_2$OR$^{7b}$; N(R$^{7a}$)S(O)R$^{7b}$; N(R$^{7a}$)S(O)$_2$R$^{7b}$; N(R$^{7a}$)S(O)$_2$N(R$^{7b}$R$^{7c}$);

R$^{7a}$; R$^{7b}$; and R$^{7c}$ are independently from each other selected from H; C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl; C$_3$-C$_7$ aryl; C$_3$-C$_7$ heteroaryl; C$_4$-C$_{15}$ aralkyl; and C$_4$-C$_{15}$ heteroarylalkyl wherein alkyl; cycloalkyl; heterocyclyl; alkenyl; alkinyl; aryl; heteroaryl; heteroarylalkyl are optionally substituted with one or more R$^{12}$, which are same or different ;

R$^{12}$ is selected from halogen; CN; OH; C$_1$-C$_6$ alkyl; OR$^{12a}$; C(O)R$^{12a}$; C(O)OR$^{12a}$; C(O)N(R$^{12a}$R$^{12b}$); N(R$^{12a}$R$^{12b}$); OC(O)R$^{12a}$; N(R$^{12a}$)C(O)R$^{12b}$; S(O)$_2$N (R$^{12a}$R$^{12b}$); S(O)N(R$^{12a}$R$^{12b}$); S(O)$_2$R$^{12a}$; S(O)R$^{12a}$; S(O)$_2$OR$^{12a}$; N(R$^{12a}$)S(O)$_2$N(R$^{12b}$R$^{12c}$); SR$^{12a}$; N(R$^{12a}$)S(O)$_2$R$^{12b}$; N(R$^{12a}$)S(O)R$^{12b}$; N(R$^{12a}$)C(O)N(R$^{12b}$R$^{12c}$); N(R$^{12a}$)C(O)OR$^{12b}$; OC(O)N(R$^{12a}$R$^{12b}$); and S(O)$_2$N(R$^{11a}$)C(O)$_N$(R$^{11b}$R$^{11c}$); wherein C$_1$-C$_6$ alkyl is optionally substituted with one or more halogen which are same or different;

R$^{12a}$; R$^{12b}$ and R$^{12c}$ are independently from each other selected from H; and C$_1$-C$_6$ alkyl; wherein C$_1$-C$_6$ alkyl is optionally substituted with one or more halogen which are same or different;

R$^8$ is selected from H; OH; CN, halogen, C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl; C$_3$-C$_7$ aryl; C$_3$-C$_7$ heteroaryl; C$_4$-C$_{15}$ aralkyl; C$_4$-C$_{15}$ heteroarylalkyl; C(O)R$^{8a}$; C(O)OR$^{8a}$; C(O)N(R$^{8a}$R$^{8b}$); C(NR$^{8a}$)N(R$^{8b}$R$^{8c}$); C(R$^{8a}$)N(R$^{8b}$); OR$^{8a}$; OC(O)R$^{8a}$; OC(O)N(R$^{8a}$R$^{8b}$); SR$^{8a}$; S(O)R$^{8a}$; S(O)$_2$R$^{8a}$; S(O)$_2$OR$^{8a}$; S(O)$_2$N(R$^{8a}$R$^{8b}$); S(O)N(R$^{8a}$R$^{8b}$); S(O)$_2$N(R$^{8a}$)C(O)N(R$^{8b}$R$^{8c}$); N(R$^{8a}$)S(O)$_2$N(R$^{8b}$R$^{8c}$); N(R$^{8a}$)S(O)$_2$R$^{8b}$; N(R$^{8a}$)S(O)R$^{8b}$; N(R$^{8a}$)S(O)$_2$OR$^{8b}$; N(R$^{8a}$R$^{8b}$); N(R$^{8a}$)C(O)R$^{8b}$; N(R$^{8a}$)C(O)N(R$^{8b}$R$^{8c}$); and N(R$^{8a}$)C(S)N(R$^{8b}$R$^{8c}$); wherein alkyl; cycloalkyl; heterocyclyl; alkenyl; alkinyl; aryl; heteroaryl; aralkyl; and heteroarylalkyl are/is optionally substituted by one or more R$^{16}$, which are same or different;

R$^{8a}$ and R$^{8b}$; and R$^{8c}$ are independently from each other selected from H; C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl; C$_3$-C$_7$ aryl; C$_3$-C$_7$ heteroaryl; C$_4$-C$_{15}$ aralkyl; and C$_4$-C$_{15}$ heteroarylalkyl which are optionally substituted with one or more R$^{16}$, which are same or different;

R$^{16}$ is selected from halogen; CN; OH; C$_1$-C$_6$ alkyl; OR$^{16a}$; C(O)R$^{16a}$; C(O)OR$^{16a}$; C(O)N(R$^{16a}$R$^{16b}$); N(R$^{16a}$R$^{16b}$); OC(O)R$^{16a}$; N(R$^{16a}$)C(O)R$^{16b}$; S(O)$_2$N(R$^{16a}$R$^{16b}$); S(C)N(R$^{16a}$R$^{16b}$); S(O)$_2$R$^{16a}$; S(O)R$^{16a}$; S(O)$_2$OR$^{16a}$; N(R$^{16a}$)S(O)$_2$N(R$^{16b}$R$^{16c}$); SR$^{16a}$; N(R$^{16a}$)S(O)$_2$R$^{16b}$; N(R$^{16a}$)S(O)R$^{16b}$; N(R$^{16a}$)C(O)N(R$^{16b}$R$^{16c}$); and OC(O)N(R$^{16a}$R$^{16b}$); wherein C$_1$-C$_6$ alkyl is optionally substituted with one or more halogen which are same or different;

R$^{16a}$ and R$^{16b}$ and R$^{16c}$ are independently from each other selected from H; and C$_1$-C$_6$ alkyl; wherein C$_{1-6}$ alkyl is optionally substituted with one or more halogen which are the same or different;

R$^9$ is selected from H; OH; halogen; CN; C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl; C$_3$-C$_7$ aryl; C$_3$-C$_7$ heteroaryl; C$_4$-C$_{15}$ aralkyl; C$_4$-C$_{15}$ heteroarylalkyl; OR$^{9a}$; C(O)R$^{9a}$; C(O)OR$^{9a}$; C(O)N(R$^{9a}$R$^{9b}$); S(O)$_2$N(R$^{9a}$R$^{9b}$); S(O)N(R$^{9a}$R$^{9b}$); S(O)$_2$R$^{9a}$; S(O)R$^{9a}$; S(O)$_2$OR$^{9a}$; S(O)$_2$N(R$^{9a}$)C(O)N(R$^{9b}$R$^{9c}$); N(R$^{9a}$)S(O)$_2$N(R$^{9b}$R$^{9c}$); SR$^{9a}$; OC(O)R$^{9a}$; N(R$^{9a}$)C(O)R$^{9b}$; N(R$^{9a}$)S(O)$_2$R$^{9b}$; N(R$^{9a}$)S(O)R$^{9b}$; N (R$^{9a}$)C(O)N(R$^{9b}$R$^{9c}$); N(R$^{9a}$)C(S)N(R$^{9b}$R$^{9c}$); OC(O)N(R$^{9a}$R$^{9b}$); C(NR$^{9a}$)N(R$^{9b}$R$^{9c}$); N(R$^{9a}$)S(O)$_2$OR$^{9b}$; N(R$^{9a}$R$^{9b}$); and C(R$^{9a}$)NR$^{9b}$; wherein alkyl; cycloalkyl; heterocyclyl; alkenyl; alkinyl; aryl; heteroaryl; aralkyl; and heteroarylalkyl are optionally substituted by one or more R$^{13}$, which are same or different;

R$^{9a}$; R$^{9b}$; and R$^{9c}$ are independently from each other selected from H; C$_1$-C$_6$ alkyl; C$_3$-C$_7$ cycloalkyl; C$_3$-C$_7$ heterocyclyl; C$_2$-C$_6$ alkenyl; C$_2$-C$_6$ alkinyl C$_3$-C$_7$ aryl; C$_3$-C$_7$ heteroaryl; C$_4$-C$_{15}$ aralkyl; and C$_4$-C$_{15}$ heteroarylalkyl which are optionally substituted with one or more R$^{13}$, which are same or different;

R$^{13}$ is selected from halogen; CN; OH; C$_1$-C$_6$ alkyl; OR$^{13a}$; C(O)R$^{13a}$; C(O)OR$^{13a}$; C(O)N(R$^{13a}$R$^{13b}$); N(R$^{13a}$R$^{13b}$); OC(O)R$^{13a}$; N(R$^{13a}$)C(O)R$^{13b}$; S(O)$_2$N(R$^{13a}$R$^{13b}$); S(O)N(R$^{13a}$R$^{13b}$); S(O)$_2$R$^{13a}$; S(O)$_2$OR$^{13a}$; S(O)R$^{13a}$; N(R$^{13a}$)S(O)$_2$N(R$^{13b}$R$^{13c}$); SR$^{13a}$; N(R$^{13a}$)S(O)$_2$R$^{13b}$; N(R$^{13a}$)S(O)R$^{13b}$; N(R$^{13a}$)C(O)N(R$^{13b}$R$^{13c}$); and OC(O)N(R$^{13a}$R$^{13b}$); wherein C$_1$-C$_6$ alkyl is optionally substituted with one or more halogen which are same or different;

R$^{13a}$; R$^{13b}$ and R$^{13c}$ are independently from each other selected from H; and C$_1$-C$_6$ alkyl; wherein C$_1$-C$_6$ alkyl is optionally substituted with one or more halogen which are same or different;

and/or solvates; hydrates; and pharmaceutically acceptable salts thereof.

Within these especially preferred compounds of formula (IIc) further preferences are made as described below.

Preferred are compounds of formula (IIc) wherein at least one substituent $R^9$ is not H.

Furthermore, compounds of formula (IIc) are preferred wherein at least 1 member of the group $X^3$, $X^4$, $Y^1$, $Y^2$, $Y^3$ and $Y^4$ is N, even more preferred at least 1 member of the group $Y^1$, $Y^2$, $Y^3$ and $Y^4$ is N.

If two adjacent substituents of the group $R^1$; $R^2$, $R^3$ $R^4$; and $R^5$ are forming a 5- to 7-membered heterocycle preference is given to compounds of formula (IIc) wherein the two adjacent substituents form a 5- to 6-membered heterocycle. It is preferred if $R^2$ and $R^3$ are forming the heterocycle. The resulting heterocycle may be a monoether, a diether, a lacton or a lactam, e.g. the two adjacent substituents are together $OCH_2O$ forming a 5-membered cyclic diether.

Furthermore, compounds of formula (IIc) are preferred wherein $R^1$; $R^4$; and $R^5$ are independently from each other selected from H; $NH_2$; $NHCH_3$; $CH_2OH$; $CH_2OCH_3$; $CH_2NH_2$; $CH_2NHCH_3$; OH; $OCH_3$; Br; F; and Cl; and $R^2$ and $R^3$ are independently from each other selected from H; $NH_2$; $NHCH_3$; $CH_2OH$; $CH_2OCH_3$; $CH_2NH_2$; $CH_2NHCH_3$, OH; $OCH_3$; Br; F; and Cl; or $R^2$ and $R^3$ are together $OCH_2O$.

Furthermore, compounds of formula (IIc) are preferred wherein $R^8$ is selected from H; OH; $OR^{8a}$; $NH_2$; $NHR^{8a}$; $N(R^{8a}R^{8b})$; $CH_2OH$; $CH_2OR^{16a}$; $CH_2NH_2$; $CH_2NHR^{16a}$; $CH_2N(R^{16a}R^{16b})$; $C(O)NH_2$; $C(O)NHR^{8a}$; $C(O)N(R^{8a}R^{8b})$; $C(O)OH$; and $C(O)OR^{8a}$;

$R^{8a}$ and $R^{8b}$ are independently from each other selected from $C_1$-$C_6$ alkyl which is optionally substituted with one or more halogen which are the same or different; OH, $OR^{16a}$, $NH_2$; $NHR^{16a}$, $NR^{16a}R^{16b}$;

$R^{16a}$ and $R^{16b}$ are independently from each other selected from $C_1$-$C_6$ alkyl; wherein $C_{1-6}$ alkyl is optionally substituted with one or more halogen which are the same or different;

and $R^9$ is selected H; OH; $OR^{9a}$; $NH_2$; $NHR^{9a}$; $N(R^{9a}R^{9b})$; $CH_2OH$; $CH_2OR^{13a}$; $CH_2NH_2$; $CH_2NHR^{13a}$; $CH_2N(R^{13a}R^{13b})$; $C(O)NH_2$; $C(O)NHR^{9a}$; $C(O)N(R^{9a}R^{9b})$; $C(O)OH$; and $C(O)OR^{9a}$;

$R^{9a}$ and $R^{9b}$ are independently from each other selected from $C_1$-$C_6$ alkyl which is optionally substituted with one or more halogen which are the same or different; OH, $OR^{13a}$, $NH_2$; $NHR^{13a}$, $NR^{13a}R^{13b}$;

$R^{13a}$ and $R^{13b}$ are independently from each other selected from $C_1$-$C_6$ alkyl; wherein $C_{1-6}$ alkyl is optionally substituted with one or more halogen which are the same or different.

Even more preferred are the following embodiments of the present invention concerning the general and the especially preferred compounds of formula (IIc) as defined above wherein $R^6$ is CN and $R^7$ is $NH_2$;
at least 1 member of the group $Y^1$, $Y^2$, $Y^3$ and $Y^4$ is N;
$Y^1$ is N, $R^7$ is $NH_2$ and $R^6$ is CN;
$Y^1$ is N and $Y^2$ is $CR^9$ with $R^9$ is not H;
$Y^1$ is N, $Y^2$ is $CR^9$ with $R^9$ is not H, and $Y^3$ and $Y^4$ are $CR^9$;
$Y^1$ is N, $Y^2$ and $Y^4$ are $CR^9$ with $R^9$ is not H and $Y^3$ is $CR^9$;
$Y^1$ is N and $Y^2$ is $CR^9$ with $R^9$ is not H and $R^6$ is CN;
$Y^1$ is N and $Y^2$ is $CR^9$ with $R^9$ is not H and $R^7$ is $NH_2$;
$Y^1$ is N and $Y^2$ is $CR^9$ with $R^9$ is not H; $R^6$ is CN and $R^7$ is $NH_2$;
$Y^1$ and $Y^3$ are N, $R^6$ is CN and $R^7$ is $NH_2$, and $Y^2$ and $Y^4$ are $CR^9$ with $R^9$ is not H;
$Y^1$ and $Y^3$ are N, $R^6$ is CN and $R^7$ is $NH_2$, $Y^2$ is $CR^9$ with $R^9$ is not H, and $Y^4$ is $CR^9$;

$Y^1$ and $Y^3$ are N, $R^6$ is CN and $R^7$ is $NH_2$; $Y^2$ is $CR^9$, and $Y^4$ is $CR^9$ with $R^9$ is not H;
$Y^2$ and $Y^4$ are N, $R^6$ is CN and $R^7$ is $NH_2$; $Y^1$ and $Y^3$ are $CR^9$ with $R^9$ is not H;
$Y^2$ and $Y^4$ are N, $R^6$ is CN and $R^7$ is $NH_2$; $Y^1$ is $CR^9$ with $R^9$ is not H; $Y^3$ is $CR^9$;
$Y^2$ and $Y^4$ are N, $R^6$ is CN and $R^7$ is $NH_2$; $Y^1$ is $CR^9$; $Y^3$ is $CR^9$ with $R^9$ is not H;
$Y^1$ and $Y^4$ are N, $R^6$ is CN and $R^7$ is $NH_2$, and $Y^2$ and $Y^3$ are $CR^9$ with $R^9$ is not H;
$Y^1$ and $Y^4$ are N, $R^6$ is CN and $R^7$ is $NH_2$, $Y^2$ is $CR^9$ with $R^9$ is not H, and $Y^3$ is $CR^9$;
$Y^1$ and $Y^4$ are N, $R^6$ is CN and $R^7$ is $NH_2$, $Y^2$ is $CR^9$, and $Y^3$ is $CR^9$ with $R^9$ is not H;
$Y^1$ and $X^3$ are N, $R^6$ is CN and $R^7$ is $NH_2$, $Y^2$, $Y^3$, $Y^4$ are $CR^9$, and $X^4$ is $CR^8$; or
$Y^1$ and $X^4$ are N, $R^6$ is CN and $R^7$ is $NH_2$, $Y^2$, $Y^3$, $Y^4$ are $CR^9$, and $X^3$ is $CR^8$;

and/or solvates; hydrates; and pharmaceutically acceptable salts thereof.

Within all embodiments described it is more preferred if $R^2$; $R^3$ and $R^4$ are not H and most preferred if $R^1$ and $R^5$ are H and $R^2$; $R^3$ and $R^4$ are not H.

In a further preferred embodiment the two adjacent $R^8$ form together a cyclic 5-membered substituted or unsubstituted diether resulting in compounds of formulae

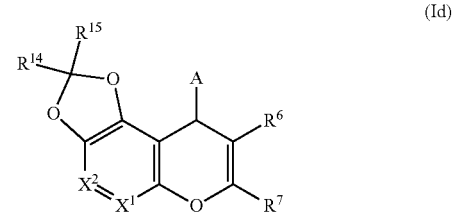

(Id)

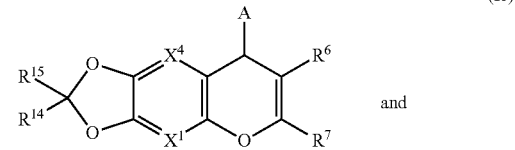

(Ie)

and

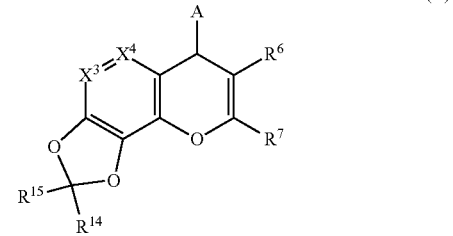

(If)

wherein
$R^{14}$ and $R^{15}$ are independently from each other selected from H; halogen; CN; $C_1$-$C_6$ alkyl; $C_3$-$C_7$ cycloalkyl; $C_3$-$C_7$ heterocyclyl; $C_2$-$C_6$ alkenyl; $C_2$-$C_6$ alkinyl; $C_3$-$C_7$ aryl; $C_3$-$C_7$ heteroaryl; $C_4$-$C_{15}$ aralkyl; $C_4$-$C_{15}$ heteroarylalkyl; $C(O)R^{14a}$; $C(O)OR^{14a}$; $C(O)N(R^{14a}R^{14b})$; $C(R^{14a})NR^{14b}$; and $C(R^{14a})NN(R^{14b}R^{14c})$; wherein allyl; alkenyl; alkinyl; cycloalkyl; heterocyclyl; aryl; heteroaryl; aralkyl; and heteroarylalkyl are optionally substituted by one or more groups $R^{17}$ which are same or different;
$R^{14a}$; $R^{14b}$; and $R^{14c}$ are independently from each other selected from H; $C_1$-$C_6$ alkyl; $C_3$-$C_7$ cycloalkyl; $C_3$-$C_7$ heterocyclyl; $C_2$-$C_6$ alkenyl; $C_2$-$C_6$ alkinyl; $C_3$-$C_7$ aryl;

$C_3$-$C_7$ heteroaryl; $C_4$-$C_{15}$ aralkyl; and $C_4$-$C_{15}$ heteroarylalkyl; wherein alkyl; cycloalkyl; heterocyclyl; alkenyl; alkinyl; aryl; heteroaryl; aralkyl; and heteroarylalkyl are optionally substituted with one or more $R^{17}$ which are the same or different;

$R^{17}$ is selected from halogen, CN, OH, $C_1$-$C_6$ alkyl; $OR^{17a}$; $C(O)R^{17a}$; $C(O)OR^{17a}$; $C(O)N(R^{17a}R^{17b})$; $N(R^{17a}R^{17b})$; $OC(O)R^{17a}$; $N(R^{17a})C(O)R^{17b}$; $S(O)_2N(R^{17a}R^{17b})$; $S(O)N(R^{17a}R^{17b})$; $S(O)_2R^{17a}$; $S(O)R^{17a}$; $N(R^{17a})S(O)_2N(R^{17b}R^{17c})$; $SR^{17a}$; $N(R^{17a})S(O)_2R^{17b}$; $S(O)_2OR^{17a}$; $N(R^{17a})S(O)R^{17b}$; $N(R^{17a})C(O)N(R^{17b}R^{17c})$; $N(R^{17a})C(O)OR^{17b}$; and $OC(O)N(R^{17a}R^{17b})$; wherein $C_1$-$C_6$ alkyl is optionally substituted with one or more halogen which are the same or different;

$R^{17a}$; $R^{17b}$ and $R^{17c}$ are independently from each other selected from H; and $C_1$-$C_6$ alkyl; wherein $C_{1-6}$ alkyl is optionally substituted with one or more halogen which are the same or different;

the definitions of the further substituents are given above;

and/or solvates; hydrates; and pharmaceutically acceptable salts thereof.

Special preference is given to compounds of formula (If) wherein the two adjacent $R^8$ bound to $X^1$ and $X^2$ form the cyclic ether.

In a further preferred embodiment of formulae (Id) to (If) of the present invention A is phenyl which is optionally substituted by 1 to 5 substituents R resulting in compounds of formulae

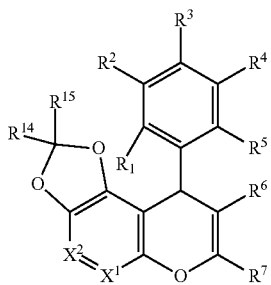

(IId)

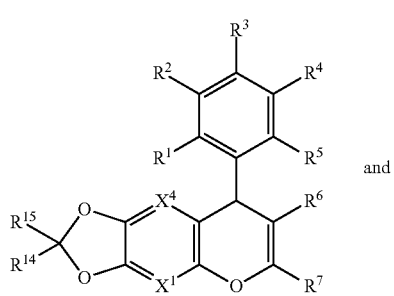

(IIe)

and

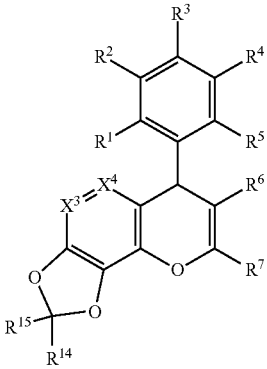

(IIf)

wherein the substituents are defined as above.

Within this embodiment it is even more preferred if at least 3 of the group of $R^1$; $R^2$; $R^3$; $R^4$ and $R^5$ are not H, particularly preferred $R^2$; $R^3$ and $R^4$ are not H and most preferred $R^1$ and $R^5$ are H and $R^2$; $R^3$ and $R^4$ are not H.

Another preferred embodiment of the invention concerns the compounds of formula (II) and (IIa) to (IIf), wherein at least 3 of the group of $R^1$; $R^2$; $R^3$; $R^4$ and $R^5$ are not H, particularly preferred $R^2$; $R^3$ and $R^4$ are not H, and the further substituents are defined as above, and/or solvates; hydrates; and pharmaceutically acceptable salts thereof.

Special preference is given to compounds of formula (IIf) wherein the two adjacent $R^8$ bound to $X^1$ and $X^2$ form the cyclic ether.

According to the invention the solvates; hydrates; and/or pharmaceutically acceptable salts of all compounds of formulae (I), (Ia) to (If), (II) and (IIa) to (IIf) described above are included herein.

Some of the compounds of the invention and/or salts or esters thereof will exist in different stereo isomeric forms. All of these forms are subjects of the invention.

Described below are exemplary salts of the compounds according to the invention which are included herein. The list of the different salts stated below is not meant to be complete and limiting.

Compounds according to the invention which contain one or more acidic groups can be used according to the invention, e.g. as their alkali metal salts, alkaline earth metal salts or ammonium salts. More precise examples of such salts include sodium salts, potassium salts, calcium salts, magnesium salts or salts with ammonia or organic amines such as, e.g. ethylamine, ethanolamine, triethanolamine or amino acids.

Compounds according to the invention which contain one or more basic groups, i.e. groups which can be protonated, can be used according to the invention in the form of their addition salts with inorganic or organic acids.

Examples for suitable acids include hydrogen chloride, hydrogen bromide, phosphoric acid, sulfuric acid, nitric acid, methanesulfonic acid, p-toluenesulfonic acid, napthalenedisulfonic acid, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid and other acids known to a person skilled in the art.

Compounds according to the invention which contain several basic groups can simultaneously form different salts.

If a compound according to the invention simultaneously contains acidic and basic groups in the molecule, the invention also includes, in addition to the salt forms mentioned, inner salts or betaines.

The respective salts of the compounds according to the invention can be obtained by customary methods which are known to the person skilled in the art, for example by contacting these with an organic or inorganic acid or base in a solvent or dispersant, or by anion exchange or cation exchange with other salts.

The term "pharmaceutically acceptable" means approved by a regulatory agency such as the EMA (Europe) and/or the FDA (US) and/or any other national regulatory agency for use in animals, preferably in humans.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying Wnt signalling pathway modulating activity of a compound according of the invention in any suitable manner, such as any suitable in vitro assay.

The present invention furthermore includes all solvates of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention.

The present invention furthermore includes the metabolites of the compounds according to the invention.

The term "metabolites" refers to all molecules derived from any of the compounds according to the invention in a cell or organism, preferably mammal.

Preferably the term "metabolites" relates to molecules which differ from any molecule which is present in any such cell or organism under physiological conditions.

The structure of the metabolites of the compounds according to the invention will be obvious to any person skilled in the art, using the various appropriate methods.

The compounds of the invention may be prepared by the three component reaction of a substituted or unsubstituted aromatic or heteroaromatic monocyclic or polycyclic aldehyde (e.g. benzaldehyde, pyridinecarbaldehydes, imidazolecarbaldehyde, furancarbaldehydes, benzofurancarbaldehydes, indolecarbaldehydes, pyrazolecarbaaldehydes, oxazolecarbaldehydes and their derivatives), an OH-substituted aromate or heteroaromate, which may be further substituted (e.g. 1-naphtol, hydroxypyrimidine, hydroxypyridine, hydroxyquinaldine, hydroxyquinoline, hydroxyisoquinoline, sesamol and their derivatives) and malonodinitrile or ethylcyanoacetate and the like in a solvent like toluene, alcohols or dimethylformamide. The compounds obtained may be modified by further reaction steps.

Further methods for the preparation of the inventive compounds are known to the person skilled in the art.

Depending on the circumstances of the individual case, in order to avoid side reactions during the synthesis of a compound of the general formulae (I), (Ia) to (If), (II) and (IIa) to (IIf), it can be necessary or advantageous to temporarily block functional groups by introducing protective groups and to deprotect them in a later stage of the synthesis, or to introduce functional groups in the form of precursor groups and at a later stage to convert them into the desired functional groups. Suitable synthetic strategies, protective groups and precursor groups are known to the person skilled in the art.

If desired, the compounds of the formulae (I), (Ia) to (If), (II) and (IIa) to (IIf) can be purified by customary purification procedures, for example by recrystallization or chromatography. The starting materials for the preparation of the compounds of the formulae (I), (Ia) to (If), (II) and (IIa) to (IIf) are commercially available or can be prepared according to or analogously to literature procedures.

The compounds of the invention may serve as a basis for the preparation of the other compounds according to the invention by several methods well known by the person skilled in the art.

The present invention relates to the discovery that signal transduction pathways regulated by Wnt can be inhibited, at least in part, by compounds of formulae (I), (Ia) to (If), (II), (IIa) to (IIf). As set out in more detail below, these compounds can inhibit proliferation of tumor cells having Wnt modulated activity. Therefore, the compounds according to the invention are suited for modulating the Wnt signalling pathway.

As used herein, the term "modulating the Wnt signalling pathway" refers to an effect on the series of events that occur when Wnt proteins bind to cell-surface receptors of the frizzled family resulting in an accumulation of beta-catenin in the cell cytoplasm that reaches the nucleus of a cell, and consequently, the Wnt target genes are expressed. The Wnt signalling pathway may be modulated by direct or indirect modulation.

"Direct modulation" according to the present invention means an interaction of the inventive compounds with proteins directly involved in the Wnt signalling pathway leading to an increase or decrease of the expression of the Wnt target genes.

"Indirect modulation" according to the present invention means an increase or decrease of the expression of the Wnt target genes without a direct interaction of the inventive compound with the components involved in the Wnt signalling pathway. Examples for the indirect modulation of the Wnt signalling pathway are tankyrase-inhibitors and calcium regulators like siperone, thapsigargine and iononycine.

Inhibition of tankyrases stabilizes one protein of the Wnt signalling pathway (axin), which inhibits the Wnt signalling pathway Inhibition of the decomposition of axin leads to an increase of axin and in turn to the inhibition of the Wnt signalling pathway (Huang et al., Nature 461, pp. 614 to 620 (2009))

By increasing the intracellular calcium level the Wnt protein beta-catenin is transferred out of the nucleus and decomposes. This inhibits a beta-catenin-mediated Wnt signalling pathway activity without inhibiting a Wnt protein directly, too ((Lu et al., BMC Pharm, 2009 9:13 (doi: 10.1186/1471-2210-9-13) and Li et al., PNAS 99, pp. 13254 to 13259 (2002)).

While not wishing to be bound by any particular theory, the activation of a receptor may be the mechanism by which these compounds act as described in US 2007/0219257 A1. For example, the compounds could affect the activity of a Wnt frizzled receptor. Alternatively, the compounds could affect the activity of the serine/threonine kinase GSK3β, which is involved in the down regulation of β-catenin. The compounds could also affect the activity of the APC gene. In the absence of Wnt signal, the APC protein functions to foster degradation of β-catenin and prevent its nuclear entry. Wnt stimulation, loss of APC protein function, or of its associated partner Axin, all lead to stabilization of and concentration of β-catenin in the nucleus, which then can act as a transcriptional co-activator by associating with the Tcf/LEF family of transcription factors. APC in complex with Axin and other proteins target β-catenin for proteasomal degradation by scaffolding the association between β-catenin and kinases whose action lead to β-catenin ubiquitinylation; this action is abrogated by recruitment of the degradation complex to the membrane upon Wnt activation of a receptor complex that includes Frizzled (Fz), a relative of Smo, and LRP5/6. The pathway can also be activated by mutations of β-catenin that render it resistant to degradation.

Or, for example, the compounds could alter the activity of Dishevelled, which is a positive mediator of Wnt signaling. For example, the ability of these compounds to inhibit proliferation of cells may be due to the ability of such molecules to interact with Wnt, or at least to interfere with the ability of those proteins to activate a Wnt-mediated signal transduction pathway. Signal transduction antagonists of different structures, even ones that bind to the same protein in the signaling pathways, may act in slightly different ways. Accordingly, even if a particular condition caused or contributed to by aberrant or unwanted activation of the Wnt pathway shows little response to treatment by one of the antagonists disclosed herein, another of the antagonists disclosed herein may nonetheless be efficacious.

One embodiment of the present invention includes the use of compounds of formulae (I), (Ia) to (If), (II) and (IIa) to (IIf) that agonize inhibition of Wnt signaling, such as by inhibiting activation of Wnt downstream components of the signaling pathway, in the regulation of repair and/or functional performance of a wide range of cells, tissues and organs, including normal cells, tissues, and organs. For instance, the compounds of formulae (I), (IIa) to (IIf), (II) and (IIa) to (IIf) have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Moreover, the compounds of formula (I) can be applied to cells that are provided in culture (in vitro), or on cells in a whole animal (in vivo).

Another embodiment of present invention includes the use of compounds of formulae (I), (Ia) to (If), (II) and (IIa) to (IIf) which antagonize activity of the Wnt pathway resulting in the regulation of repair and/or functional performance of a wide range of cells, tissues, and organs. For instance, the inventive compounds have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. The compounds of the invention can be applied on cells which are provided in culture (in vitro), or on cells in a whole animal (in vivo).

The term "agonist" refers to an agent or analog that binds productively to a receptor or other mediators of the signaling pathway and mimics the biological activity. The term "antagonist" refers to an agent that binds to receptors or other mediators of the signaling pathway and inhibits the biological activity. Thus, an antagonist potentiates or recapitulates, for example, the bioactivity of Axin, such as to repress transcription of target genes. The term "Wnt antagonist" as used herein refers not only to any agent that may act by directly inhibiting the normal function of the Wnt proteins, but also to any agent that inhibits the Wnt signaling pathway, and thus antagonizes the function of Wnt. The term "Wnt agonist" likewise refers to an agent which activates or stabilizes the bioactivity of Wnt, such as to increase transcription of target genes.

It is preferred according to the invention to decrease the activity of the Wnt signalling pathway and/or to inhibit the Wnt signalling pathway. Preferably the compounds of the invention are used as Wnt antagonists and used to regulate e.g. proliferation or other biological consequences of mis-expression of Wnt.

As outlined above, an elevated beta-catenin level in the nucleus of a cell is a hallmark of an aberrant activation of the Wnt signalling pathway and plays a major role in the development of several kinds of cancer. The measurement of the beta-catenin level in the nucleus of the cell may be carried out according procedures known to the person skilled in the art. The measurement of the Tcf-beta-catenin complex level by means of 6×Tcf-luciferase is described below in the experiments. The use of a compound for modulating the Wnt signalling pathway resulting in a decrease of the relative amount of Tcf-beta-catenin complex in the nucleus of a cell is preferred.

Modulating the Wnt signalling pathway can be carried out by contacting a cell with a compound according to the invention. In one embodiment of the invention, said modulation is performed in vitro or in cell culture. As known to the person skilled in the art, several in vitro and cell culture assays are available.

According to a further embodiment of the invention the modulation can be performed in animals such as mammals. Animal subjects to which the invention is applicable extend to both domestic animals and livestock, raised either as pets or for commercial purposes. Exemplary mammals are mice, rats, guinea pigs, monkeys, dogs and cats. The modulation can also be carried out in humans.

The invention also relates to the compounds (I), (Ia) to (If), (II) and (IIa) to (IIf) of the invention for use as a medicament. The compounds are as defined above; furthermore the embodiments as described below with respect to the use as medicament, e.g. formulation, application and combination, also apply to this aspect of the invention. The pharmaceutical preparation or medicaments comprising the compounds of formulae (I), (Ia) to (If), (II) and (IIa) to (IIf) can be effective for both human and animal subjects. Animal subjects to which the invention is applicable extend to both domestic animals and livestock, raised either as pets or for commercial purposes. Examples are dogs, cats, cattle, horses, sheep, hogs, and goats.

The invention further relates to the use of the compounds of formulae (I), (Ia) to (If), (II) and (IIa) to (IIf) for modulating the Wnt signalling pathway.

The compounds according to the invention are suited for the use for the preparation of a medicament for modulating the Wnt signalling pathway. The present invention provides pharmaceutical preparations or medicaments comprising a compound such as described herein, formulated in an amount sufficient to regulate, in vivo, Wnt pathway, e.g., proliferation or other biological consequences of mis-expression of Wnt.

The invention further relates to the use of a compound according to the invention for the preparation of a medicament for the treatment of a disorder or disease associated with an aberrant activation of Wnt signalling in a mammal and to compounds of the invention for the treatment of a disorder or disease associated with an aberrant activation of Wnt signalling in a mammal. The disorders or diseases associated with the Wnt signalling pathway are for example cell-proliferative disorders, rheumatoid arthritis, diseases connected with aberrant bone density and Dupuytren disease (superficial fibromatosis).

A cell proliferation disorder is a disorder which is connected with some degree of abnormal cell proliferation. Especially, cell-proliferation disorders are important for the development of cancer. A further cell-proliferation disorder is proliferative skin disorders which are marked by unwanted or aberrant proliferation of cutaneous tissue, for example X-linked ichtyosis, psoriasis, atopic dermatitis, allergic contact dermatitis, epidermolytic hyperkeratosis and seborrheic dermatitis. In one preferred aspect, the invention relates to the use of the compounds according to the invention for the preparation of a medicament for the treatment of cancer or proliferative skin disorder.

The Wnt-signalling pathway is also believed to be involved in the maintenance of stem or progenitor cells in a growing list of adult tissues that includes e.g. skin, blood, gut, prostate, muscle and the nervous system. Stem and progenitor cells are important for cell regeneration and consequently for aging and aging related processes. Therefore, the compounds of the invention are useable for the preparation of a medicament for the treatment of aging and age-related disorders and/or diseases.

The compounds of the invention are especially suitable for the use for the preparation of a medicament for the treatment of cancer wherein the cancer is a member of the group multiple myeloma, colon cancer, breast cancer, gastritic cancer, colorectal cancer, lung cancer, prostate cancer, ovarian cancer, bladder cancer, liver cancer, uterine cancer, kidney cancer, leukaemia, gliomas, basal cell carcinoma, rhabdomyosarcoma, mesothelioma, osteosarcoma, medulloblastomas and other primary CNS malignant neuroectodermal tumors.

Possible disorders or diseases which may be treated by administering a medicament prepared from the compounds for formulae (I), (Ia) to (If), (II) and (IIa) to (IIf) are described in detail in US 2007/0219257 A1. Accordingly the compounds of the present invention are applicable to cell culture techniques wherein, whether for genetic or biochemical reasons, the cells have a Wnt receptor. Alternatively, a compound of formulae (I), (Ia) to (If), (II) and (IIa) to (IIf) may be employed in a related method directed towards cells which have a Wnt receptor. In vitro neuronal culture systems have proven to be fundamental and indispensable tools for the study of neural development, as well as the identification of neurotrophic factors such as nerve growth factor (NGF), ciliary trophic factors (CNTF), and brain derived neurotrophic factor (BDNF). One use of the compounds of formulae (I), (Ia) to (If), (II) and (IIa) to (IIf) may be in cultures of neuronal stem cells, such as in the use of such cultures for the generation of new neurons and glia. In such embodiments of the subject method, the cultured cells can be contacted with an aromatic compound of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motorneurons: Such neuronal cultures can be used as convenient assay systems as well as sources of implantable cells for therapeutic treatments.

In another embodiment, the compounds of the invention can be used in the treatment of neoplastic or hyperplastic transformations such as may occur in the central nervous system. For instance, the compounds can be utilized to cause such transformed cells to become either post-mitotic or apoptotic. The compounds may, therefore, be used as part of a treatment for, e.g., malignant gliomas, meningiomas, medulloblastomas, neuroectodermal tumors, and ependymomas.

In another embodiment, the compounds of the invention can be used as part of a treatment regimen for malignant medulloblastoma and other primary CNS malignant neuroectodermal tumors.

In certain embodiments, the compounds of the invention are used as part of treatment program for medulloblastoma. Medulloblastoma, a primary brain tumor, is the most common brain tumor in children. A medulloblastoma is a primitive neuroectodermal tumor (PNET) arising in the posterior fossa. Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MM has largely replaced myelography for this purpose, and CSF cytology is obtained postoperatively as a routine procedure.

In other embodiments, the compounds of formulae (I), (Ia) to (If), (II) and (IIa) to (IIf) are used as part of a treatment program for hepatocellular carcinoma. Hepatocellular carcinoma is a form of cancer that arises from hepatocytes, the major cell type of the live, and is one of the most common tumors involving mutations in the Wnt pathway.

In other embodiments, the compounds of formulae (I), (Ia) to (If), (II) and (IIa) to (IIf) are used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes.

Yet another aspect of the present invention concerns the observation in the art that Wnt is involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising one or more of the inventive compounds can also be utilized for both cell culture and therapeutic uses involving generation and maintenance of non-neuronal tissue.

In one embodiment, the present invention makes use of the discovery that Wnt is apparently involved in controlling the development of stem cells responsible for formation of the digestive tract, liver, lungs, and other organs which derive from the primitive gut. Therefore, for example, compounds of formulae (I), (Ia) to (If), (II) and (IIa) to (IIf) can be employed for regulating the development and maintenance of an artificial liver which can have multiple metabolic functions of a normal liver. In an exemplary embodiment, the compounds of formulae (I), (Ia) to (If), (II) and (IIa) to (IIf) can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of inventive compounds can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the compounds of formulae (I), (Ia) to (If), (II) and (IIa) to (IIf) can be employed therapeutically to regulate such organs after physical, chemical or pathological insult. For instance, therapeutic compositions comprising the compounds of formulae (I), (Ia) to (If), (II) and (IIa) to (IIf) can be utilized in liver repair subsequent to a partial hepatectomy.

In the context of the present invention, it is contemplated therefore that the inventive compounds can be used to control or regulate the proliferation and/or differentiation of pancreatic tissue both in vivo and in vitro.

There are a wide variety of pathological cell proliferative and differentiative conditions for which the compounds of the present invention may provide therapeutic benefits, with the general strategy being, for example, the correction of aberrant insulin expression, or modulation of differentiation. More generally, however, the present invention relates to the use of the compounds of formulae (I), (Ia) to (If), (II) and (IIa) to (IIf) for inducing and/or maintaining a differentiated state, enhancing survival and/or affecting proliferation of pancreatic cells, by contacting the cells with the subject inhibitors. For instance, it is contemplated by the invention that, in light of the apparent involvement of Wnt in the formation of ordered spatial arrangements of pancreatic tissues, the compounds of the invention could be used as part of a technique to generate and/or maintain such tissue both in vitro and in vivo. For instance, modulation of the function of Wnt can be employed in both cell culture and therapeutic uses involving generation and maintenance β-cells and possibly also for non-pancreatic tissue, such as in controlling the development and maintenance of tissue from the digestive tract, spleen, lungs, colon, and other organs which derive from the primitive gut.

In an exemplary embodiment, the compounds of the invention can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. To the extent that aberrant Wnt signaling may be indicated in disease progression, the compounds of the invention can be used to enhance regeneration of the tissue after anti-tumor therapy.

Moreover, manipulation of Wnt signaling properties at different points may be useful as part of a strategy for reshaping/repairing pancreatic tissue both in vivo and in vitro. In one embodiment, the present invention makes use of the apparent involvement of Wnt in regulating the development of pancreatic tissue. In general, the compounds of the invention can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering Wnt, can provide a means for more carefully controlling the characteristics of a cultured tissue. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature β-cells can be observed. By utilizing the compounds of the invention, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of Wnt function to affect tissue differentiation can be utilized as a means of maintaining graft viability.

Many other tumors may, based on evidence such as involvement of the Wnt pathway in these tumors, or detected expression of Wnt or its receptors in these tissues during development, be affected by treatment with the compounds of the invention.

In still another embodiment of the present invention, compositions comprising one or more of the compounds of the invention can be used in the in vitro generation of skeletal tissue, such as from skeletogenic stem cells, as well as the in vivo treatment of skeletal tissue deficiencies. The present invention particularly contemplates the use of compounds of the invention to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g. whether as a result of surgical intervention, removal of tumor, ulceration, implant, fracture, or other traumatic or degenerative conditions.

For instance, the compounds of the invention can be used as part of a regimen for restoring cartilage function to a connective tissue. They are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a laxation of a joint by a torn ligament, malignment of joints, bone fracture, or by hereditary disease. The compounds of the invention may also be useful for remodeling cartilage matrix, such as in plastic or reconstructive surgery, as well as periodontal surgery. They may also be applied to improving a previous reparative procedure, for example, following surgical repair of a meniscus, ligament, or cartilage. Furthermore, it may prevent the onset or exacerbation of degenerative disease if applied early enough after trauma.

One embodiment of the present invention relates to the treating of the afflicted connective tissue with a therapeutically effective amount of compounds of the invention to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the compounds of the invention can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the compounds of the invention can be used to treat a degenerative disorder of a knee, such as which might be the result of traumatic injury (e.g., a sports injury or excessive wear) or osteoarthritis. The compounds of the invention may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the compounds of the invention in the field of cartilage transplantation and prosthetic device therapies. However, problems arise, for instance, because the characteristics of cartilage and fibrocartilage vary between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the compounds of the invention can be used to particularly address this problem, by helping to adaptively control the implanted cells in the new environment and effectively resemble hypertrophic chondrocytes of an earlier developmental stage of the tissue.

In similar fashion, the compounds of the invention can be applied to enhancing both the generation of prosthetic cartilage devices and to their implantation. The need for improved treatment has motivated research aimed at creating new cartilage that is based on collagen-glycosaminoglycan templates (Stone et al., Clin. Orthop. Relat. Red 252:129 (1990)), isolated chondrocytes (Grande et al., J. Orthop. Res. 7:208 (1989); and Takigawa et al., Bone Miner 2:449 (1987)), and chondrocytes attached to natural or synthetic polymers (Walitani et al., J. Bone Jt. Surg. 71B:74 (1989); Vacanti et al., Plast. Reconstr. Surg. 88:753 (1991); von Schroeder et al. J. Biomed. Mater. Res. 25:329 (1991); Freed et al., J. Biomed. Mater. Res. 27:11 (1993); and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the invention, the implants are contacted with a subject aromatic compound during certain stages of the culturing process in order to manage the rate of differentiation of chondrocytes and the formation of hypertrophic chrondrocytes in the culture.

In another embodiment, the implanted device is treated with a compound of formulae (I), (Ia) to (If), (II) and (IIa) to (IIf) in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the compounds of the invention are used to enhance attachment of prosthetic devices. To illustrate, the compounds of the invention can be used in the implantation of a periodontal prosthesis, wherein the treatment of the surrounding connective tissue stimulates formation of periodontal ligament about the prosthesis.

In other embodiments, the compounds of the invention can be employed as part of a regimen for the generation of bone (osteogenesis) at a site in the animal where such skeletal tissue is deficient. For instance, administration of a compound of the present invention can be employed as part of a method for regulating the rate of bone loss in a subject. For example, preparations comprising subject compounds can be employed, for example, to control endochondral ossification in the formation of a "model" for ossification.

The compounds of the invention also have wide applicability to the treatment or prophylaxis of disorders afflicting epithelial tissue, as well as in cosmetic uses. In general, this includes a step of administering to an animal an amount of a subject aromatic compound effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the compounds of the invention, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, a lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of a compound of formulae (I), (Ia) to (If), (II) and (IIa) to (IIf) can reduce the abnormal proliferation and differentiation of the affected epithelium, helping to reduce the severity of subsequent inflammatory events.

The compounds of the invention and compositions thereof can also be used to treat wounds resulting from dermatological diseases, such as lesions resulting from autoimmune disorders such as psoriasis. Atopic dermititis refers to skin trauma resulting from allergies associated with an immune response caused by allergens such as pollens, foods, dander, insect venoms and plant toxins.

In other embodiments, antiproliferative preparations of subject compounds can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intra-capsular extraction are lower incidence of aphakic cystoid macular edema and retinal detachment. Extracapsular extraction is also required for implantation of posterior chamber type intraocular lenses which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells which remain after extracapsular lens extraction. These cells proliferate to cause Sommerling rings, and along with fibroblasts which also deposit and occur on the posterior capsule, cause opacification of the posterior capsule, which interferes with vision. Prevention of after-cataract would be preferable to treatment. To inhibit secondary cataract formation, the present invention provides a means for inhibiting proliferation of the remaining lens epithelial cells. For example, such cells can be induced to remain quiescent by instilling a solution containing a preparation of a compound of formulae (I), (Ia) to (If), (II) and (IIa) to (IIf) into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The compounds of the invention can also be used in the treatment of corneopathies marked by corneal epithelial cell proliferation, as for example in ocular epithelial disorders such as epithelial downgrowth or squamous cell carcinomas of the ocular surface.

Yet another aspect of the present invention relates to the use of the compounds of the invention to control hair growth. Hair is basically composed of keratin, a tough and insoluble protein; its chief strength lies in its disulphide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the compounds of the invention can be employed as a way of reducing the growth of human hair as opposed to its conventional removal by cutting, shaving, or depilation. For instance, the present method can be used in the treatment of trichosis characterized by abnormally rapid or dense growth of hair, e.g. hypertrichosis. In an exemplary embodiment, subject compounds can be used to manage hirsutism, a disorder marked by abnormal hairiness. The compounds of the invention can also provide a process for extending the duration of depilation.

Moreover, because a subject compound will often be cytostatic to epithelial; cells, rather than cytotoxic, such agents can be used to protect hair follicle cells from cytotoxic agents which require progression into S-phase of the cell-cycle for efficacy, e.g. radiation-induced death. Treatment by the compounds of the invention can provide protection by causing the hair follicle cells to become quiescent, e.g., by inhibiting the cells from entering S phase, and thereby preventing the follicle cells from undergoing mitotic catastrophe or programmed cell death. For instance, compounds of the invention can be used for patients undergoing chemo- or radiation-therapies which ordinarily result in hair loss. By inhibiting cell-cycle progression during such therapies, the subject treatment can protect hair follicle cells from death which might otherwise result from activation of cell death programs. After the therapy has concluded, the administration of compounds of the invention can be stopped with concomitant relief of the inhibition of follicle cell proliferation.

The compounds of the invention can also be used in the treatment of folliculitis, such as folliculitis decalvans, folliculitis ulerythematosa reticulata or keloid folliculitis. For example, a cosmetic preparation of a compound of formulae (I), (Ia) to (If), (II) and (IIa) to (IIf) can be applied topically in the treatment of pseudofolliculitis, a chronic disorder occurring most often in the submandibular region of the neck and associated with shaving, the characteristic lesions of which are erythematous papules and pustules containing buried hairs.

In another aspect of the invention, the compounds of the invention can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example basal cell carcinoma or squamous cell carcinoma. The compounds of the invention can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or non-inflammatory components. To illustrate, therapeutic preparations of an inventive compound, e.g., which promotes quiescense or differentiation, can be used to treat varying forms of psoriasis, be they cutaneous, mucosal orungual. Psoriasis, as described above, is typically characterized by epidermal keratinocytes which display marked proliferative activation and differentiation along a "regenerative" pathway. Treatment with an antiproliferative compound of the invention can be used to reverse the pathological epidermal acativation and can provide a basis for sustained remission of the disease.

A variety of other keratotic lesions are also candidates for treatment with the compounds of the invention. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a composition containing at least one compound of formulae (I), (Ia) to (If), (II) and (IIa) to (IIf) in amounts sufficient to inhibit hyperproliferation of epidermal/epidermoid cells of the lesion.

Acne represents yet another dermatologic ailment which may be treated by the compounds of the invention. Acne vulgaris, for instance, is a multifactorial disease most commonly occurring in teenagers and young adults, and is characterized by the appearance of inflammatory and non-inflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative compound of formulae (I), (Ia) to (If), (II) and (IIa) to (IIf), particularly topical preparations, may be useful for preventing the transitional features of the ducts, e.g. hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions which are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow crusted patches on various areas, especially the scalp, with exfoliation of an excessive amount of dry scales. The compounds of the invention can also be used in the treatment of stasis dermatitis, an often chronic, usually eczematous dermatitis. Actinic dermatitis is dermatitis that due to exposure to actinic radiation such as that from the sun, ultraviolet waves or x- or gamma-radiation. According to the present invention, the compounds of the invention can be used in the treatment and/or prevention of certain symptoms of dermatitis caused by unwanted proliferation of epithelial cells. Such therapies for these various forms of dermatitis can also include topical and systemic corticosteroids, antipuritics, and antibiotics.

Ailments which may be treated by the compounds of the invention are disorders specific to non-humans, such as mange.

In still another embodiment, the compounds of the invention can be used in the treatment of human cancers, particularly basal cell carcinomas and other tumors of epithelial tissues such as the skin. For example, compounds of the invention can be employed, in the subject method, as part of a treatment for basal cell nevus syndrome (BCNS), and other other human carcinomas, adenocarcinomas, sarcomas and the like.

In another embodiment, the compounds of the invention are used as part of a treatment of prophylaxis regimen for treating (or preventing) basal cell carcinoma. The deregulation of the Wnt signaling pathway may be a general feature of basal cell carcinomas caused by ptc mutations. Consistent overexpression of human ptc mRNA has been described in tumors of familial and sporadic BCCs, determined by in situ hybridization. Mutations that inactivate ptc may be expected to result in overexpression of mutant Ptc, because ptc displays negative autoregulation. Likewise, mutations that inactivate Wnt may be expected to result in overexpression of mutant Wnt, because Wnt displays negative autoregulation. Prior research demonstrates that overexpression of hedgehog proteins can also lead to tumorigenesis. That sonic hedgehog (Shh) has a role in tumorigenesis in the mouse has been suggested by research in which transgenic mice overexpressing Shh in the skin developed features of BCNS, including multiple BCC-like epidermal proliferations over the entire skin surface, after only a few days of skin development. A mutation in the Shh human gene from a BCC was also described; it was suggested that Wnt, Shh or other Hh genes in humans could act as dominant oncogenes in humans. Sporadic ptc mutations have also been observed in BCCs from otherwise normal individuals, some of which are UV-signature mutations. In one recent study of sporadic BCCs, five UV-signature type mutations, either CT or CCTT changes, were found out of fifteen tumors determined to contain ptc mutations. Another recent analysis of sporadic ptc mutations in BCCs and neuroectodermal tumors revealed one CT change in one of three ptc mutations found in the BCCs. See, for example, Goodrich et al., Science 277:1109-13 (1997); Xie et al. Cancer Res. 57:2369-72 (1997); Oro et al. Science 276:817-21 (1997); Xie et al, Genes Chromosomes Cancer 18:305-9 (1997); Stone et al, Nature 384:129-34 (1996); and Johnson et al. Science 272: 1668-71 (1996).

The compounds of the invention can also be used to treat patients with BCNS, e.g., to prevent BCC or other effects of the disease which may be the result of Wnt-mediated disorders. Basal cell nevus syndrome is a rare autosomal dominant disorder characterized by multiple BCCs that appear at a young age. BCNS patients are very susceptible to the development of these tumors; in the second decade of life, large numbers appear, mainly on sun-exposed areas of the skin. This disease also causes a number of developmental abnormalities, including rib, head and face alterations, and sometimes polydactyly, syndactyly, and spina bifida. They also develop a number of tumor types in addition to BCCs: fibromas of the ovaries and heart, cysts of the skin and jaws, and in the central nervous system, medulloblastomas and meningiomas. The compounds of the invention can be used to prevent or treat such tumor types in BCNS and non-BCNS patients. Studies of BCNS patients show that they have both genomic and sporadic mutations in the ptc gene, suggesting that these mutations are the ultimate cause of this disease.

In another aspect, the present invention provides pharmaceutical preparations and methods for controlling the formation of megakaryocyte-derived cells and/or controlling the functional performance of megakaryocyte-derived cells. For instance, certain of the compositions disclosed herein may be applied to the treatment or prevention of a variety hyperplastic or neoplastic conditions affecting platelets.

Furthermore, the invention relates to pharmaceutical compositions comprising at least one compound according to the invention. In a preferred embodiment, the invention relates to pharmaceutical compositions comprising at least one compound according to the invention in a mixture with an inert carrier, where said inert carrier is a pharmaceutical carrier.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The invention further relates to a process for the preparation of a medicament comprising the steps of:

a) preparing at least one compound according to the formulae (I), (Ia) to (If), (II) and (IIa) to (IIf) and b) formulating a medicament containing at least said compound;

and to a method of treating a mammal for modulating the Wnt signalling pathway wherein the method comprises administering to said mammal a therapeutically effective amount of a compound according to formulae (I), (Ia) to (If), (II) and (IIa) to (IIf).

The compounds according to the invention used for the preparation of a medicament for the modulation of the Wnt signalling pathway in a mammal may be administered in any convenient route. The compounds are formulated to be compatible with the desired route of administration and may be administered together with other biologically active agents.

The compounds may be formulated for the intravenous, intradermal, subcutanus, intramuscular, intraperitoneal, epidural, oral, transdermal, transmucosal, rectal or pulmonary administration. Administration can be systemic or local. Pulmonary administration can be employed by use of an inhaler or nebulizer, and formulation with an aerosolizing agent, for example. In another embodiment, the compound can be delivered in a vesicle, in particular a liposome (Langer (1990) Science 249, 1527.

In yet another embodiment, the compound can be delivered via a controlled release system. In one embodiment, a pump may be used (Sefton (1987) CRC Crit. Ref. Biomed. Eng. 14, 201; Buchwald et al. (1980) Surgery 88, 507; Saudek et al. (1989) N. Engl. J. Med. 321, 574). In another embodiment, polymeric materials can be used (Ranger and Peppas (1983) Macromol. Sci. Rev. Macromol. Chem. 23, 61; Levy et al. (1985) Science 228, 190; During et al. (1989) Ann. Neurol. 25, 351; Howard et al. (1989) J. Neurosurg. 71, 858). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115). Other controlled release systems are discussed in the review by Langer (1990, Science 249, 1527).

Toxicity and therapeutic efficacy of the compounds of the invention can be determined by standard pharmaceutical procedures in cell cultures or experimental animals. The results obtained from the cell culture assays and animal studies can be used in formulating the range of dosage for use in medicaments in humans. The specific dosage for any particular subject is influenced by several factors, e.g. by the activity of the specific compound used, the age, body weight, general health, gender and diet of the subject, the time and the route of administration and the rate of excretion.

EXAMPLES

Example 1

2-Amino-4-(3-bromo-4,5-dimethoxy-phenyl)-4H-benzo[h]chromene-3-carbonitrile (1)

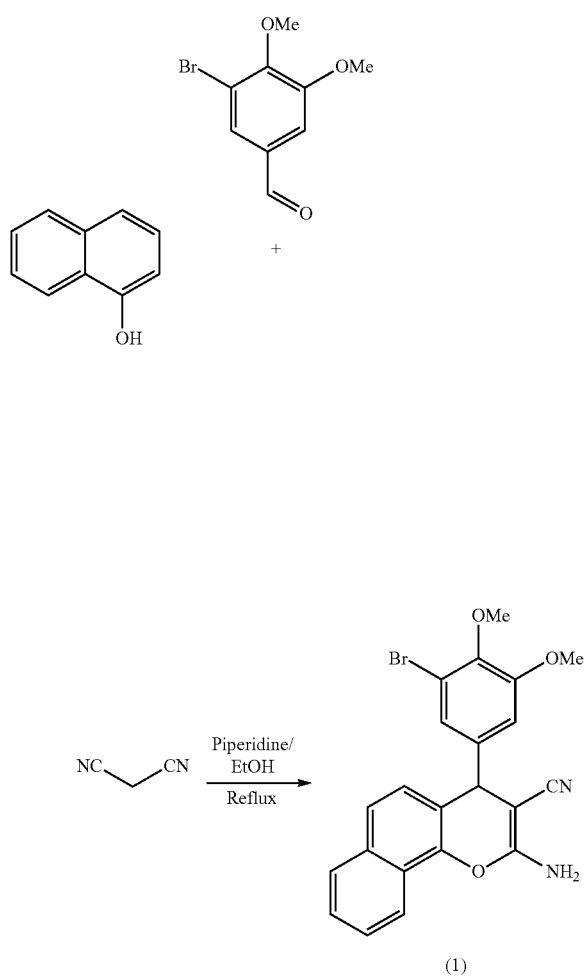

1-Naphthol (170 mg, 1.2 mmol), 3-bromo-4,5-dimethoxybenzaldehyde (245 mg, 1 mmol) and malononitrile (66 mg, 1 mmol) were taken in 7 ml ethanol at room temperature, charged with piperidine (50 μl) and then stirred at 80° C. under LC-MS (Liquid chromatography-mass spectrometry) control till the reaction was complete. The reaction mixture was cooled down to room temperature and diluted with water to about 15 ml drop wise addition. The mixture was stirred at room temperature for about 1 h. Thus formed precipitates were collected by filtration, washed well with 60% aqueous ethanol and dried under high vacuum to get 394 mg (0.90 mmol, 90%) of the pure solids of the title compound.

Example 2

2-Amino-4-(4-benzyloxy-3-bromo-5-methoxy-phenyl)-4H-benzo[h]chromene-3-carbonitrile (2)

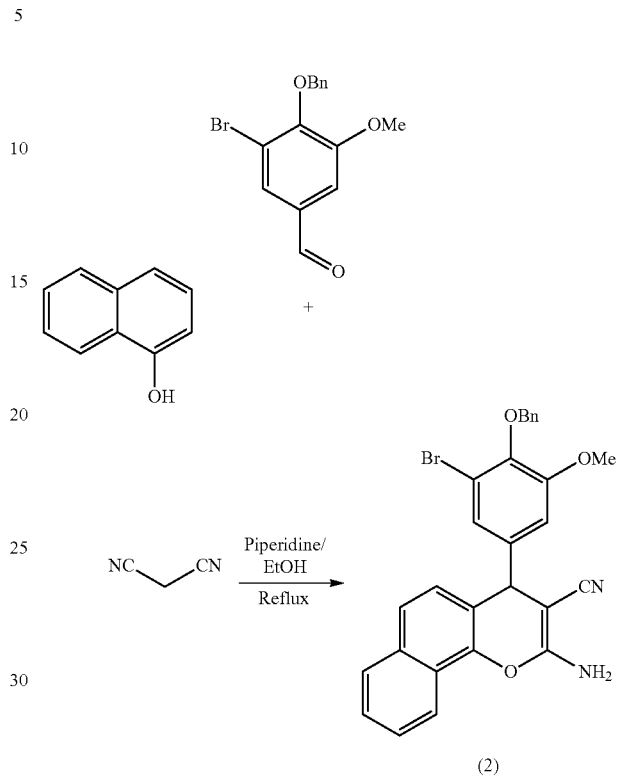

1-Naphthol (2.16 g, 15 mmol), 4-benzyloxy-3-bromo-5-methoxy-benzaldehyde (4 g, 12.5 mmol) and malononitrile (825 mg, 12.5 mmol) were taken in 30 ml ethanol at room temperature, charged with piperidine (200 μl) and then stirred at 80° C. under LC-MS control till the reaction was complete. The reaction mixture was then cooled down to room temperature, diluted with 60 ml water and stirred for about 2 h at room temperature. Thus formed precipitates were collected by filtration, washed with 1:1 mixture of ethanol/water and dried under high vacuum yielding pure solids of the title compound (6.0 g, 11.7 mmol, 93.5%).

Example 3

2-Amino-4-(4-allyloxy-3-bromo-5-methoxy-phenyl)-4H-benzo[h]chromene-3-carbonitrile (3)

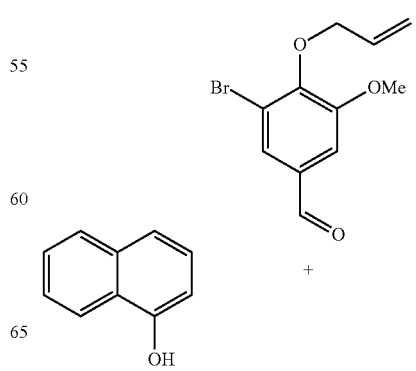

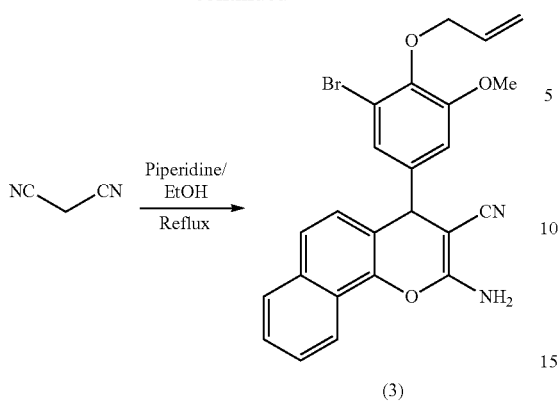

(3)

1-Naphthol (170 mg, 1.2 mmol), 4-allyloxy-3-bromo-5-methoxy-benzaldehyde (271 mg, 1 mmol) and malononitrile (66 mg, 1 mmol) were taken in 7 ml ethanol at room temperature, charged with piperidine (50 μl) and then stirred at 80° C. under LC-MS control till the reaction was complete. The reaction mixture was then cooled down to room temperature, diluted with 10 ml water, stirred for 2 h at room temperature, solids were collected by filtration, washed well with 1:1 mixture of ethanol/water and dried under high vacuum yielding 370 mg (0.8 mmol, 80%) of the title compound.

Example 4

4-(4-Allyloxy-3-bromo-5-methoxy-phenyl)-2-amino-4H-benzo[h]chromene-3-carboxylic acid ethyl ester (4)

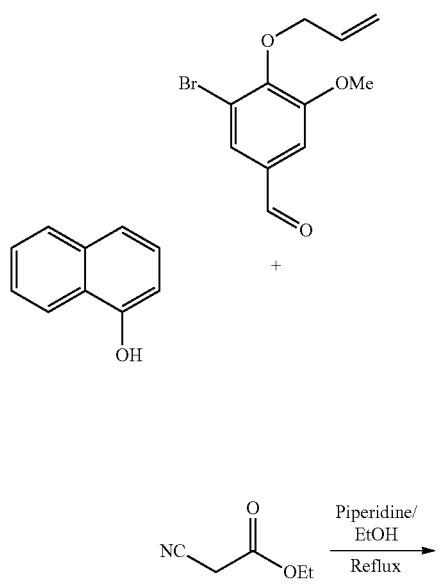

(4)

1-Naphthol (170 mg, 1.2 mmol), 4-allyloxy-3-bromo-5-methoxy-benzaldehyde (271 mg, 1 mmol) and ethyl cyanoacetate (113 mg, 1 mmol) were taken in 7 ml ethanol at room temperature, charged with piperidine (50 μL) and then stirred at 80° C. under LC-MS control till the reaction was complete. The reaction mixture was cooled down to room temperature, diluted with 10 ml water, stirred for 2 h at room temperature, solids were collected by filtration, washed with 1:1 mixture of ethanol/water and dried (270 mg, 0.58 mmol, 58%).

Example 5

2-Amino-4-(3-bromo-4-hydroxy-5-methoxy-phenyl)-4H-benzo[h]chromene-3-carbonitrile (5)

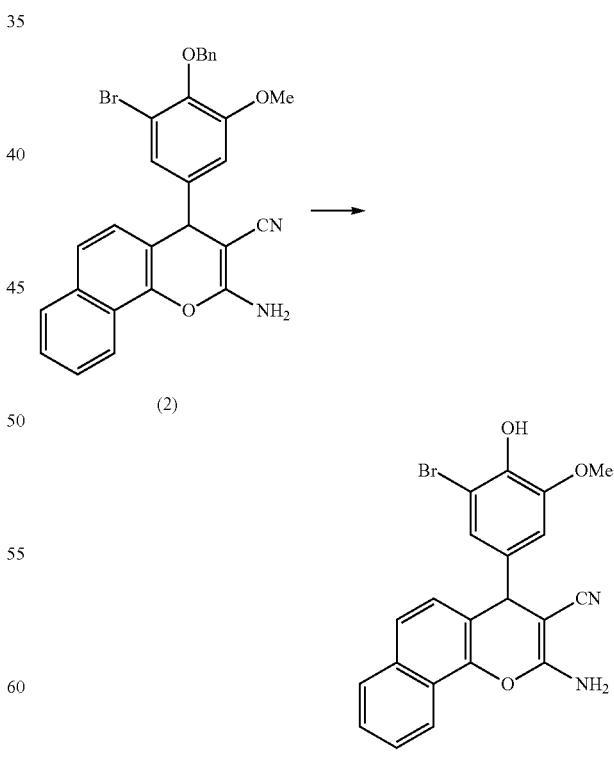

(5)

2-Amino-4-(4-benzyloxy-3-bromo-5-methoxy-phenyl)-4H-benzo[h]chromene-3 -carbonitrile (2) (2 g, 3.89 mmol)

was taken in 20 ml acetic acid and charged with 10M hydrochloric acid (10 ml) under vigorous stirring at room temperature, and stirred further at room temperature until the reaction was complete. The reaction mixture was then diluted with 50 ml water, stirred for 3 h at room temperature, thus formed solids were separated by filtration, washed with water and then dried under high vacuum (1.61g, 3.8 mmol, 97.8%).

Example 6

2-Amino-4-(3-bromo-4,5-dimethoxy-phenyl)-4H-benzo[h]chromene-3-carboxylic acid ethyl ester(6)

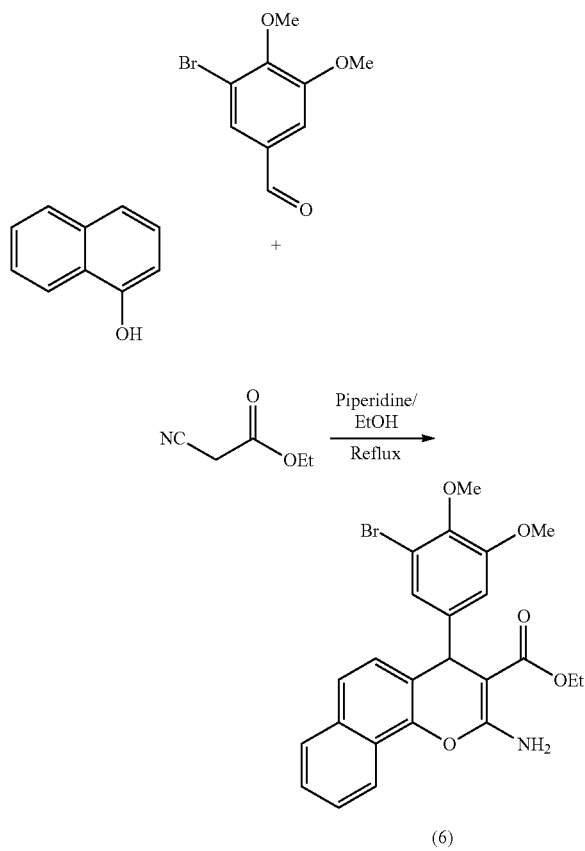

(6)

1-Naphthol (170 mg, 1.2 mmol), 3-bromo-4,5-dimethoxybenzaldehyde (245 mg, 1 mmol) and ethyl cyanoacetate (113 mg, 1 mmol) were taken in 7 ml ethanol at room temperature, charged with piperidine (50 μl) and then stirred at 80° C. under LC-MS control till the reaction was complete. The reaction mixture was cooled down to room temperature, diluted with water to about 15 ml and stirred for 1 h at room temperature. The solids were collected by filtration, washed well with 60% aq ethanol and dried under high vacuum (420 mg, 0.86 mmol, 86%).

Example 7

2-Amino-4-(3,4,5-trifluoro-phenyl)-4H-benzo[h]chromene-3-carbonitrile (7)

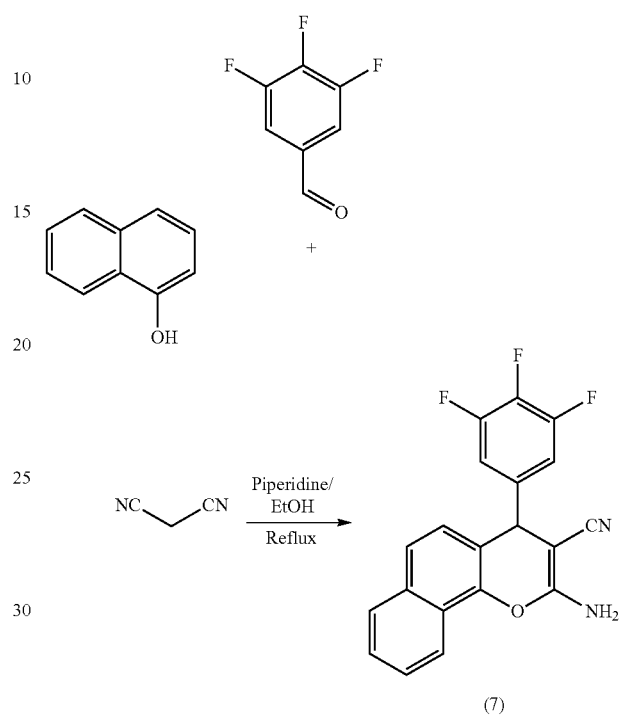

(7)

1-Naphthol (170 mg, 1.2 mmol), 3,4,5-trifluorobenzaldehyde (160 mg, 1 mmol) and malononitrile (66 mg, 1 mmol) were taken in 7 ml ethanol at room temperature, charged with piperidine (50 μl) and then stirred at 80° C. under LC-MS control till the reaction was complete. The reaction mixture was cooled down to room temperature, diluted with water to about 15 ml and stirred for about 1 h room temperature. The solids were collected by filtration, washed with 60% aq. ethanol and dried under high vacuum to yield the title compound (284 mg, 0.81 mmol, 81%).

Example 8

2-Amino-7-hydroxy-4-(3-bromo-4,5-dimethoxy-phenyl)-4H-benzo[h]chromene-3-carbonitrile (8)

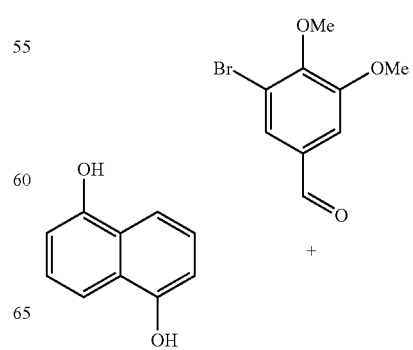

-continued

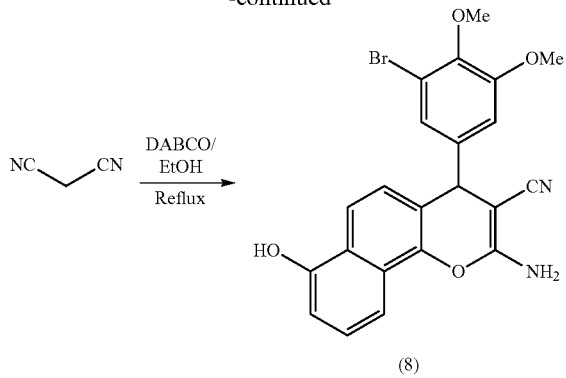

(8)

1,5-Dihydroxy-naphthalene (704 mg, 4.4 mmol), 3-bromo-4,5-dimethoxy-benzaldehyde (1077 mg, 4.4 mmol) and malononitrile (295 mg, 4.4 mmol) were taken in 40 ml ethanol at room temperature, charged with DABCO (triethylenediamine) (48.4 µl, 1.46 mmol) and then stirred at 80° C. under LC-MS control for 18 h. The reaction mixture was then cooled down to room temperature. The mixture was diluted with water to about 100 ml, stirred at room temperature for 1 h and the precipitates were separated by filtration. It was washed well with 50% aqueous ethanol and dried under vacuum (1.18 g, 2.6 mmol, 59%).

Example 9

2-Amino-6-hydroxy-4-(3-bromo-4,5-dimethoxy-phenyl)-4H-benzo[h]chromene-3-carbonitrile (9)

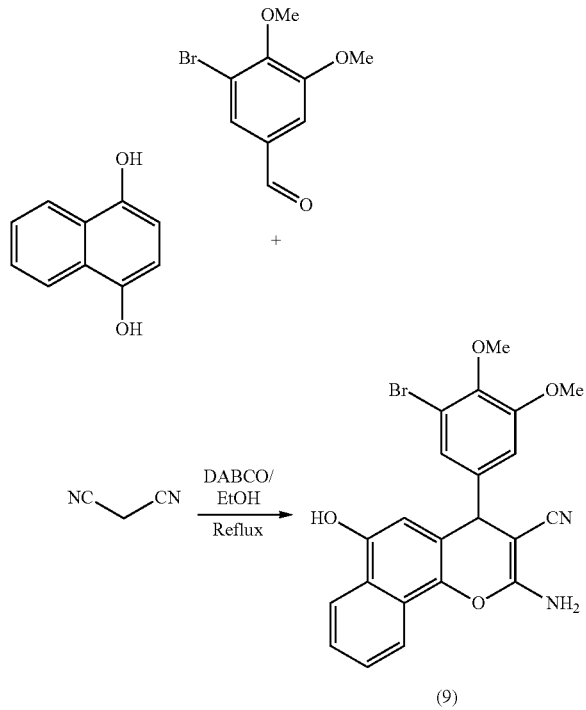

(9)

1,4-Dihydroxy-naphthalene (704 mg, 4.4 mmol), 3-bromo-4,5-dimethoxy-benz-aldehyde (1077 mg, 4.4 mmol) and malononitrile (295 mg, 4.4 mmol) were taken in 40 ml ethanol at room temperature, charged with DABCO (48.4 µl, 1.46 mmol) and then refluxed with stirring under LC-MS control for 18 h. The reaction mixture was then cooled down to room temperature. The mixture was diluted with water to about 100 ml, stirred at room temperature for 1 h and the precipitates were separated by filtration. It was washed well with 50% aqueous ethanol and dried under vacuum (1.68 g, 3.7 mmol, 84%).

Example 10

2,7-Diamino-4-(3-bromo-4,5-dimethoxy-phenyl)-4H-benzo[h]chromene-3-carbonitrile (10)

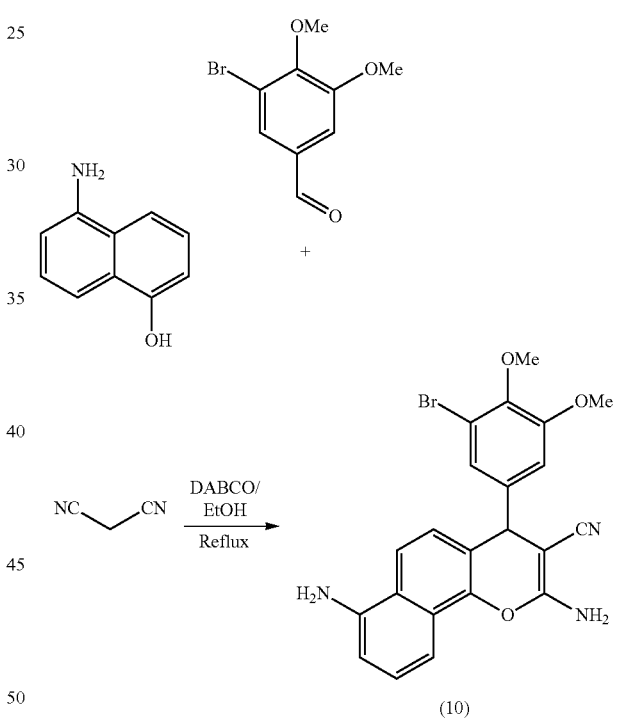

(10)

5-Amino-naphthol (700 mg, 4.4 mmol), 3-bromo-4,5-dimethoxy-benzaldehyde (1077 mg, 4.4 mmol) and malononitrile (295 mg, 4.4 mmol) were taken in 40 ml ethanol at room temperature, charged with DABCO (48.4 µl, 1.46 mmol) and then stirred at 80° C. under LC-MS control for 18 h. The reaction mixture was then cooled down to room temperature. The mixture was diluted with water to about 100 ml, stirred at room temperature for 1 h and the precipitates were separated by filtration. It was washed well with 50% aqueous ethanol and dried under vacuum (1.58 g, 3.5 mmol, 79.5%).

Example 11

2,4,7-Triamino-5-(3,4,5-trifluoro-phenyl)-5H-pyrano[2,3-d]pyrimidine-6-carbonitrile (11)

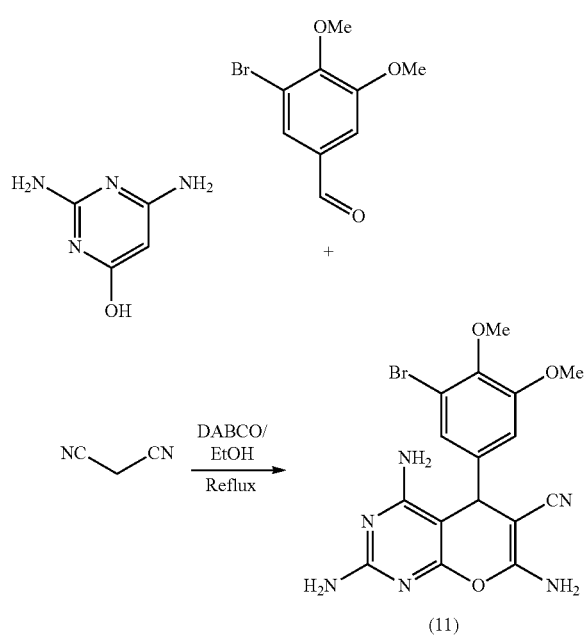

2,4-Diamino-6-hydroxypyrimidine (555 mg, 4.4 mmol), 3-bromo-4,5-dimethoxy-benzaldehyde (1077 mg, 4.4 mmol) and malononitrile (295 mg, 4.4 mmol) were taken in 40 ml ethanol at room temperature, charged with DABCO (48.4 µl, 1.46 mmol) and then stirred at 80° C. under LC-MS control for 18 h. The reaction mixture was then cooled down to room temperature. The mixture was diluted with water to about 100 ml, stirred at room temperature for 1 h and the precipitates were separated by filtration. It was washed well with 50% aqueous ethanol and dried under vacuum to get the title compound (1.47 g, 3.51 mmol, 79.7% of the theoretical yield).

Example 12

7-Amino-4-hydroxy-2-methyl-5-(3,4,5-trifluoro-phenyl)-5H-pyrano[2,3-d]pyrimidine-6-carbon (12)

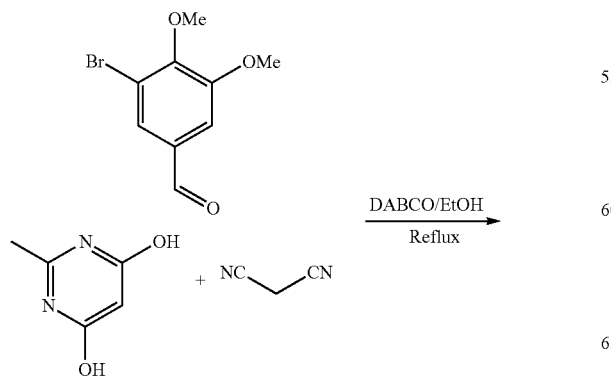

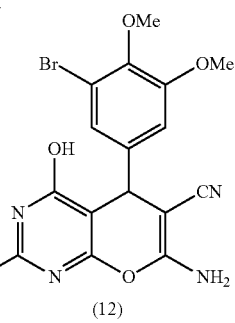

4,6-Dihydroxy-2-methylpyrimidine (555 mg, 4.4 mmol), 3-bromo-4,5-dimethoxy-benzaldehyde (1077 mg, 4.4 mmol) and malononitrile (295 mg, 4.4 mmol) were taken in 40 ml ethanol at room temperature, charged with DABCO (48.4 µl, 1.46 mmol) and then stirred at 80° C. under LC-MS control for 18 h. The reaction mixture was then cooled down to room temperature. The mixture was diluted with water to about 100 ml, stirred at room temperature for 1 h and the precipitates were separated by filtration. It was washed well with 50% aqueous ethanol and dried under vacuum (1.38 g, 3.29 mmol, 74.8% of the theoretical yield).

Example 13

7-Amino-4-hydroxy-5-(3,4,5-trifluoro-phenyl)-5H-pyrano[2,3-d]pyrimidine-6-carbonitrile (13)

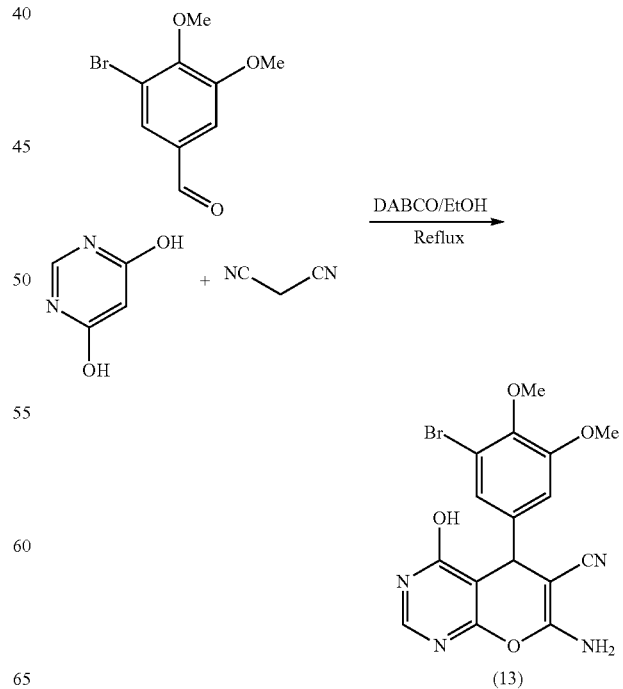

4,6-Dihydroxypyrimidine (493 mg, 4.4 mmol), 3-bromo-4,5-dimethoxy-benzaldehyde (1077 mg, 4.4 mmol) and malononitrile (295 mg, 4.4 mmol) were taken in 40 ml ethanol at room temperature, charged with DABCO (48.4 μl, 1.46 mmol) and then stirred at 80° C. under LC-MS control for 18 h. The reaction mixture was then cooled down to room temperature. The mixture was diluted with water to about 100 ml, stirred at room temperature for 1 h and the precipitates were separated by filtration. It was washed well with 50% aqueous ethanol and dried under vacuum (1.43 g, 3.53 mmol, 80%).

Example 14

7-Amino-5-(3-bromo-4,5-dimethoxy-phenyl)-2,4-dimethyl-5H-pyrano[2,3-d]pyrimidine-6-carbonitrile (14)

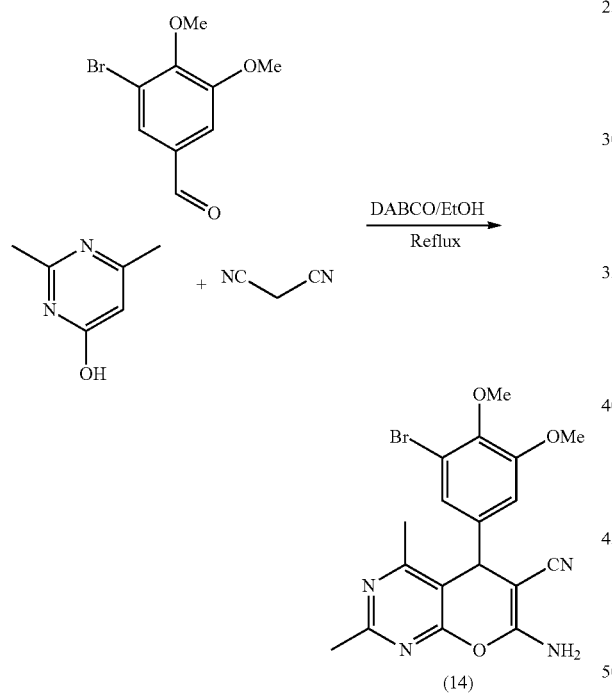

4-Hydroxy-2,6-dimethylpyrimidine (546 mg, 4.4 mmol), 3-bromo-4,5-dimethoxy-benzaldehyde (1077 mg, 4.4 mmol) and malononitrile (295 mg, 4.4 mmol) were taken in 2 ml ethanol at room temperature, charged with DABCO (48.4 μl, 1.46 mmol) and then stirred at 80° C. under LC-MS control for 18 h. The reaction mixture was then cooled down to room temperature. The mixture was diluted with water to about 100 ml, stirred at room temperature for 1 h and the precipitates were separated by filtration. It was washed well with 50% aqueous ethanol and dried under vacuum (1.52 g, 3.64 mmol, 82.8%).

Example 15

7-Amino-5-(3-bromo-4,5-dimethoxy-phenyl)-4-hydroxy-5H-pyrano[2,3-d]pyrimidine-6-carbonitrile (15)

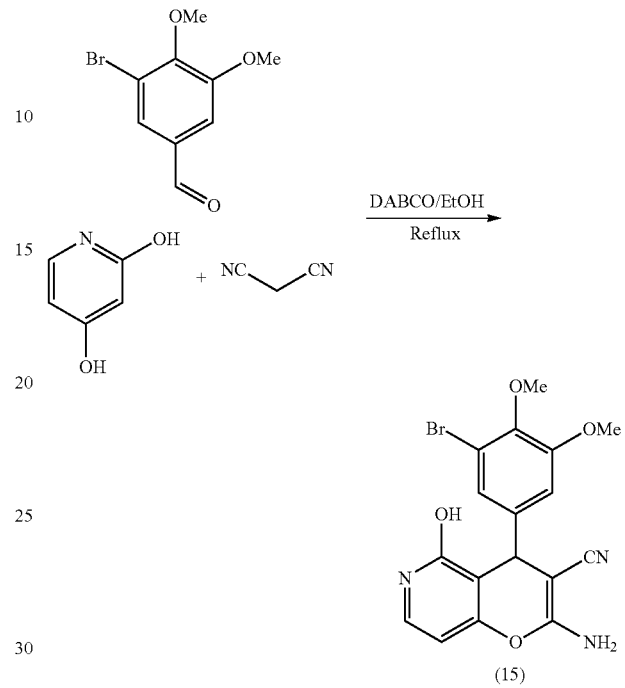

2,4-Dihydroxypyridine (488 mg, 4.4 mmol), 3-bromo-4,5-dimethoxy-benzaldehyde (1077 mg, 4.4 mmol) and malononitrile (295 mg, 4.4 mmol) were taken in 2 ml ethanol at room temperature, charged with DABCO (48.4 μl, 1.46 mmol, 30% mol) and then stirred at 80° C. under LC-MS control for 18 h. The reaction mixture was then cooled down to room temperature. The mixture was diluted with water to about 100 ml, stirred at room temperature for 1 h and the precipitates were separated by filtration. It was washed well with 50% aqueous ethanol and dried under vacuum (1.47 g, 3.64 mmol, 82.7%).

Example 16

3-Amino-1-(3-bromo-4,5-dimethoxy-phenyl)-6-methyl-1H-4-oxa-5-aza-phenanthrene-2-carbonitrile (16)

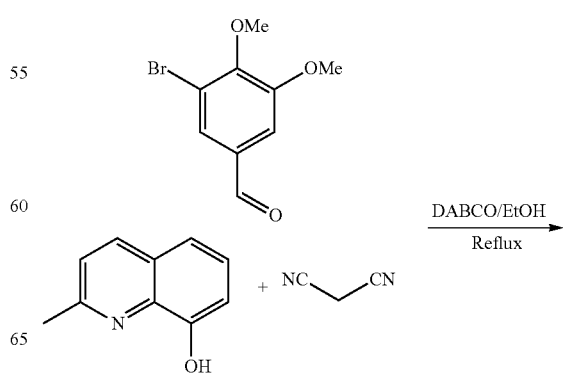

-continued

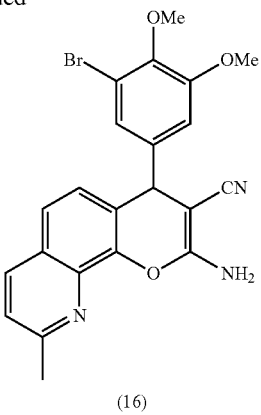

(16)

8-Hydroxyquinaldine (382 mg, 2.4 mmol), 5-bromo-3,4-dimethoxybenzaldehyde (490 mg, 2 mmol) and malononitrile (132 mg, 2 mmol) were taken in 25 ml ethanol at room temperature, charged with DABCO (22 µl, 0.3 mmol) and then stirred at 80° C. under LC-MS control for 3 days. The reaction mixture was cooled down to room temperature, diluted with water to about 100 ml and then extracted with ethyl acetate (2×50 ml). The organic solution was washed with 5% sodium bicarbonate solution (2×50 ml) and then dried over magnesium sulfate, solvent was evaporated under vacuum at 40° C. and the residue was dried under high vacuum giving 217 mg of the title compound (0.48 mmol, 20%).

Example 17

2-Amino-4-(3-bromo-4,5-dimethoxy-phenyl)-5-hydroxy-4H-pyrano[3,2-c]quinoline-3-carbonitrile (17)

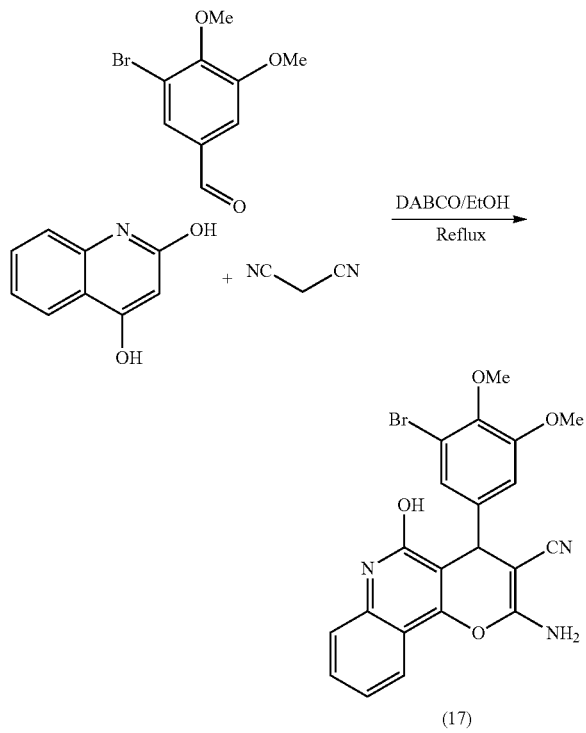

(17)

2,4-Quinolinediol (193 mg,1.2 mmol), 3-bromo-4,5-dimethoxy-benzaldehyde (245 mg, 1 mmol) and malononitrile (66 mg, 1 mmol) were taken in 25 ml ethanol at room temperature, charged with DABCO (11 µl, 0.1 mmol) and then stirred at 80° C. under LC-MS control for 21 h whereby the reaction was complete. The reaction mixture was cooled down to room temperature, diluted with water to about 100 ml and stirred for over night at room temperature. The solids were collected by filtration, washed well with 50% aqueous ethanol and dried under high vacuum yielding 395 mg (0.87 mmol, 87%) of the pure title compound.

Example 18

6-Amino-8-(3-bromo-4,5-dimethoxy-phenyl)-8H-5-oxa-1-aza-phenanthrene-7-carbonitrile (18)

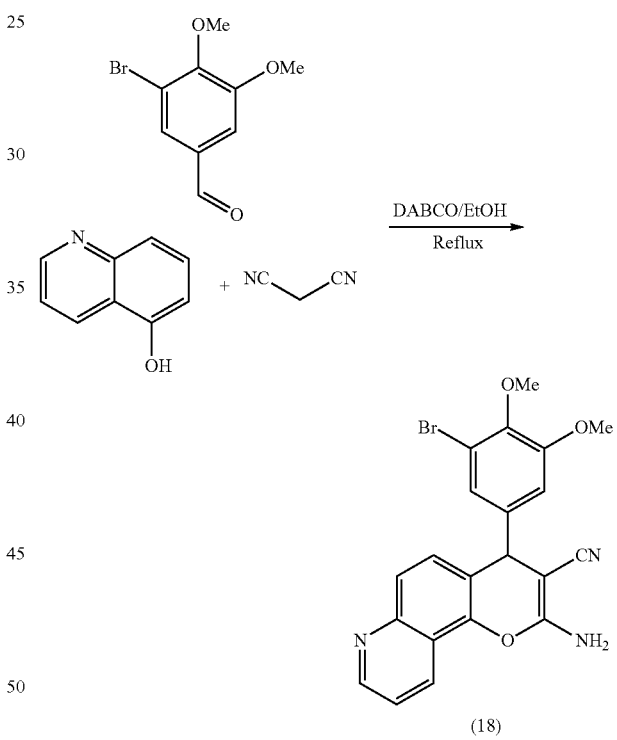

(18)

5-Hydroxyquinoline (174 mg, 1.2 mmol), 3-bromo-4,5-dimethoxy-benzaldehyde (245 mg, 1 mmol) and malononitrile (66 mg, 1 mmol) were taken in 25 ml ethanol at room temperature, charged with DABCO (11 0.1 mmol) and then stirred at 80° C. under LC-MS control for 21 h. The reaction mixture was cooled down to the room temperature, diluted with water to about 100 ml and stirred for over night. The solids were collected by filtration, washed with well 1:1 mixture of ethanol/water and dried under high vacuum yielding 134 mg (0.36 mmol, 36%) of the title compound.

Example 19

3-Amino-1-(3-bromo-4,5-dimethoxy-phenyl)-6-hydroxy-1H-4-oxa-5-aza-phenanthrene-2-carbonitrile (19)

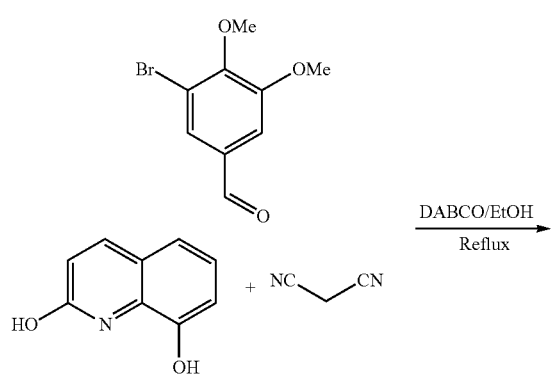

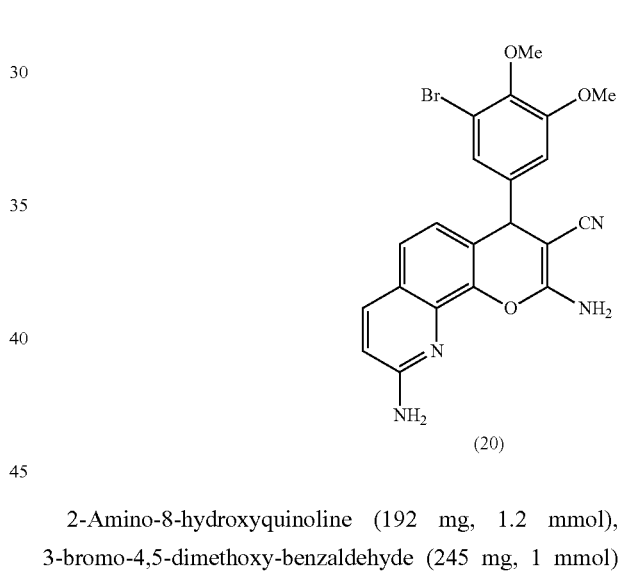

(19)

2,8-Quinolinediol (193 mg, 1.2 mmol), 3-bromo-4,5-dimethoxy-benzaldehyde (245 mg, 1 mmol) and malononitrile (66 mg, 1 mmol) were taken in 25 ml ethanol at room temperature, charged with DABCO (33 μl, 0.3 mmol) and then stirred at 90° C. under LC-MS control for 3 days. The reaction mixture was then cooled down to room temperature, diluted with water to about 100 ml and extracted with ethyl acetate (2×50 ml). The organic solution was washed with 5% aqueous sodium bicarbonate solution (2×50 ml) and then dried over magnesium sulfate, solvent was evaporated under vacuum at 40 C and dried (18 mg, 0.04 mmol, 4%).

Example 20

3,6-Diamino-1-(3-bromo-4,5-dimethoxy-phenyl)-1H-4-oxa-5-aza-phenanthrene-2-carbonitrile (20)

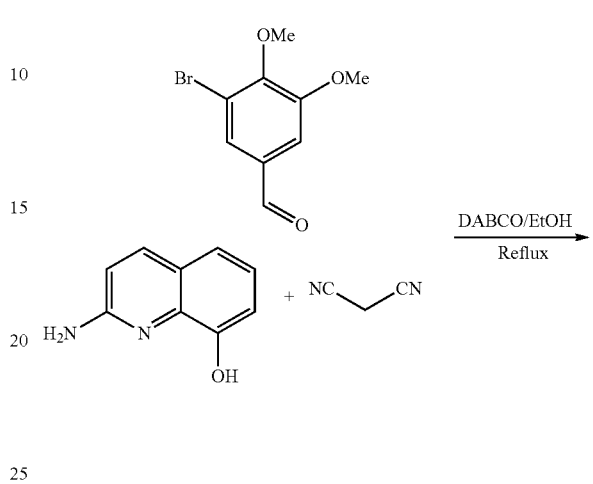

(20)

2-Amino-8-hydroxyquinoline (192 mg, 1.2 mmol), 3-bromo-4,5-dimethoxy-benzaldehyde (245 mg, 1 mmol) and malononitrile (66 mg, 1 mmol) were suspended in 25 ml ethanol at room temperature, charged with DABCO (33 μl, 0.3 mmol) and then stirred at 90° C. under LC-MS control for 6 days. The desired product was formed as a main component with some side products and a small amount of starting material was left. The reaction mixture was cooled down to room temperature, diluted with water to about 100 ml and stirred for over night at room temperature. Thus resulting precipitates were collected by filtration, washed well with 1:1 mixture of ethanol/water and finally with small portion of 10% ethyl acetate in cyclohexane and then dried under high vacuum to get pure solids (202 mg, 0.45 mmol, 45%) of the title compound.

Example 21

2-Amino-4-(3-bromo-4,5-dimethoxy-phenyl)-N-hydroxy-4H-benzo[h]chromene-3-carboxamidine (21)

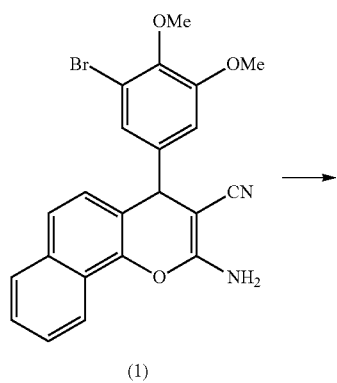

(1)

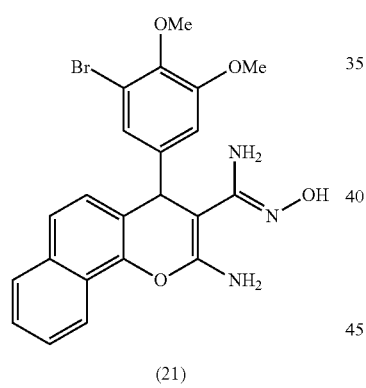

(21)

2-Amino-4-(3-bromo-4,5-dimethoxy-phenyl)-4H-benzo[h]chromene-3-carbonitrile (1) (4.38 g, 10 mmol), hydroxylamine hydrochloride (2.80 g, 40 mmol) and potassium carbonate (2.80 g, 1 mmol) were suspended in 80 ml ethanol at room temperature then stirred under LC-MS control 48 h. The reaction was clean with a minor side product (<3%). The reaction mixture was diluted with ethyl acetate to about 150 ml and stirred for 2 h at room temperature. Thus resulting insoluble salt was separated by filtration, washed well with ethyl acetate and the combined organic solution was evaporated to dryness at 40° C. under vacuum and the residue was dried under high vacuum to get solids (4.70 g, 10 mmol, 100% theoretical yield) of the title compound.

Example 22

3-[2-Amino-4-(3-bromo-4,5-dimethoxy-phenyl)-4H-benzo[h]chromen-3-yl]-4H-[1,2,4]oxadiazol-5-one (22)

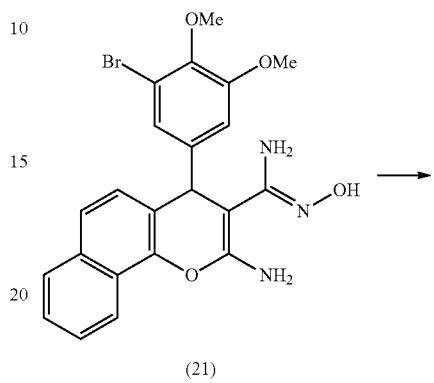

(21)

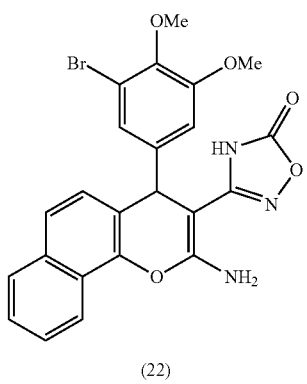

(22)

2-Amino-4-(3-bromo-4,5-dimethoxy-phenyl)-N-hydroxy-4H-benzo[h]chromene-3-carboxamidine (21), (118 mg, 0.25 mmol) and diimidazole carbonyl (40.5 mg, 0.25 mmol) are suspended in 10 ml tetrahydrofuran at room temperature and then is stirred under LC-MS control under heating. The reaction mixture is diluted with water to about 50 ml and stirred for 2 h at room temperature. Thus resulting precipitates are separated by filtration, washed well with water and is dried under high vacuum to get solids of the title compound.

Example 23

2-Amino-4-(3-bromo-4,5-dimethoxy-phenyl)-N-chloroacetylhydroxy-4H-benzo[h]chromene-3-carboxamidine (23)

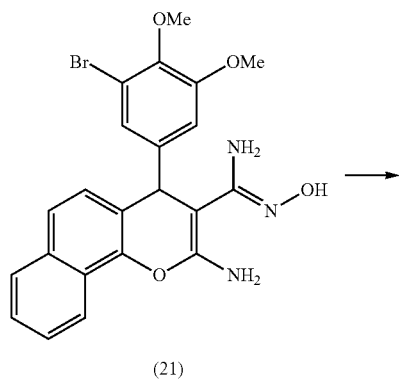

(21)

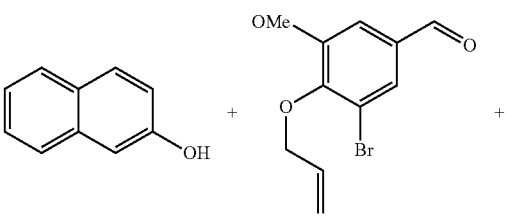

(23)

2-Amino-4-(3-bromo-4,5-dimethoxy-phenyl)-N-hydroxy-4H-benzo[h]chromene-3-carboxamidine (21) (118 mg, 0.25 mmol) and triethylamine (35 ml, 0.25 mmol) are taken in 10 ml tetrahydrofuran at −5° C. and is charged with chloroacetyl chloride (23 mg, 0.25 mmol) by drop wise addition under strong stirring. The reaction mixture is then stirred allowing to come to room temperature under LC-MS control and is stirred further at room temperature till the reaction is complete. The reaction mixture is diluted with water to about 50 ml and stirred for 2 h at room temperature. Thus resulting precipitates are separated by filtration, washed well with water and is dried under high vacuum to get solids of the title compound.

Example 24

4-(3-Bromo-4,5-dimethoxy-phenyl)-3-(5-chloromethyl-[1,2,4]oxadiazol-3-yl)-4H-benzo[h]chromen-2-ylamine (24)

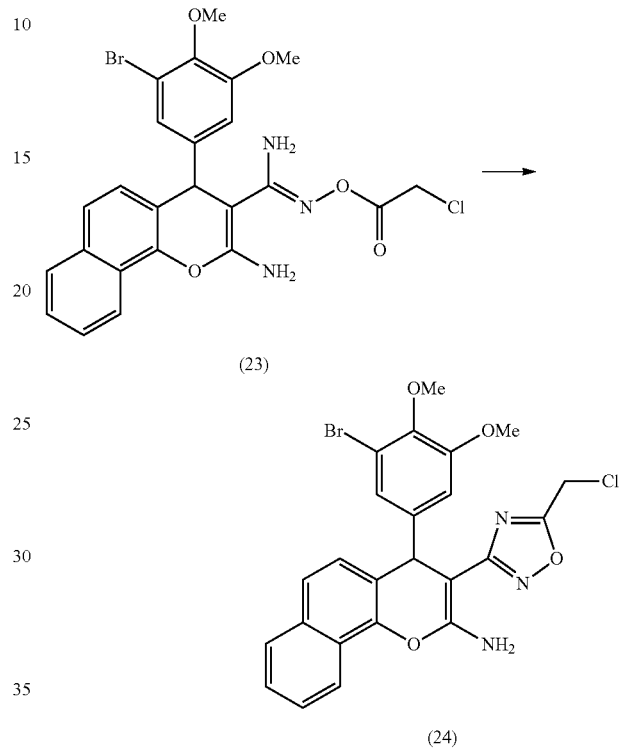

(23)

(24)

2-Amino-4(3-bromo-4,5-dimethoxy-phenyl)-N-chloroacetylhydroxy-4H-benzo[h]chromene-3-carboxamidine (23) (137 mg, 0.25 mmol) is taken in 10 ml xylene and refluxed under LC-MS control and is stirred further at room temperature till the reaction is complete. The reaction mixture is diluted with water to about 50 ml and stirred for 2 h at room temperature. Thus resulting precipitates are separated by filtration, washed well with water and is dried under high vacuum to get solids of the title compound.

Example 25

4-(4-Allyloxy-3-bromo-5-methoxy-phenyl)-2-amino-4H-benzo[g]chromene-3-carboxylic acid ethyl ester (25)

-continued

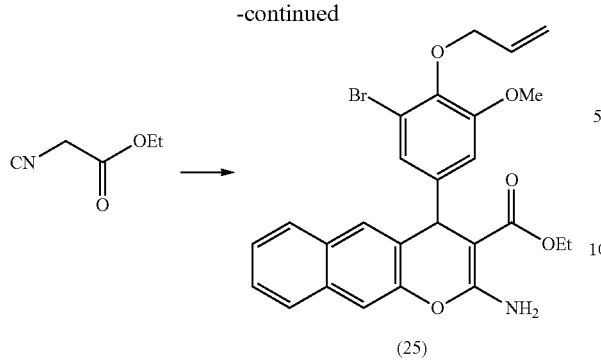

(25)

2-Naphthol (170 g, 1.2 mmol), 4-allyloxy-3-bromo-5-methoxy-benzaldehyde (271 g, 1 mmol) and ethyl cyanoacetate (113 mg, 1 mmol) were taken in 7 ml ethanol at room temperature, charged with piperidine (50 μL) and then stirred at 80° C. under LC-MS control till the reaction was complete. The reaction mixture was cooled down to room temperature, diluted with 10 ml water, stirred for 2 h at room temperature, solids were collected by filtration, washed with 1:1 mixture of ethanol/water and dried (386 mg, 0.76 mmol, 76%).

Example 26

4-(4-Allyloxy-3-bromo-5-methoxy-phenyl)-2-amino-4H-benzo[g]chromene-3-Carbonitrile (26)

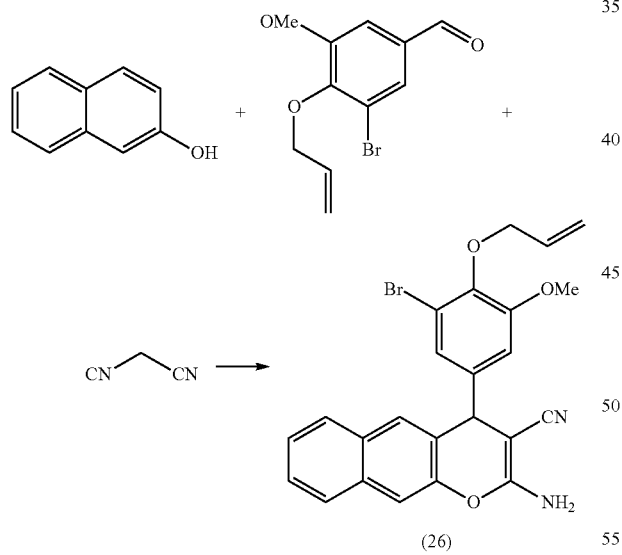

(26)

2-Naphthol (170 mg, 1.2 mmol), 4-allyloxy-3-bromo-5-methoxy-benzaldehyde (271 mg, 1 mmol) and malononitrile (66 mg, 1 mmol) were taken in 7 ml ethanol at room temperature, charged with piperidine (50 μL) and then stirred at 80° C. under LC-MS control till the reaction was complete. The reaction mixture was cooled down to room temperature, diluted with 10 ml water, stirred for 2 h at room temperature, solids were collected by filtration, washed with 1:1 mixture of ethanol/water and dried (235 mg, 0.51 mmol, 51%).

Example 27

2-Amino-4-(3,4,5-trifluoro-phenyl)-4H-benzo[g]chromene-3-carboxylic acid ethyl ester (27)

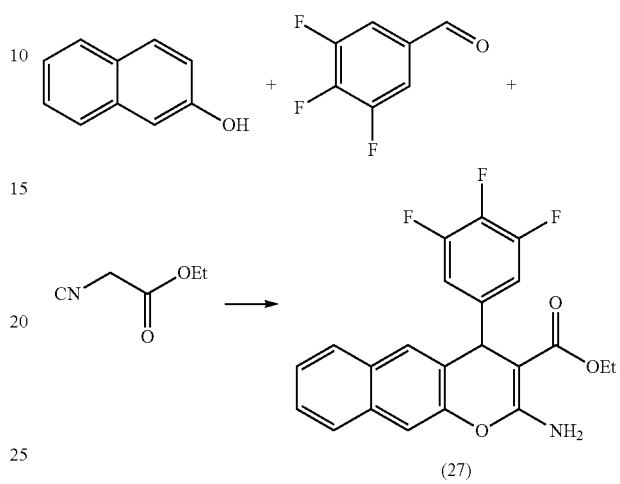

(27)

2-Naphthol (170 mg, 1.2 mmol), 3,4,5-trifluorobenzaldehyde (160 mg, 1 mmol) and ethyl cyanoacetate (113 mg, 1 mmol) were taken in 7 ml ethanol at room temperature, charged with piperidine (50 μL) and then stirred at 80° C. under LC-MS control till the reaction was complete. The reaction mixture was cooled down to room temperature, diluted with water to about 15 ml, stirred for 1 h, solids were collected by filtration, washed with 60% aq ethanol and dried (346 mg, 0.86 mmol, 86%).

Examples 28 and 29

2-Amino-4-(3,4,5-trifluoro-phenyl)-4H-benzo[g]chromene-3-carbonitrile (29) and 2-Amino-4-(3,5-difluoro-4-piperidin-1-yl-phenyl)-4H-benzo[g]chromene-3-carbonitrile (30)

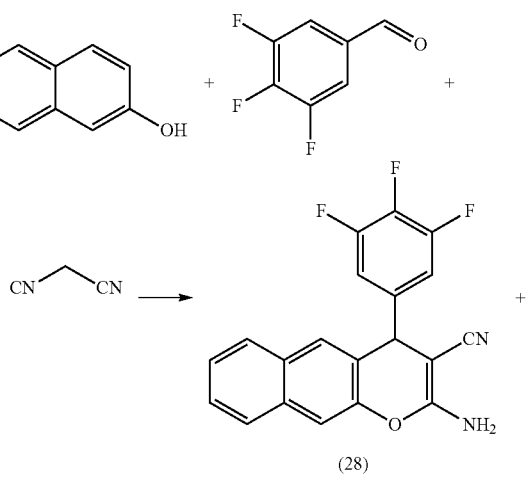

(28)

-continued

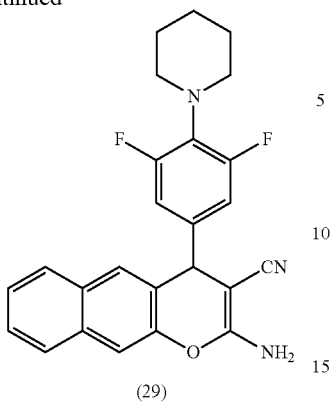

(29)

2-Naphthol (170 mg, 1.2 mmol), 3,4,5-trifluorobenzaldehyde (160 mg, 1 mmol) and malononitrile (66 mg, 1 mmol) were taken in 7 ml ethanol at room temperature, charged with piperidine (50 µL) and then stirred at 80° C. under LC-MS control till the reaction was complete. Two products were formed. The reaction mixture was cooled down to room temperature, diluted with water to about 50 ml, extracted with ethyl acetate (2×25 ml), organic solution was dried over magnesium sulfate, solvent was evaporated, residue was washed well with 1:1 mixture of ethanol/water and then dried. The residue was separated on HPLC (high pressure liquid chromatography) (21 mm×250 mm, RP18, 5 mm) with a methanol/water gradient (5% MeOH to MeOH in 25 min, flow 21 ml/min) to 2-amino-4-(3,4,5-trifluorophenyl)-4H-benzo[g]chromene-3-carbonitrile (28) (137 mg, 38.9%) and 2-amino-4-(3,5-difluoro-4-piperidin-1-yl-phenyl)-4H-benzo[g]chromene-3 -carbonitrile (29) (120 mg, 28.8%).

Example 30

2-Amino-4-(3-bromo-4,5-dimethoxy-phenyl)-4H-benzo[g]chromene-3-carbonitrile (30)

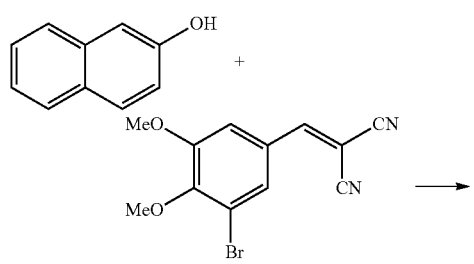

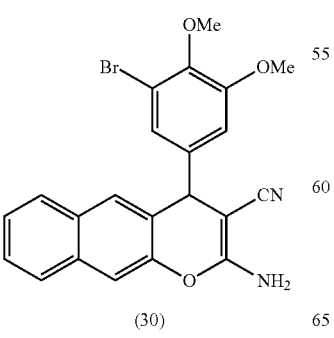

(30)

2-(3-Bromo-4,5-dimethoxy-benzylidene)-malononitrile (345 mg, 1.17 mmol) and 2-naphthole (203 mg, 1.4 mmol) were taken in 7 ml ethanol, charged with piperidine (50 µL) at room temperature and then stirred at 80° C. for 5 h. The reaction mixture was cooled down to room temperature, diluted with water to 20 ml, solids were separated by filtration, washed with methanol and dried under high vacuum yield pure solids of the title compound (358 mg, 82%).

Example 31

2-Dimethylamino-4-(3-bromo-4,5-dimethoxy-phenyl)-4H-benzo[g]chromene-3-carbonitrile (31)

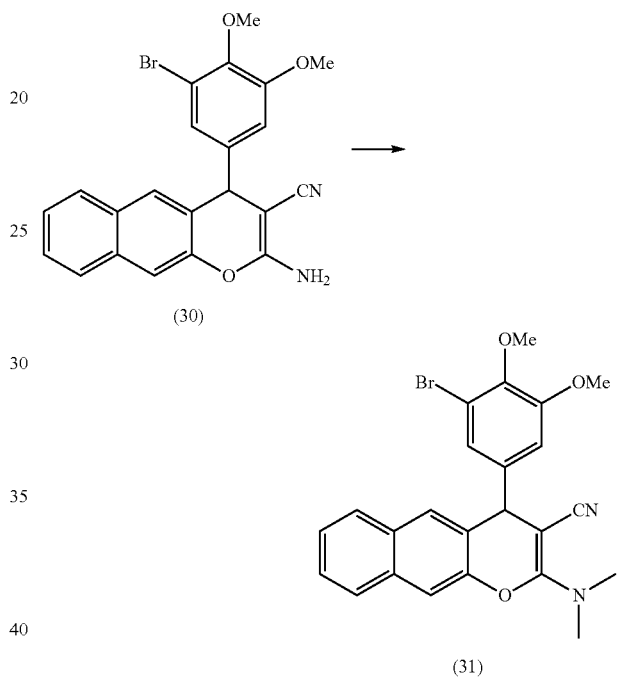

2-Amino-4-(3-bromo-4,5-dimethoxy-phenyl)-4H-benzo[g]chromene-3-carbonitrile (30) (24 mg) was taken in 1 ml dry DMF (dimethylformamide) and then charged with methyl iodide (30 µl) and potassium carbonate (30 mg) at room temperature. The reaction was completed after 20 h stirring at room temperature. The title compound was purified on HPLC (21 mm×250 mm, RP18, 5 mm) with a Methanol/water gradient (5% MeOH to MeOH in 25 min, flow 21 ml/min) to yield pale yellowish solids (18 mg).

Example 32

2-Amino-4-(3-bromo-4,5-dimethoxy-phenyl)-4H-benzo[g]chromene-3-carboxylic acid ethyl ester (32)

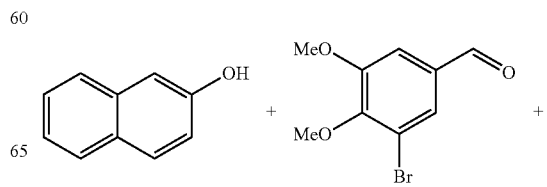

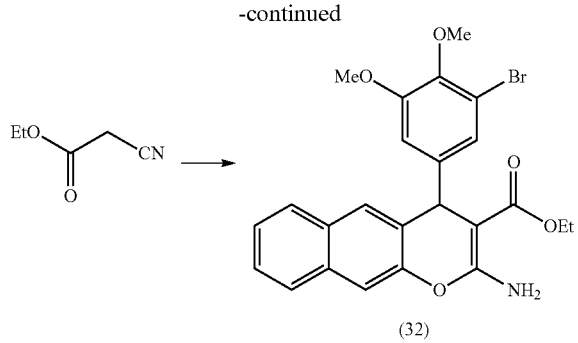

2-Naphthol (170 mg, 1.2 mmol), 5-bromo-3,4-dimethoxy-benzaldehyde (245 mg, 1 mmol) and ethyl cyanoacetate (113 mg, 1 mmol) were taken in 5 ml ethanol at room temperature, charged with piperidine (50 µl) and then stirred at 80° C. for 18 h. Reaction was complete and clean. The reaction mixture was then cooled down to room temperature, diluted with water to 20 ml, solids were separated by filtration, washed with methanol and dried under high vacuum (360 mg, 74%).

Example 33

3-Amino-1-(3-bromo-4,5-dimethoxy-phenyl)-1H-4-oxa-5-aza-phenanthrene-2-carbonitrile (33)

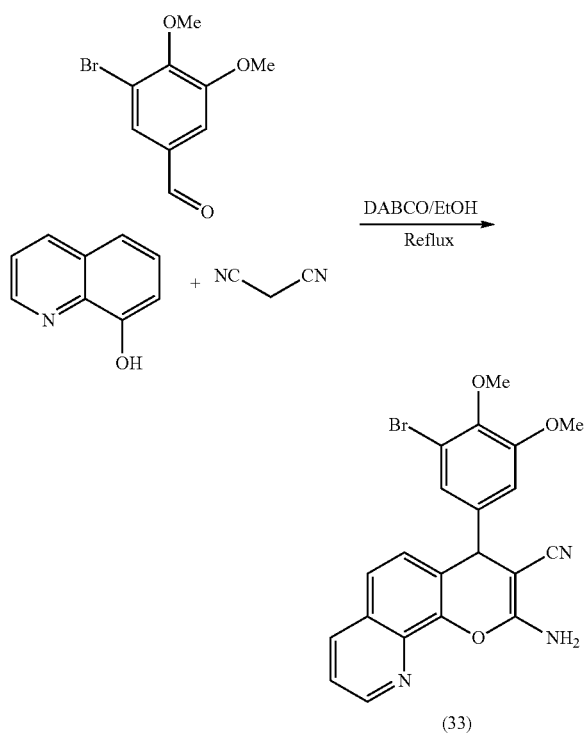

8-Hydroxychinoline (14.5 g, 100 mmol), 5-bromo-3,4-dimethoxy-benzaldehyde (20.4 g, 83.33 mmol) and malononitrile (5.5 g, 83.33 mmol) were taken in 250 ml ethanol at room temperature, charged with DABCO (917 µl, 8.33 mmol) and then stirred at 80° C. under LC-MS control for 18 days. The reaction mixture was cooled down to room temperature, diluted with water to about 500 ml and extracted with ethyl acetate (2×100 ml). The ethyl acetate solution was washed with 5% sodium bicarbonate solution (2×100 ml), dried over magnesium sulfate, solvent was then evaporated under vacuum at 40° C. and the solids were dried under high vacuum to yield 22.5 g (61.6%) of the title compound.

Example 34

3-Amino-1-(3-bromo-4,5-dimethoxy-phenyl)-9-chloro-1H-4-oxa-10-aza-phenanthrene-2-carbonitrile (34)

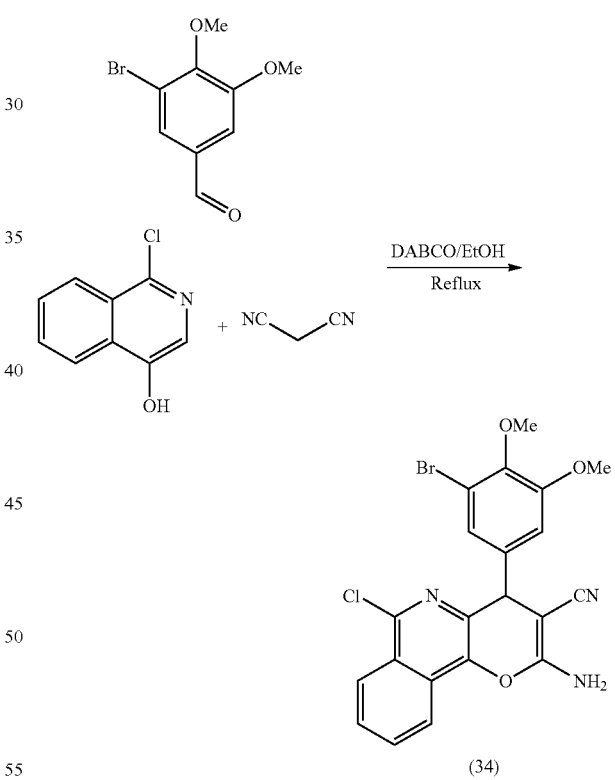

1-Chloro-4-hydroxyisoquinone (790 mg, 4.4 mmol), 5-bromo-3,4-dimethoxy-benzaldehyde (1.077 mg, 4.4 mmol) and malononitrile (295 mg, 4.4 mmol) were taken in 40 ml ethanol at room temperature, charged with DABCO (48.4 µl, 1.46 mmol) and then stirred at 80° C. under LC-MS control for 24 h. The reaction mixture was cooled down to room temperature, diluted with water to about 100 ml and the precipitates were collected by filtration, washed well with 50% aqueous ethanol and dried under vacuum to yield the title compound (1.7 g, 3.6 mmol, 82%).

Example 35

3-Amino-1-(3-bromo-4,5-dimethoxy-phenyl)-9-chloro-1H-4-oxa-5-aza-phenanthrene-2-carbonitrile (35)

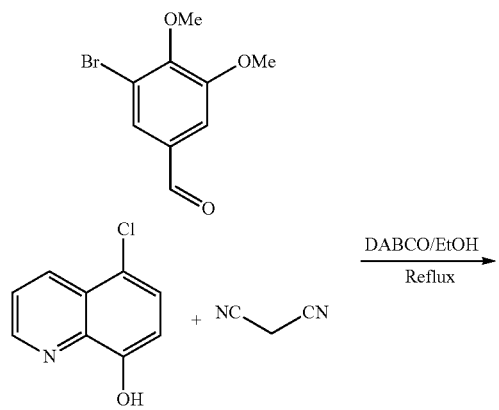

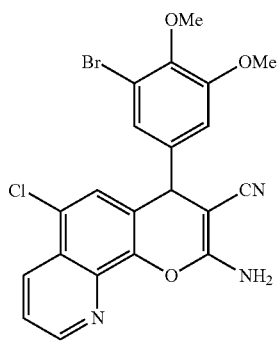

(35)

5-Chloro-8-hydroxyquinoline (790.2 mg, 4.4 mmol), 5-bromo-3,4-dimethoxy-benzaldehyde (1.077 mg, 4.4 mmol) and malononitrile (295 mg, 4.4 mmol) were taken in 40 ml ethanol at room temperature, charged with DABCO (48.4 µl, 1.46 mmol) and then stirred at 80° C. under LC-MS control for 18 h. The reaction mixture was cooled down to room temperature, diluted with water to about 100 ml and the solid were collected by filtration. It was washed with 50% aqueous ethanol. The solids were taken in 15 ml 2-propanol and stirred at 60° C. for 10 minutes, cooled down by dipping the flask in an ice bath, the solids were filtered and dried under vacuum to get the pure title compound (1.25 g, 2.64 mmol, 60%).

Example 36

2-Amino-4-(3-bromo-4,5-dimethoxy-phenyl)-4H-1-oxa-10-aza-phenanthrene-3-carbonitrile (36)

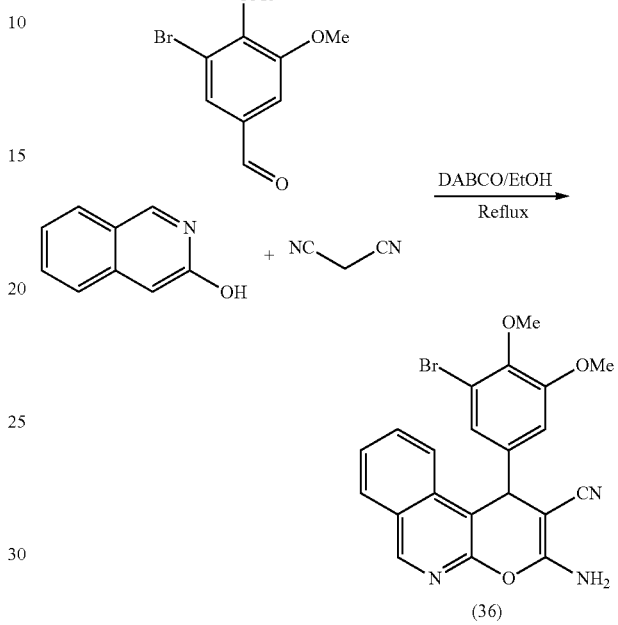

(36)

3-Hydroxyisoquinoline (638 mg, 4.4 mmol), 5-bromo-3,4-dimethoxy-benzaldehyde (1.077 mg, 4.4 mmol) and malononitrile (295 mg, 4.4 mmol) were taken in 40 ml ethanol at room temperature, charged with DABCO (48.4 µl, 1.46 mmol) and then stirred at 80° C. under LC-MS control for 24 h. The reaction mixture was cooled down to room temperature, diluted with water to about 100 ml and the precipitates were collected by filtration, washed well with 50% aqueous ethanol and dried under vacuum to yield the title compound (1.35 g, 3.08 mmol, 70%).

Example 37

3,5-Diamino-1-(3-bromo-4,5-dimethoxy-phenyl)-1H-benzo[f]chromene-2-carbonitrile (37)

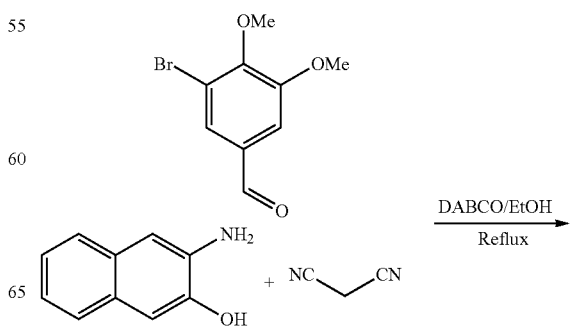

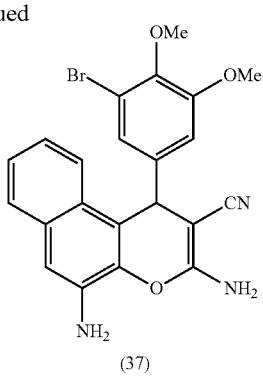

(37)

3-Aminonaphthol (700.5 mg, 4.4 mmol), 5-bromo-3,4-dimethoxy-benzaldehyde (1.077 mg, 4.4 mmol) and malononitrile (295 mg, 4.4 mmol) were taken in 40 ml ethanol at room temperature, charged with DABCO (48.4 µL, 1.46 mmol) and then stirred at 80° C. under LC-MS control for 24 h. The reaction mixture was cooled down to room temperature, diluted with water to about 100 ml and the precipitates were collected by filtration, washed well with 50% aqueous ethanol and dried under vacuum to yield the title compound (1.55 g, 3.43 mmol, 78%).

Example 38

6-Amino-8-(3-bromo-4,5-dimethoxy-phenyl)-8H-[1,3]dioxolo[4,5-g]chromene-7-carbonitrile (38)

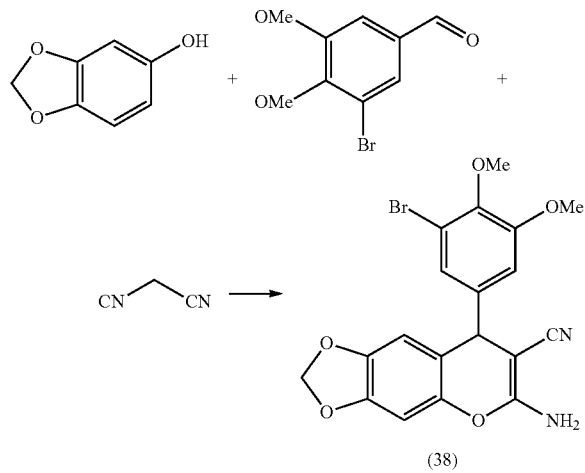

3-Bromo-4,5-dimethoxy-benzaldehyde (245 mg, 1 mmol), malononitrile (66 mg, 1 mmol) and sesamol (166 mg, 1.2 mmol) were taken in 10 ml ethanol, charged with piperidine (50 µl, 0.5 mmol) and stirred at room temperature for 3 h. The reaction mixture was then stirred at 80° C. for 64 h. Reaction was complete with the desired product. The reaction mixture was first cooled down to room temperature, diluted with water to about 30 ml, precipitates were collected by filtration, washed with 1:1 mixture of water and methanol (30 ml) and dried to pure solids (348 mg, 81%) under high vacuum.

Example 39

6-Amino-8-(3,4,5-trifluoro-phenyl)-8H-[1,3]dioxolo[4,5-g]chromene-7-carbonitrile (39)

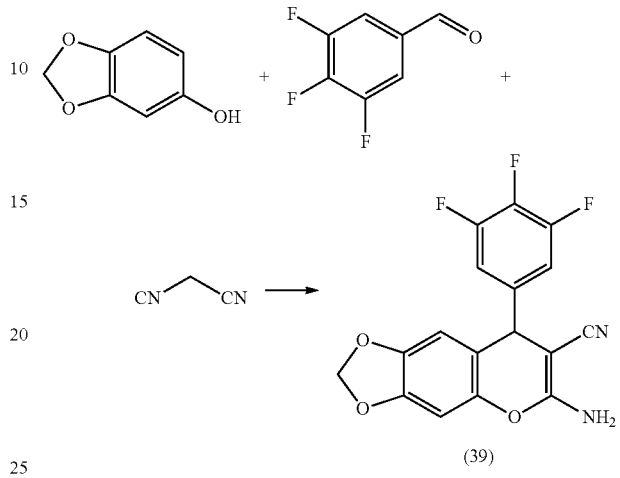

3,4-Methylenedioxyphenol (166 mg, 1.2 mmol), 3,4,5-trifluorobenzaldehyde (160 mg, 1 mmol) and malononitrile (66 mg, 1 mmol) were taken in 7 ml ethanol at room temperature, charged with piperidine (50 µL) and then stirred at 80° C. under LC-MS control till the reaction was complete. The reaction mixture was cooled down to room temperature, diluted with water to about 15 ml, stirred for 1 h, solids were collected by filtration, washed with 60% aq ethanol and dried (303 mg, 0.88 mmol, 88%).

Example 40

6-Amino-8-(3,4,5-trifluoro-phenyl)-8H-[1,3]dioxolo[4,5-g]chromene-7-carboxylic acid ethyl ester (40)

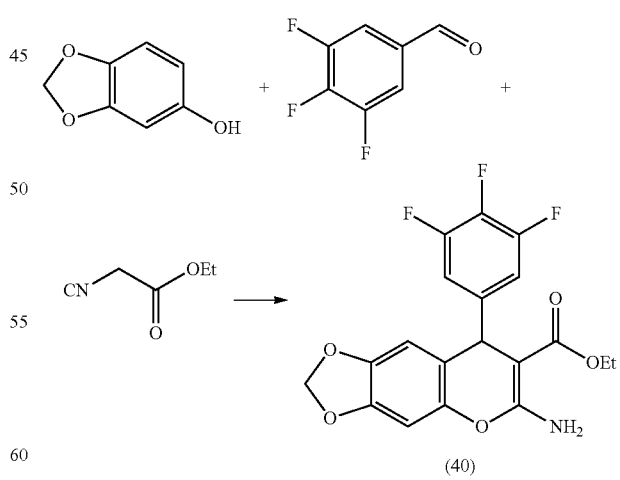

3,4-Methylenedioxyphenol (166 mg, 1.2 mmol), 3,4,5-trifluorobenzaldehyde (160 mg, 1 mmol) and ethyl cyanoacetate (113 mg, 1 mmol) were taken in 7 ml ethanol at room temperature, charged with piperidine (50 µL) and then stirred at 80° C. under LC-MS control till the reaction was complete. The reaction mixture was cooled down to room temperature, diluted with water to about 15 ml, stirred for 1 h, solids were collected by filtration, washed with 60% aq. ethanol and dried (280 mg, 0.71 mmol, 71%).

Example 41

8-(4-Allyloxy-3-bromo-5-methoxy-phenyl)-6-amino-8H-[1,3]dioxolo[4,5-g]chromene-7-carbonitrile (41)

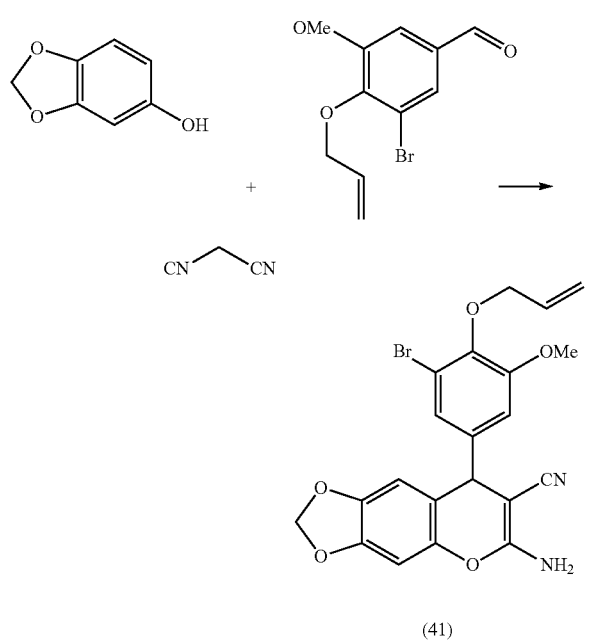

(41)

3,4-Methylenedioxyphenol (166 mg, 1.2 mmol), 4-allyloxy-3-bromo-5-methoxy-benzaldehyde (271 mg, 1 mmol) and malononitrile (66 mg, 1 mmol) were taken in 7 ml ethanol at room temperature, charged with piperidine (50 µL) and then stirred at 80° C. under LC-MS control till the reaction was complete. The reaction mixture was cooled down to room temperature, diluted with 10 ml water, stirred for 2 h at room temperature, solids were collected by filtration, washed with 1:1 mixture of ethanol/water and dried (200 mg, 0.44 mmol, 44%).

Example 42

8-(4-Allyloxy-3-bromo-5-methoxy-phenyl)-6-amino-8H-[1,3]dioxolo[4,5-g]chromene-7-carboxylic acid ethyl ester (42)

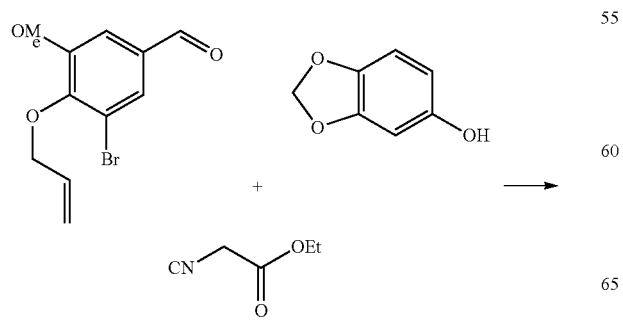

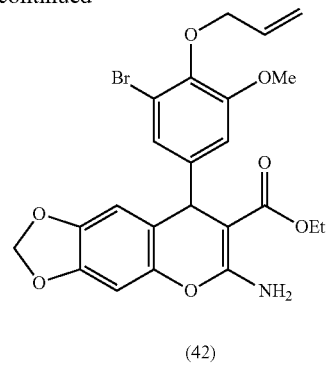

(42)

3,4-Methylenedioxyphenol (166 mg, 1.2 mmol), 4-allyloxy-3-bromo-5-methoxy-benzaldehyde (271 g, 1 mmol) and ethyl cyanoacetate (113 mg, 1 mmol) were taken in 7 ml ethanol at room temperature, charged with piperidine (50 µL) and then stirred at 80° C. under LC-MS control till the reaction was complete. The reaction mixture was cooled down to room temperature, diluted with 10 ml water, stirred for 2 h at room temperature, solids were collected by filtration, washed with 1:1 mixture of ethanol/water and dried (239 mg, 0.47 mmol, 47%).

Example 43

1-[3-Amino-1-(3-bromo-4,5-dimethoxy-phenyl)-2-cyano-1H-4-oxa-5-aza-phenanthren-6-yl]-3-ethyl-urea (43)

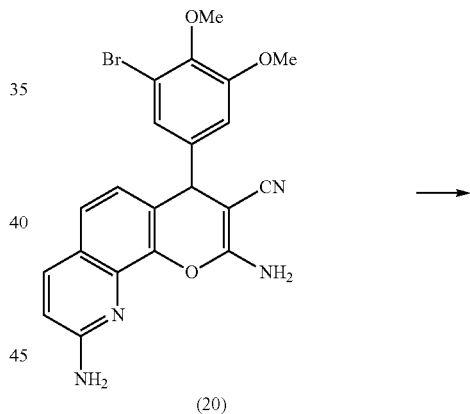

(20)

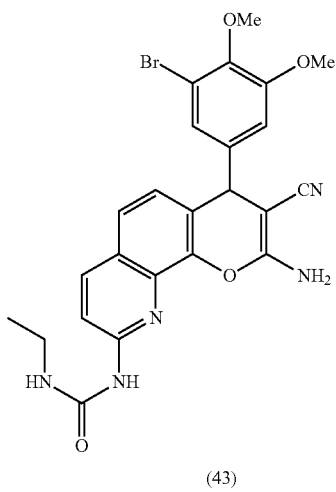

(43)

3,6-Diamino-1-(3-bromo-4,5-dimethoxy-phenyl)-1H-4-oxa-5-aza-phenanthrene-2-carbonitrile (20) (45 mg, 0.1 mmol) and ethylisocyanate (8.4 mg, 0.12 mmol) were taken in 2 ml dry acetonitril and stirred at 60° C. monitoring the reaction with LC-MS. The solvent was evaporated after the completion of the reaction. The residue was separated on HPLC (high pressure liquid chromatography) (21 mm×250 mm, RP18, 5 mm) with a methanol/water gradient (5% MeOH to MeOH in 25 min, flow 21 ml/min) to get the title compound (38 mg, 73%).

Example 44

1-[3-Amino-1-(3-bromo-4,5-dimethoxy-phenyl)-2-cyano-1H-4-oxa-5-aza-phenanthren-6-yl]-3-methyl-thiourea (44)

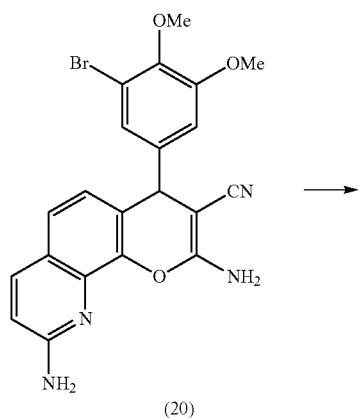

(20)

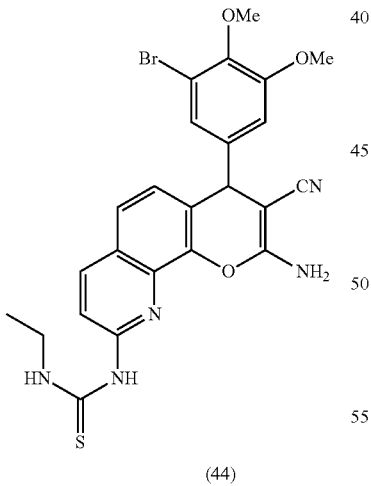

(44)

3,6-Diamino-1-(3-bromo-4,5-dimethoxy-phenyl)-1H-4-oxa-5-aza-phenanthrene-2-carbonitrile (20) (45 mg, 0.1 mmol) and ethylthioisocyanate (10.4 mg, 0.12 mmol) were taken in 2 ml dry acetonitril and stirred at 60° C. monitoring the reaction with LC-MS. The solvent was evaporated after the completion of the reaction. The residue was separated on HPLC (high pressure liquid chromatography) (21 mm×250 mm, RP18, 5 mm) with a methanol/water gradient (5% MeOH to MeOH in 25 min, flow 21 ml/min) to get the title compound (32 mg, 59%).

Example 45

3-Amino-1-(3-bromo-4,5-dimethoxy-phenyl)-6-methylamino-1H-4-oxa-5-aza-phenanthrene-2-carbonitrile (45)

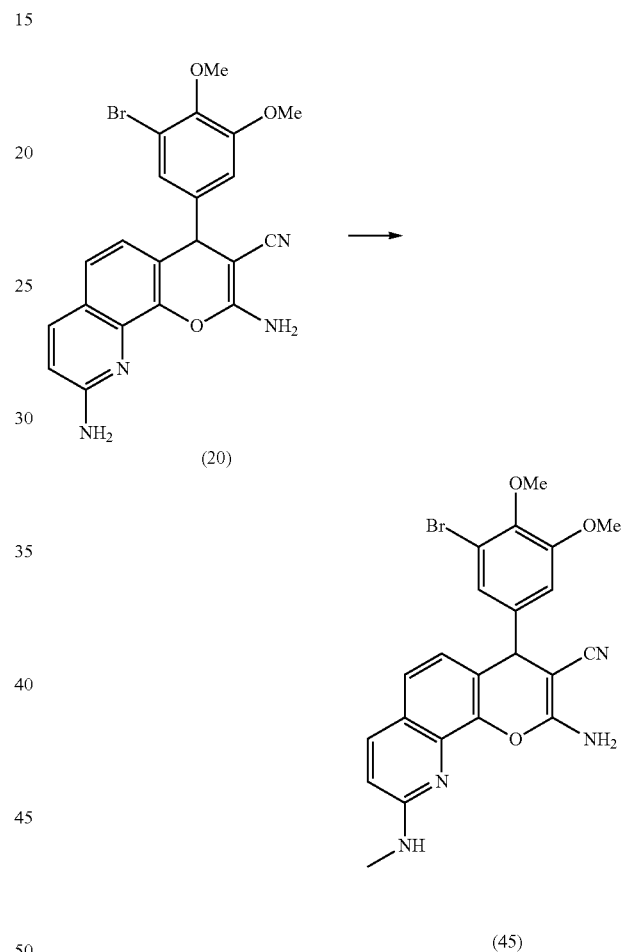

3,6-Diamino-1-(3-bromo-4,5-dimethoxy-phenyl)-1H-4-oxa-5-aza-phenanthrene-2-carbonitrile (20) (45 mg, 0.1 mmol) and potassium carbonate (7.5 mg, 0.05 mmol) were taken in 5 ml dry acetonitril, charged with iodomethane (15.4 mg, 0.11 mmol) and stirred at room temperature monitoring the reaction with LC-MS. The solvent was evaporated after the completion of the reaction. The residue was separated on HPLC (high pressure liquid chromatography) (21 mm×250 mm, RP18, 5 mm) with a methanol/water gradient (5% MeOH to MeOH in 25 min, flow 21 ml/min) to get the title compound (41 mg, 87.8%).

Example 46

N-[3-Amino-1-(3-bromo-4,5-dimethoxy-phenyl)-2-cyano-1H-4-oxa-5-aza-phenanthren-6-yl]-acetamide (46)

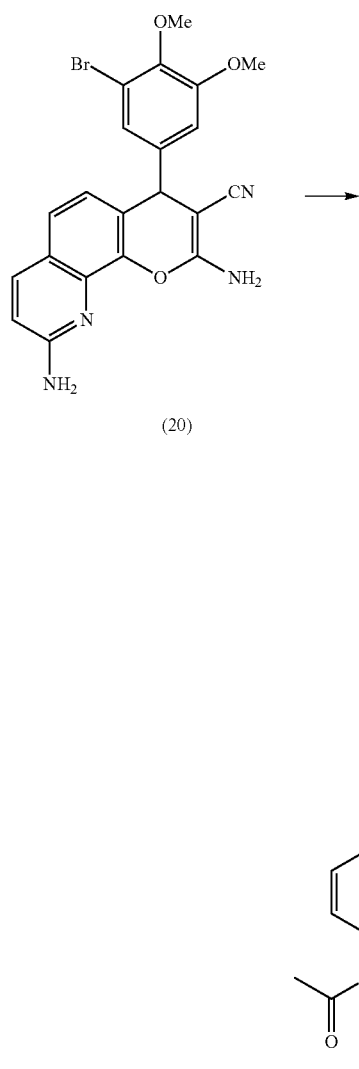

3,6-Diamino-1-(3-bromo-4,5-dimethoxy-phenyl)-1H-4-oxa-5-aza-phenanthrene-2-carbonitrile (20) (45 mg, 0.1 mmol) was taken in 2 ml pyridine at 0° C., charged with acetic anhydride (11 mg, 0.11 mmol) by drop wise addition and stirred at room temperature monitoring the reaction with LC-MS. The solvent was evaporated after the completion of the reaction. The residue was separated on HPLC (high pressure liquid chromatography) (21 mm×250 mm, RP18, 5 mm) with a methanol/water gradient (5% MeOH to MeOH in 25 min, flow 21 ml/min) to get the title compound (35 mg, 71.4%).

Example 47

2-Amino-4-(3-bromo-4,5-dimethoxy-phenyl)-7-methoxy-4H-benzo[h]chromene-3-carbonitrile (47)

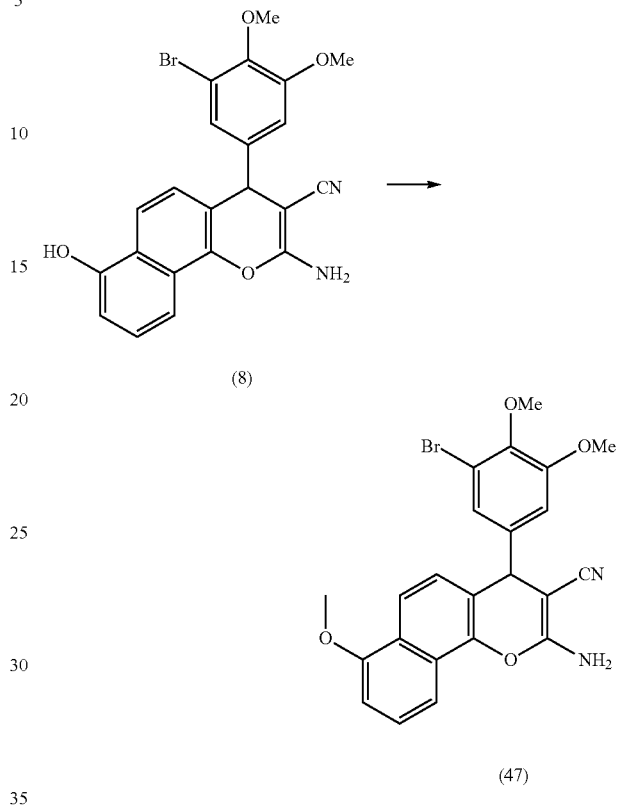

2-Amino-7-hydroxy-4-(3-bromo-4,5-dimethoxy-phenyl)-4H-benzo[h]chromene-3-carbonitrile (8) (45 mg, 0.1 mmol) and potassium carbonate (14 mg, 0.1 mmol) were taken in dry acetonitril (5 ml) at room temperature, stirred for 1 h, charged with iodomethane (15.6 mg, 0.11 mmol) and stirred further at room temperature under LC-MS control. The reaction mixture was diluted with water (10 ml) under stirring, stirred further at room temperature for 2 h, the precipitates were collected by filtration, washed with water and dried to get the title compound (43 mg, 92%).

Example 48

2-Amino-4-(3-bromo-4,5-dimethoxy-phenyl)-6-methoxy-4H-benzo[h]chromene-3-carbonitrile (48)

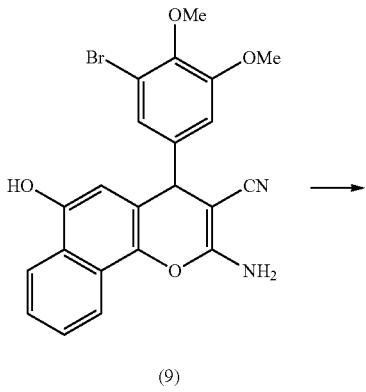

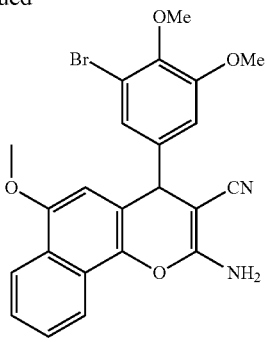

(48)

2-Amino-6-hydroxy-4-(3-bromo-4,5-dimethoxy-phenyl)-4H-benzo[h]chromene-3-carbonitrile (9) (45 mg, 0.1 mmol) and potassium carbonate (14 mg, 0.1 mmol) were taken in dry acetonitril (5 ml) at room temperature, stirred for 1 h, charged with iodomethane (15.6 mg, 0.11 mmol) and stirred further at room temperature under LC-MS control. The reaction mixture was diluted with water (10 ml) under stirring, stirred further at room temperature for 2 h, the precipitates were collected by filtration, washed with water and dried to get the title compound (40 mg, 85.6%).

Example 49

2-Amino-4-(3-bromo-4,5-dimethoxy-phenyl)-7-methylamino-4H-benzo[h]chromene-3-carbonitrile (49)

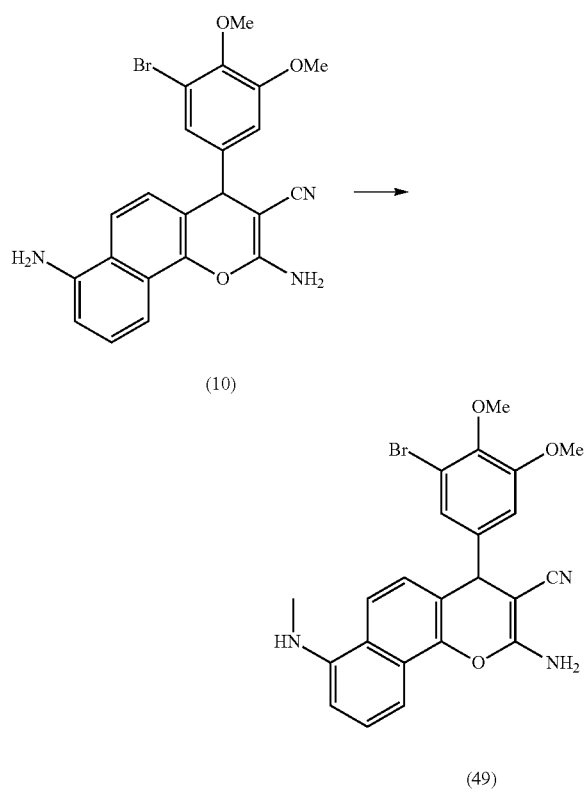

2,7-Diamino-4-(3-bromo-4,5-dimethoxy-phenyl)-4H-benzo[h]chromene-3-carbonitrile (10) (45 mg, 0.1 mmol) and potassium carbonate (14 mg, 0.1 mmol) were taken in dry acetonitril (5 ml) at room temperature, stirred for 1 h, charged with iodomethane (15.6 mg, 0.11 mmol) and stirred further at room temperature under LC-MS control. The reaction mixture was diluted with water (10 ml) under stirring, stirred further at room temperature for 2 h, the precipitates were collected by filtration, washed with water and dried to get the title compound (42 mg, 89.9%).

Example 50

2-Amino-4-(3-bromo-4,5-dimethoxy-phenyl)-7-dimethylamino-4H-benzo[h]chromene-3-carbonitrile (50)

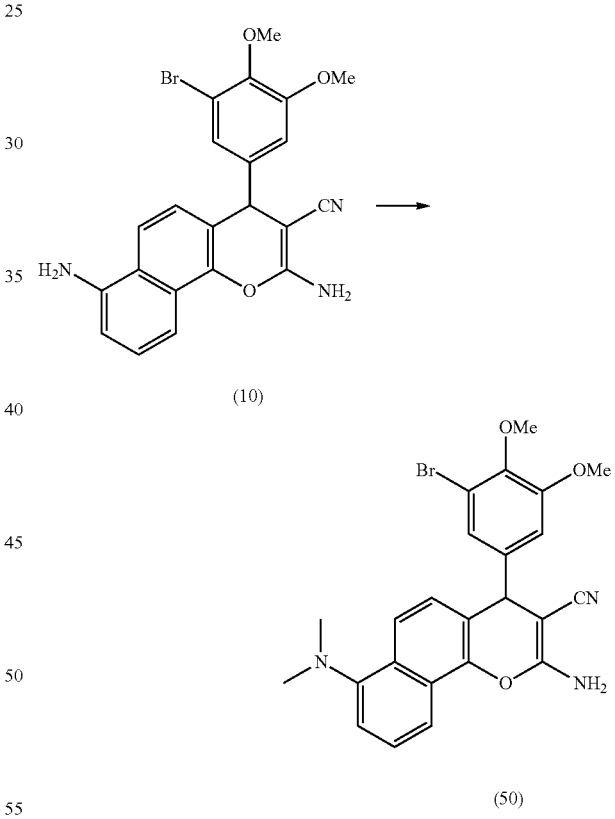

2,7-Diamino-4-(3-bromo-4,5-dimethoxy-phenyl)-4H-benzo[h]chromene-3-carbonitrile (10) (45 mg, 0.1 mmol) and potassium carbonate (21 mg, 0.15 mmol) were taken in dry acetonitril (5 ml) at room temperature, stirred for 1 h, charged with iodomethane (31.2 mg, 0.22 mmol) and stirred further at room temperature under LC-MS control. The reaction mixture was diluted with water (10 ml) under stirring, stirred further at room temperature for 2 h, the precipitates were collected by filtration, washed with water and dried to get the title compound (41 mg, 85.4%).

Example 51

2-Amino-4-(3-bromo-4,5-dimethoxy-phenyl)-7-acetylamino-4H-benzo[h]chromene-3-carbonitrile (51)

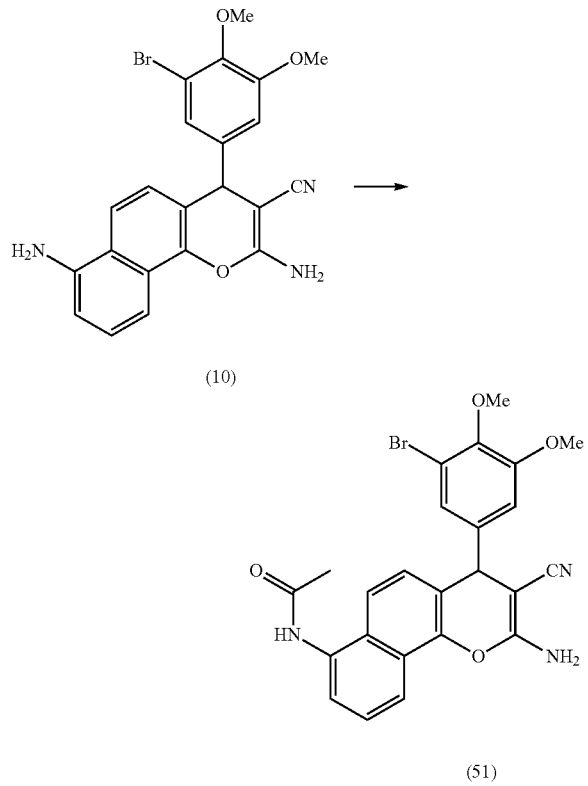

(10)

(51)

2,7-Diamino-4-(3-bromo-4,5-dimethoxy-phenyl)-4H-benzo[h]chromene-3-carbonitrile (10) (45 mg, 0.1 mmol) was taken in pyridine (2 ml) at 0° C., charged with acetic anhydride (11 mg, 0.11 mmol) and stirred further at 0° C. under LC-MS control. The reaction mixture was diluted with water (10 ml) under stirring, stirred further at room temperature for 2 h, the precipitates were collected by filtration, washed with water and dried to get the title compound (46 mg, 93%).

Example 52

4-(3-Bromo-4,5-dimethoxy-phenyl)-3-(5-methylaminomethyl-[1,2,4]oxadiazol-3-yl)-4H-benzo[h]chromen-2-ylamine (52)

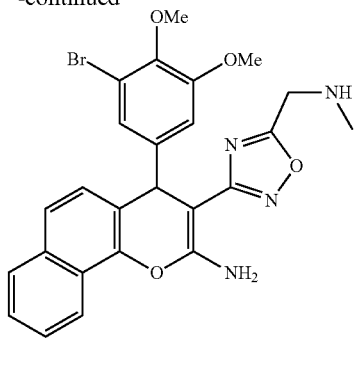

(24)

(52)

4-(3-Bromo-4,5-dimethoxy-phenyl)-3-(5-chloromethyl-[1,2,4]oxadiazol-3-yl)-4H-benzo[h]chromen-2-ylamine (24) (528 mg, 1 mmol) and triethylamine (140 µl, 1 mmol) and 2M methanolic solution of methylamine (600 1.2 mmol) is taken in acetonitril (10 ml) and stirred at room temperature under LC-MS control till the reaction is complete. The reaction mixture is diluted with water to about 50 ml and stirred for 2 h at room temperature. Thus resulting precipitates are separated by filtration, washed well with water and is dried under high vacuum to get solids of the title compound.

Example 53

3-Amino-1-(3-bromo-4,5-dimethoxy-phenyl)-9-methylamino-1H-4-oxa-10-aza-phenanthrene-2-carbonitrile (53)

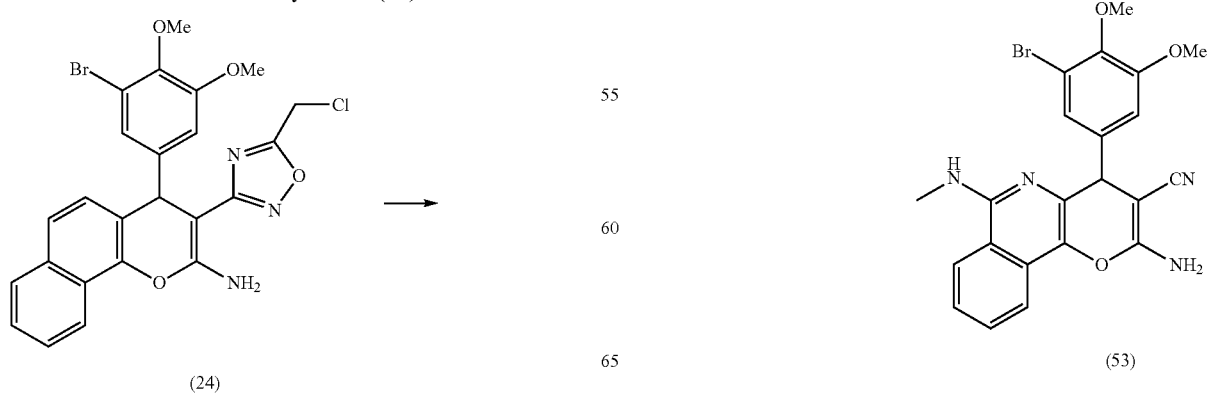

(34)

(53)

3-Amino-1-(3-bromo-4,5-dimethoxy-phenyl)-9-chloro-1H-4-oxa-10-aza-phenanthrene-2-carbonitrile (34) (47 mg, 0.1 mmol) and triethylamine (14 μl, 0.1 mmol) and methylamine (2M in MeOH, 75 μl, 0.15 mmol) were taken in dry NMP (2 ml) and stirred at 80° C. till the reaction was complete. The reaction mixture was diluted with water to about 7 ml, stirred at room temperature for 2 h, precipitates were collected by filtration, washed with water. The residue was then purified on HPLC (high pressure liquid chromatography) (21 mm×250 mm, RP18, 5 mm) with a methanol/water gradient (5% MeOH to MeOH in 25 min, flow 21 ml/min) to pure title compound (36 mg, 77%).

Example 54

Examination of Wnt Signaling Pathway Inhibiting Activity of Selected Compounds

To screen for small-molecule modulators of the Wnt signaling pathway, a reporter gene based assay describing the modulation of the TCF4 transcription factor was used. More specifically 4000 Hek293T cells were seeded into 384 high density plates. 24 h after seeding a Wnt-sensitive reporter (6×TCF-luciferase (Firefly) (pTOP-FLASH; "Armadillo coactivates transcription driven by the product of the Drosophila segment polarity gene dTCF", Cell, 1997, 88(6), pages 789-99)) and constitutively expressed control reporter (Renilla luciferase pCMV-RL) were transfected into Hek293T. Wnt signaling was stimulated by cotransfecting mouse Wnt1, mouse Frizzled 8 and human LRP6 according to "Casein kinase 1 gamma couples Wnt receptor activation to cytoplasmic signal transduction", Nature, 2005, 438 (7069), pages 867-872. 24 h after pathway stimulation compounds were added at a concentration of 10 microM and allowed to incubate for 24 h. For the evaluation of the $IC_{50}$ the respective compound was applied in increasing concentrations yielding final concentrations per well of 5 nM-100 microM.

The $IC_{50}$-values of the Wnt pathway inhibitory activity of compounds (1), (4), (6), (7), (16) to (20), (28) to (31) and (38) to (42) are shown in table 1.

TABLE 1

$IC_{50}$-values of the Wnt pathway inhibitory activity for of compounds (1), (4), (6), (7), (16) to (20), (28) to (31) and (38) to (42)

| Compound | Wnt1/Frzd8 $IC_{50}$ [nM] |
|---|---|
| (1) | 46 |
| (4) | 86 |
| (6) | 855 |
| (7) | 316 |
| (16) | 1126 |
| (17) | 20 |
| (18) | 33 |
| (19) | 3 |
| (20) | 6 |
| (28) | 2396 |
| (29) | 6482 |
| (30) | 697 |
| (31) | 1965 |
| (38) | 3118 |
| (39) | 1365 |
| (40) | 3424 |
| (41) | 45 |
| (42) | 55 |

Example 55

Examination of Toxicity in Hek293T and HepG2

For examination of cytotoxicity in these cancer cell lines the commercial available CellTiterGlo® Reagent (Promega, USA) was used according to the manufactor.

Compounds were applied to Hek293T (denoted (a)) or HepG2 (denoted (b)), cultured in Dulbecco's Modified Eagles Medium, supplemented with 10% fetal calf serum and 1% penicillin/streptomycin. Cells were grown in T75 flasks at 37° C., 5% CO2 and trypsinized when 60-80% confluent by adding 2 ml of 0.25% TrypsinEDTA solution. Cells were then re-suspended into culture medium yielding approx. 4000 cells (a) or 4500 cells (b), suspended in 30 microl medium. 48 h after cell seeding, compounds were added to yield the desired final concentrations. 24 h after compound addition cytotoxicity was evaluated. For this purpose the media was removed and CellTiterGlo® was added according to the manufactors manual. In this assay the luciferase emission readout is directly correlated with the cellular amount of ATP, low luciferase emission thus is reflecting cytotoxicity of a compound. For the evaluation of the $IC_{50}$ the compound was applied in increasing concentrations yielding final concentrations per well of 5 nM-100 microM.

$IC_{50}$-values of the cytotoxic activity of compounds (1), (4), (6), (7), (16) to (20), (29) to (32) and (39) to (43) against Hek293T and HepG2 are shown in table 2.

TABLE 2

$IC_{50}$-values against Hek293T and HepG2 of compounds (1), (4), (6), (7), (16) to (20), (28) to (31) and (38) to (42)

| Compound | Hek293T $IC_{50}$ [nM] | HepG2 $IC_{50}$ [nM] |
|---|---|---|
| (1) | >90000 | >90000 |
| (4) | >90000 | >90000 |
| (6) | >90000 | >90000 |
| (7) | >90000 | >90000 |
| (16) | >90000 | >90000 |
| (17) | >90000 | >90000 |
| (18) | >90000 | >90000 |
| (19) | >90000 | >90000 |
| (20) | >90000 | 37048 |
| (28) | >90000 | 31676 |
| (29) | >90000 | 42539 |
| (30) | >90000 | >90000 |
| (31) | >90000 | >90000 |
| (38) | >90000 | >90000 |
| (39) | >90000 | >90000 |
| (40) | >90000 | >90000 |
| (41) | >90000 | >90000 |
| (42) | >90000 | >90000 |

Example 56

Examination of Cell Line Specific Cytotoxicity

For examination of cell line-specific cytotoxicity, compounds were applied to human colorectal cancer cells (HCT116, denoted (1); SW480, denoted (2); Dld-1, denoted (3)) and human fibroblasts (HS-68, denoted (4)), cultured in Mc Coy's ((1)) and Dulbecco's Modified Eagles Medium ((2)-(4)), supplemented with 10% ((1)-(3)) and 20% ((4)) fetal calf serum and 1% penicillin/streptomycin. Cells were grown in T75 flasks at 37° C., 5% CO2 and trypsinized when 60-80% confluent by adding 2 ml of 0.25% TrypsinEDTA (ethylenediaminetetraacetic acid) solution. Cells were then re-suspended into culture medium yielding approx. 750 cells, suspended in 45 microl medium, were plated into each well of a black 384-well plate for fluorescence imaging experiments. 24-36 hr later 5 microl compound solution (100 microM compound dissolved in ultra pure water containing 1% DMSO (dimethylsulfoxide)), were added to achieve a final concentration of 10 microM and were incubated for at least 72 hr. Compound incubation was terminated by (a) fixation and (b) permcabilisation of cells, followed by (c) fluorescence labeling of cell nuclei for cytometric quantification or by immunocytochemistry for microscopic evaluation of cell morphology. The three steps were performed by replacing the solution of the previous step in each well of a 384-well plate by (a) 30 microl PBS (phosphate buffered saline) containing 5% PFA (paraformaldehyde), (b) 30 microl PBS containing 0.2% TritonX-100 and (c) 10 microl PBS containing Hoechst-33342 for cytometry or Hoechst-33342, FITC-(fluorescein isothiocyanate-) labeled alpha-tubulin antibodies and TRITC-(tetramethylrhodamine isothiocyanate-)labeled phalloidin for microscopy. Solutions were incubated for 15 (a,b) and 30 min (c) in the dark at room temperature. Cells were washed twice between each step with 30 microl PBS. The assay system was miniaturized and adapted to automated workflow using liquid-handling robotics.

Cell line-specific cytotoxicity was quantified by counting the number of Hoechst labeled nuclei per well of a 384-well plate using a plate cytometer. Data obtained with the cytometer was analysed using standard data analysis software.

Identified hits were further evaluated by visual inspection of fluorescence micrographs obtained from imaging using a conventional fluorescence microscope.

The results for normal cells (HS68) are shown in table 3.

TABLE 3

Influence of of compounds ((1), (4), (6), (7), (16) to (20), (28) to (31) and (38) to (42) on normal cells (HS68)

| Compound | HS68 $IC_{50}$ [nM] |
|---|---|
| (1) | 87 |
| (4) | 215 |
| (6) | >90000 |
| (7) | >90000 |
| (16) | 4945 |
| (17) | >90000 |
| (18) | 2771 |
| (19) | nd |
| (20) | nd |
| (28) | >90000 |
| (29) | >90000 |
| (30) | 5150 |
| (31) | >90000 |
| (38) | 4164 |
| (39) | >90000 |
| (40) | >90000 |
| (41) | 641 |
| (42) | 469 | nd: not determinable

The examination of the antiproliferative activity against human colon carcinoma cells Dld1, HCT116 and SW480 was carried out in analogy to the procedure carried out for HS68. The respective compound applied in increasing concentrations yielding final concentrations per well of 5 nM-90 microM. Compounds of the present invention have potent antiproliferative activity against human colon carcinoma cells as shown for Dld1, HCT116 and SW480 in Table 4.

TABLE 4

Influence of compounds (1), (4), (6), (7), (16) to (20), (28) to (31) and (38) to (42) on Dld1, HCT116 and SW480 colon carcinoma cells

| Compound | Dld1 $IC_{50}$ [nM] | HCT116 $IC_{50}$ [nM] | SW480 $IC_{50}$ [nM] |
|---|---|---|---|
| (1) | 38 | 49 | 56(a) |
| (4) | 171 | 146 | 332 |
| (6) | 3819 | 8604 | 5956(a) |
| (7) | 474(a) | 922 | 2861 |
| (16) | 2901 | 3340 | 3158 |
| (17) | 643 | 305(a) | 577(a) |
| (18) | 185 | 331 | 19671 |
| (19) | 21 | 17 | nd |
| (20) | 14 | 15 | nd |
| (28) | 21954 | 30314 | 53605 |
| (29) | >90000 | >90000 | 38541 |
| (30) | 8975 | 2903 | 7598 |
| (31) | 4557 | 10004 | 11999 |
| (38) | 719 | 1054 | 3087 |
| (39) | 1085 | 666 | 2692 |
| (40) | 15658 | >90000 | 6385 |
| (41) | 470 | 551 | 618 |
| (42) | 293 | 250 | 343 | nd: not determinable

Examples 57 to 70

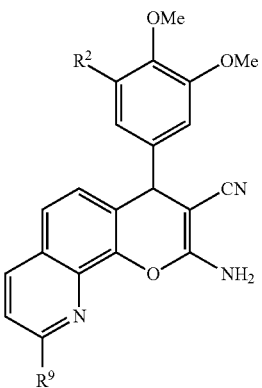

TABLE 5 compounds (57) to (70):

| Compound | $R^2$ | $R^9$ |
|---|---|---|
| (57) | Br | $CH_2OH$ |
| (58) | Br | $CH_2NH_2$ |
| (59) | Cl | OH |
| (60) | Cl | $NH_2$ |
| (61) | Cl | $CH_2OH$ |
| (62) | Cl | $CH_2NH_2$ |
| (63) | F | OH |
| (64) | F | $NH_2$ |
| (65) | F | $CH_2OH$ |
| (66) | F | $CH_2NH_2$ |
| (67) | $OCH_3$ | OH |
| (68) | OCH3 | $NH_2$ |
| (69) | OCH3 | $CH_2OH$ |
| (70) | OCH3 | $CH_2NH_2$ |

Compounds (57), (58), (60) to (62), (64) to (66) and (68) to (70) were prepared in analogy to the procedure of examples 19 and 20 using the respective 2,8-quinoline derivatives and the respective 3-$R^2$-4,5-dimethoxy-benzaldehydes.

Compounds (59), (63) and (67) were prepared by suspending (3-R²-4,5-dimethoxy-phenyl)-(2,8-dihydroxy-quinolin-7-yl)-methanone (1 mmol) in 25 ml methanol at room temperature under argon and then charging with malononitrile (4 mmol) and piperidine (1 mmol). The mixture was stirred at room temperature for 16 h. Acetic acid (1 ml), water (10 ml) and then sodium cyanoborohydride (4 mmol) were added and stirred further at room temperature until the reaction was complete. Diluted with water to 100 ml, stirred for 1 h, solids were collected by filtration, washed well with water, 50% aq. ethanol and then with 25% ethylacetate in cyclohexane.

The Wnt pathway inhibitory activity of compounds (57) to (70) was investigated according to the procedure described in example 54. The $IC_{50}$-values of the Wnt pathway inhibitory activity of compounds (57) to (70) were below 100 nM.

The cytotoxic activity of compounds (57) to (70) was investigated according to the procedure described in example 55. The $IC_{50}$-values against Hek293T of compounds (57) to (70) lied above 50 microM.

The influence of compounds (57) to (70) on colon cancer cell lines Dld1 and HCT116 was determined according to the procedure described in example 56. $IC_{50}$-values for the cytotoxicity against these cell lines were below 100 nM for compounds (57) to (70) showing a strong effect on cancer cells being associated with an aberrant Wnt signalling pathway activity.

Example 71

Enantionmeric Separation of 3,6-diamino-1-(3-bromo-4,5-dimethoxy-phenyl)-1H-4-oxa-5-aza-phenanthrene-2-carbonitrile (20) and Determination of the Activity of the Enantionmers Chiral HPLC (High Pressure Liquid Chromatography) and SFC (Supercritical Fluid Chromatography) were used for the analytical and preparative chiral separation of compound (20) respectively.

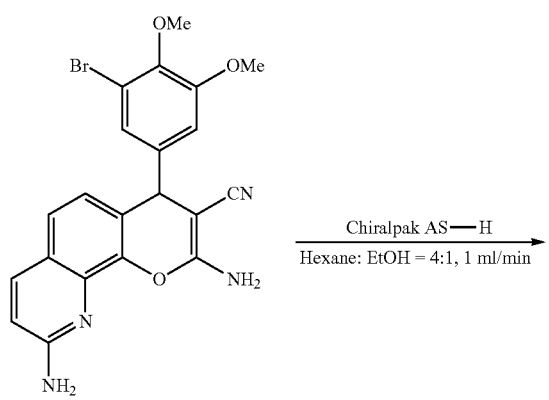

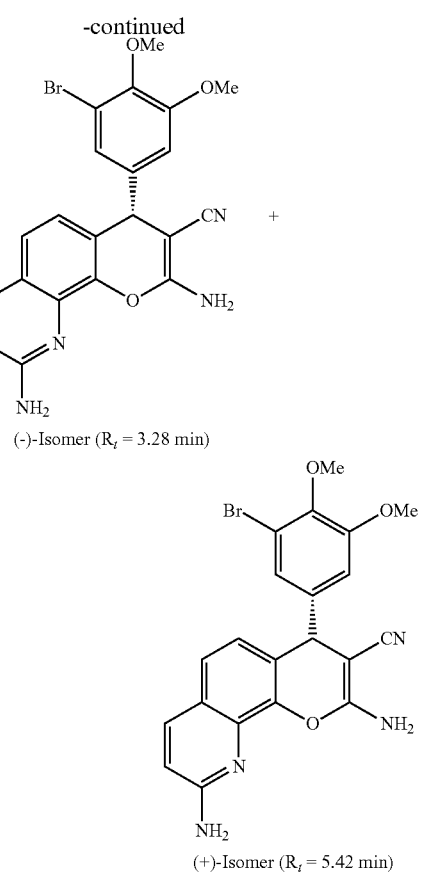

1.1. Preparative Separation Method

The racemic mixture (300 mg) of 3,6-Diamino-1-(3-bromo-4,5-dimethoxy-phenyl)-1H-4-oxa-5-aza-phenanthrene-2-carbonitrile (compound (20)) was separated into its enantiomers with the following methods:

Instrument: Thar 80 preparative Supercritical Fluid Chromatography (SFC)
Column: Chiralccl AS 250 mm×25 mm, 5 μm
Mobile phase: 70% Carbondioxide and 30% ethanol with 0.05% 2-aminopropane
Flow rate: 60 g/min
Temperature: 40° C.
Sample preparation: The racemate was dissolved in a 1:1 mixture of ethanol and acetonitrile with a final concentration of 10 mg/ml.
Injection volume: 2 ml per injection.

1.2. Work Up

After separation, the fractions were dried off via rotary evaporator at bath temperature 30° C. to get the two enantiomers. After separation, 89.2 mg of (−)-Isomer with e.e. value 100% and 105.6 mg of (+)-Isomer with e.e. value 100% were obtained respectively.

2. Analytical Method

Instrument: Shimadzu LC-20AB analytical HPLC
Column: Chiralcel AS-H, 250 mm×4.6 mm, 5 μm
Mobile phase: 80% n-hexane and 20% ethanol with 0.05% 2-propylamine
Flow rate: 1.0 ml/min
Detection: 220 nm Properties of the pure enantiomers are displayed in Table 6. The e.e values were determined by chiral HPLC.

TABLE 6

Properties of the enantiomeres (20)-1 and (20)-2 of compound (20)

| NO. | Retention Time | $[\alpha]_D$ at 24° C. | Salt | Purity | Analytical methods | e.e. value | Net_weight |
|---|---|---|---|---|---|---|---|
| (20)-1 | 3.28 min | −238.53° +/−0.12° | FREE | 99.5% | NMR, LCMS, HPLC | 100.0% | 89.2 mg |
| (20)-2 | 5.42 min | +235.14° +/−0.24° | FREE | 99.6% | NMR, LCMS, HPLC | 100.0% | 105.6 mg |

The Wnt pathway inhibitory activity was determined as described in example 54. The influence of the racemate and the two separated enantiomers on colon cancer cell lines Dld1 and HCT116 was determined according to the procedure described in example 56. The results are shown in Table 7.

TABLE 7

Comparison of the biological activities of the racemate with the pure enantiomers of compound (20)

| Activity | $IC_{50}$ Racemate (20) | $IC_{50}$ (−)-Isomer (20)-1 | $IC_{50}$ (+)-Isomer (20)-2 |
|---|---|---|---|
| against Wnt-Pathway | 5 nM | <5 nM | 330 nM |
| against colon cancer cell lines HCT 116 | 5 nM | <5 nM | 354 nM |
| against colon cancer cell lines DLDl | 10 nM | <5 nM | 356 nM |

The invention claimed is:

1. A compound of formula (IIc)

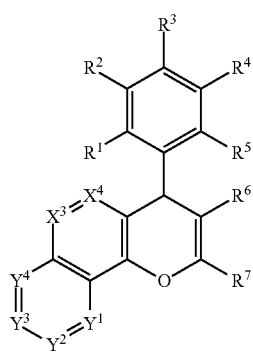

(IIc)

wherein
$X^3$ is N;
$X^4$ is N or $CR^8$;
$Y^1$, $Y^2$, $Y^3$ and $Y^4$ independently from each other are N or $CR^9$ wherein $R^9$ may be same or different and wherein up to 3 of the group $Y^1$, $Y^2$, $Y^3$ and $Y^4$ may be N;
$R^1$, $R^4$, and $R^5$ are H, Br, F, or Cl;
$R^2$ and $R^3$ are selected from H, OH; halogen; CN; $C_1$-$C_6$ alkyl; $N(R^{1a}R^{1b})$; and $OR^{1a}$; wherein alkyl is optionally substituted by one or more groups $R^{10}$ which are same or different; or $R^2$ and $R^3$ form together $OCH_2O$; and wherein at least 3 of the group of $R^1$; $R^2$; $R^3$; $R^4$; and $R^5$ are not H;
$R^{1a}$ and $R^{1b}$ are independently from each other selected from H; $C_1$-$C_6$ alkyl; allyl; $C_2$-$C_6$ alkynyl; and benzyl;

$R^{10}$ is selected from $OR^{10a}$ and $N(R^{10a}R^{10b})$;
$R^{10a}$ and $R^{10b}$ are independently from each other selected from H and $C_1$-$C_6$ alkyl;
$R^6$ is CN;
$R^7$ is $NH_2$;
$R^8$ is selected from H; OH; halogen; $OR^{8a}$; $NH_2$; $NHR^{8a}$; $N(R^{8a}R^{8b})$, $CH_2OH$; $CH_2OR^{16a}$; $CH_2NH_2$; $CH_2NHR^{16a}$; $CH_2N(R^{16a}R^{16b})$; $C(O)NH_2$; $C(O)$; $NHR^{8a}$; $C(O)N(R^{8a}R^{8b})$; COOH; and $C(O)OR^{8a}$;
$R^{8a}$ and $R^{8b}$ are independently from each other selected from $C_1$-$C_6$ alkyl;
$R^{16a}$ and $R^{16b}$ are independently from each other selected from $C_1$-$C_6$ alkyl;
$R^9$ is selected from H; OH; $C_1$-$C_6$ alkyl; $C_3$-$C_7$ cycloalkyl; $C_3$-$C_7$ heterocyclyl; $CH_2OH$; $CH_2OR^{13a}$; $CH_2NH_2$; $CH_2NHR^{13a}$; $CH_2N(R^{13a}R^{13b})$; $OR^{9a}$; $C(O)OH$; $C(O)$ $OR^{9a}$; $C(O)NH_2$; $C(O)NHR^{9a}$; $C(O)N(R^{9a}R^{9b})$; $OC(O)R^{9a}$; $N(R^{9a})C(O)R^{9b}$; $N(R^{9a})C(O)N(R^{9b}R^{9c})$; $N(R^{9a})C(S)N(R^{9b}R^{9c})$; $NH_2$; $NHR^{9a}$; and $N(R^{9a}R^{9b})$; wherein alkyl; cycloalkyl; and heterocyclyl are optionally substituted by one or more $R^{13}$, which are same or different;
$R^{9a}$; $R^{9b}$; and $R^{9c}$ are independently from each other selected from H; $C_1$-$C_6$ alkyl; $C_2$-$C_6$ alkenyl; and benzyl;
$R^{13}$ is selected from OH; $OR^{13a}$; and $N(R^{13a}R^{13b})$;
$R^{13a}$ and $R^{13b}$ are independently from each other selected from H and $C_1$-$C_6$ alkyl;
and pharmaceutically acceptable salts thereof.

2. The compound of claim 1, wherein at least one substituent $R^9$ is not H; and pharmaceutically acceptable salts thereof.

3. The compound of claim 1, wherein at least 1 member of the group $Y^1$, $Y^2$, $Y^3$ and $Y^4$ is N; and pharmaceutically acceptable salts thereof.

4. The compound of claim 1, wherein $R^1$; $R^4$; and $R^5$ are independently from each other selected from H; Br; and Cl; and $R^2$ and $R^3$ are $OCH_3$; and pharmaceutically acceptable salts thereof.

5. The compound of claim 1, wherein $R^8$ is selected from H; OH; $OR^{8a}$; $NH_2$; $NHR^{8a}$; $N(R^{8a}R^{8b})$ $CH_2OH$; $CH_2OR^{16a}$; $CH_2NH_2$; $CH_2NHR^{16a}$; $CH_2N(R^{16a}R^{16b})$; $C(O)$ $NH_2$; $C(O)NHR^{8a}$; $C(O)N(R^{8a}R^{8b})$ $C(O)OH$; and $C(O)$ $OR^{8a}$;
and pharmaceutically acceptable salts thereof.

6. The compound of claim 1, wherein said compound is a modulator of the Wnt signalling pathway.

7. A pharmaceutical composition containing a compound of claim 1 in a pharmaceutical carrier.

8. The pharmaceutical composition of claim 7 in a kit.

* * * * *